(12) United States Patent
Sardesai et al.

(10) Patent No.: US 11,878,132 B2
(45) Date of Patent: Jan. 23, 2024

(54) APPARATUS AND METHOD FOR ADVANCING CATHETERS OR OTHER MEDICAL DEVICES THROUGH A LUMEN

(71) Applicant: VASOINNOVATIONS INC., South Pasadena, CA (US)

(72) Inventors: Rajendra Gurudas Sardesai, Arcadia, CA (US); Samir Bipin Pancholy, Clarks Summit, PA (US); Tejas Madhusudan Patel, Ahmedabad (IN)

(73) Assignee: Vasoinnovations Inc., South Pasadena, CA (US)

( * ) Notice: Subject to any disclaimer, the term of this patent is extended or adjusted under 35 U.S.C. 154(b) by 0 days.

(21) Appl. No.: 18/022,264

(22) PCT Filed: Aug. 23, 2021

(86) PCT No.: PCT/US2021/047186
§ 371 (c)(1),
(2) Date: Feb. 20, 2023

(87) PCT Pub. No.: WO2022/046654
PCT Pub. Date: Mar. 3, 2022

(65) Prior Publication Data
US 2023/0321411 A1    Oct. 12, 2023

Related U.S. Application Data

(63) Continuation of application No. 17/221,448, filed on Apr. 2, 2021, which is a continuation-in-part of
(Continued)

(51) Int. Cl.
*A61M 25/10*    (2013.01)
*A61M 25/00*    (2006.01)
*A61F 2/958*    (2013.01)
*A61M 25/01*    (2006.01)

(52) U.S. Cl.
CPC ......... *A61M 25/1011* (2013.01); *A61F 2/958* (2013.01); *A61M 25/0052* (2013.01);
(Continued)

(58) Field of Classification Search
CPC .............. A61M 25/1011; A61M 25/04; A61M 25/0102; A61M 25/104; A61M 2025/1088; A61M 2025/0293; A61M 2025/1052
See application file for complete search history.

(56) References Cited

U.S. PATENT DOCUMENTS 4,294,233 A    10/1981    Takahashi
4,425,919 A    1/1984    Alston et al.
(Continued)

FOREIGN PATENT DOCUMENTS

| DE | 102017118468 A1 | 2/2019 |
| EP | 0885624 A2 | 12/1998 |
| EP | 1676595 A1 | 7/2006 |
| EP | 3037122 A1 | 6/2016 |

(Continued)

OTHER PUBLICATIONS

Tejas Patel, et al,"Balloon-Assisted Tracking of a Guide Catheter Through Difficult Radial Anatomy: A Tech. Report" Catheterization and Cardiovasc Intervent. 81:E215-8 (2013).
(Continued)

*Primary Examiner* — Tiffany Legette
(74) *Attorney, Agent, or Firm* — Rajendra Gurudas Sardesai

(57) ABSTRACT

Devices, systems, and methods are disclosed that help deliver catheters or other medical devices to locations within a patient's body. The device includes a transporter catheter having a proximal end and a distal end, at least a first balloon located adjacent to the distal end, and at least a second balloon located between the first balloon and the proximal
(Continued)

end of the transporter catheter. The first balloon is configured for holding a prosthetic device in place. In another embodiment, the transporter catheter has a third balloon, an orienting balloon, substantially at the tip of the distal end of the transporter catheter.

19 Claims, 47 Drawing Sheets

Related U.S. Application Data application No. 17/064,704, filed on Oct. 7, 2020, now Pat. No. 10,994,105, which is a continuation of application No. 17/001,678, filed on Aug. 24, 2020, now Pat. No. 10,828,470, which is a continuation-in-part of application No. 16/888,219, filed on May 29, 2020, now Pat. No. 10,821,267, which is a continuation-in-part of application No. 16/721,909, filed on Dec. 19, 2019, now Pat. No. 10,773,059, which is a continuation-in-part of application No. 16/701,966, filed on Dec. 3, 2019, now Pat. No. 10,773,058.

(60) Provisional application No. 62/886,349, filed on Aug. 14, 2019.

(52) U.S. Cl.
CPC ..... *A61M 25/1002* (2013.01); *A61M 25/0102* (2013.01); *A61M 25/0116* (2013.01); *A61M 2025/015* (2013.01); *A61M 2025/1088* (2013.01)

(56) References Cited

U.S. PATENT DOCUMENTS

| | | |
|---|---|---|
| 4,757,827 A | 7/1988 | Buchbinder et al. |
| 5,167,221 A | 12/1992 | Chikama |
| 5,271,415 A | 12/1993 | Foerster et al. |
| 5,395,329 A | 3/1995 | Fleischhacker et al. |
| 5,441,483 A | 8/1995 | Avitall |
| 5,456,664 A | 10/1995 | Heinzelman et al. |
| 5,472,017 A | 12/1995 | Kovalcheck |
| 5,637,086 A | 6/1997 | Ferguson et al. |
| 5,827,278 A | 10/1998 | Webster |
| 5,876,375 A | 3/1999 | Penny |
| 5,906,606 A | 5/1999 | Chee et al. |
| 6,027,462 A | 2/2000 | Greene et al. |
| 6,143,013 A | 11/2000 | Samson et al. |
| 6,146,338 A | 11/2000 | Gardeski et al. |
| 6,179,809 B1 | 1/2001 | Khairkhahan et al. |
| 6,190,333 B1 | 2/2001 | Valencia |
| 6,394,976 B1 | 5/2002 | Winston et al. |
| 6,432,112 B2 | 8/2002 | Brock et al. |
| 6,450,948 B1 | 9/2002 | Matsuura et al. |
| 6,485,455 B1 | 11/2002 | Thompson |
| 6,530,897 B2 | 3/2003 | Nardeo |
| 6,533,783 B1 | 3/2003 | Tollner |
| 6,582,536 B2 | 6/2003 | Shimada |
| 6,607,496 B1 | 8/2003 | Poor et al. |
| 6,991,616 B2 | 1/2006 | Bencini et al. |
| 7,077,823 B2 | 7/2006 | McDaniel |
| 7,331,980 B2 | 2/2008 | Dubrul et al. |
| 7,377,906 B2 | 5/2008 | Selkee |
| 7,494,478 B2 | 2/2009 | Itou et al. |
| 7,691,095 B2 | 4/2010 | Bednarek et al. |
| 7,766,868 B2 | 8/2010 | Goode et al. |
| 7,914,515 B2 | 3/2011 | Heideman et al. |
| 8,206,371 B2 | 6/2012 | Nimkar et al. |
| 8,292,850 B2 | 10/2012 | Root et al. |
| 8,313,478 B2 | 11/2012 | Tockman et al. |
| 8,313,493 B2 | 11/2012 | Fischer |
| 8,323,239 B2 | 12/2012 | Bednarek et al. |
| 8,603,066 B2 | 12/2013 | Heideman et al. |
| 8,702,625 B2 | 4/2014 | Ayala et al. |
| 8,734,699 B2 | 5/2014 | Heideman et al. |
| 8,747,428 B2 | 6/2014 | Fischell et al. |
| 8,814,825 B2 | 8/2014 | Tegg et al. |
| 8,858,528 B2 | 10/2014 | Sicvol |
| 8,926,560 B2 | 1/2015 | Dinh et al. |
| 9,119,738 B2 | 9/2015 | Fish |
| 9,259,813 B2 | 2/2016 | Heideman et al. |
| 9,320,503 B2 | 4/2016 | Bolduc |
| 9,492,636 B2 | 11/2016 | Heideman et al. |
| 9,681,882 B2 | 6/2017 | Garrison |
| 9,763,784 B2 | 9/2017 | Bielefeld |
| 9,764,118 B2 | 9/2017 | Anderson et al. |
| 9,788,943 B2 | 10/2017 | Deshmukh et al. |
| 9,987,463 B2 | 6/2018 | Guo et al. |
| 10,004,877 B2 | 6/2018 | Tegg |
| 10,035,000 B2 | 7/2018 | Bednarek et al. |
| 10,058,677 B2 | 8/2018 | Kawase |
| 10,099,036 B2 | 10/2018 | Heideman et al. |
| 10,130,791 B2 | 11/2018 | Heideman et al. |
| 10,182,841 B1 | 1/2019 | Rousu et al. |
| 10,194,905 B2 | 2/2019 | Bolduc et al. |
| 10,478,296 B2 | 11/2019 | Le et al. |
| 10,517,721 B2 | 12/2019 | Taylor |
| 10,653,862 B2 | 5/2020 | Winston et al. |
| 2002/0013580 A1 | 1/2002 | Houser |
| 2002/0026145 A1 | 2/2002 | Bagaoisan et al. |
| 2002/0087156 A1 | 7/2002 | Maguire et al. |
| 2002/0111649 A1 | 8/2002 | Russo et al. |
| 2002/0165598 A1 | 11/2002 | Wahr et al. |
| 2003/0004541 A1 | 1/2003 | Linder et al. |
| 2003/0105451 A1 | 6/2003 | Westlund et al. |
| 2003/0149467 A1 | 8/2003 | Linder et al. |
| 2003/0199963 A1 | 10/2003 | Tower et al. |
| 2004/0002706 A1 | 1/2004 | Houser |
| 2004/0064179 A1 | 4/2004 | Linder et al. |
| 2004/0073158 A1 | 4/2004 | Shah et al. |
| 2004/0143256 A1 | 7/2004 | Bednarek |
| 2004/0193055 A1 | 9/2004 | Field et al. |
| 2004/0220549 A1 | 11/2004 | Dittman et al. |
| 2005/0059965 A1 | 3/2005 | Eberl et al. |
| 2005/0107737 A1 | 5/2005 | McDaniel |
| 2005/0288700 A1 | 12/2005 | Chermoni |
| 2006/0106375 A1 | 5/2006 | Werneth et al. |
| 2006/0241564 A1 | 10/2006 | Corcoran et al. |
| 2007/0005008 A1 | 1/2007 | Honebrink et al. |
| 2007/0005131 A1 | 1/2007 | Taylor |
| 2007/0112369 A1 | 5/2007 | Crossman |
| 2007/0173757 A1 | 7/2007 | Levine et al. |
| 2007/0225677 A1 | 9/2007 | Rowe et al. |
| 2007/0270679 A1 | 11/2007 | Nguyen |
| 2008/0183128 A1 | 7/2008 | Morriss et al. |
| 2008/0281228 A1 | 11/2008 | Parodi et al. |
| 2009/0062602 A1 | 3/2009 | Rosenberg et al. |
| 2011/0301502 A1 | 12/2011 | Gill |
| 2012/0053419 A1 | 3/2012 | Bloom |
| 2012/0116353 A1 | 5/2012 | Arnold et al. |
| 2012/0157913 A1 | 6/2012 | Aziz et al. |
| 2013/0237962 A1 | 9/2013 | Kawai |
| 2014/0005647 A1 | 1/2014 | Shuffler et al. |
| 2014/0058251 A1 | 2/2014 | Stigall et al. |
| 2014/0155980 A1 | 6/2014 | Turjman et al. |
| 2014/0180086 A1 | 6/2014 | Jang et al. |
| 2014/0276618 A1 | 9/2014 | Di Caprio et al. |
| 2015/0051634 A1 | 2/2015 | Kravik et al. |
| 2015/0196740 A1 | 7/2015 | Mallin et al. |
| 2015/0265806 A1 | 9/2015 | Kawaguchi |
| 2015/0265812 A1 | 9/2015 | Lalonde et al. |
| 2016/0051799 A1 | 2/2016 | Daniels et al. |
| 2016/0114126 A1 | 4/2016 | Heideman et al. |
| 2016/0249942 A1 | 9/2016 | Olson |
| 2016/0346515 A1 | 12/2016 | Buller et al. |
| 2016/0361058 A1 | 12/2016 | Bolduc et al. |
| 2017/0028170 A1 | 2/2017 | Ho |
| 2019/0255297 A1 | 8/2019 | Fischell et al. |

(56) References Cited

U.S. PATENT DOCUMENTS

2019/0255299 A1    8/2019   Fischell et al.
2020/0085483 A1    3/2020   Tegg et al.

FOREIGN PATENT DOCUMENTS

| EP | 2670355 B1 | 11/2016 |
| EP | 2349086 B1 | 3/2017 |
| EP | 2869882 B1 | 2/2018 |
| JP | 2000033122 A | 2/2000 |
| WO | WO2000067834 A1 | 11/2000 |
| WO | WO 02/05868 A2 | 1/2002 |

OTHER PUBLICATIONS

Tejas Patel, et al, "Balloon-Assisted Tracking: A Must Know Technique to Overcome Difficult Anatomy During Transradial Approach" Cath and Cardiovasc Intervent. 83:E211-20(2014).

International Search Report in International application No. PCT/US 20/29999.

Written Opinion of the International Searching Authority in International application No. PCT/US 20/29999.

Search History in International application No. PCT/US 20/29999.

Search History in International application No. PCT/US2020/041743.

Written Opinion of the International Searching Authority in International application No. PCT/US2020/041743.

International Search Report in International application No. PCT/US2020/041743.

Extended European Search Report EESR Application No. EP 20 17 2795.

International Search Report in International application No. PCT/US 21/47186.

Written Opinion of the International Searching Authority in International application No. PCT/US 21/47186.

Search History in International application No. PCT/US 21/47186.

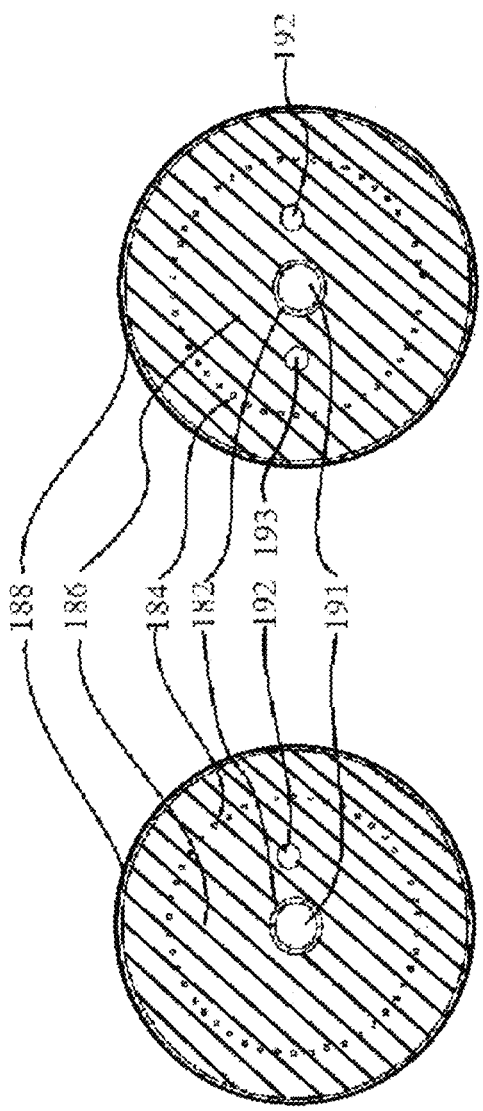
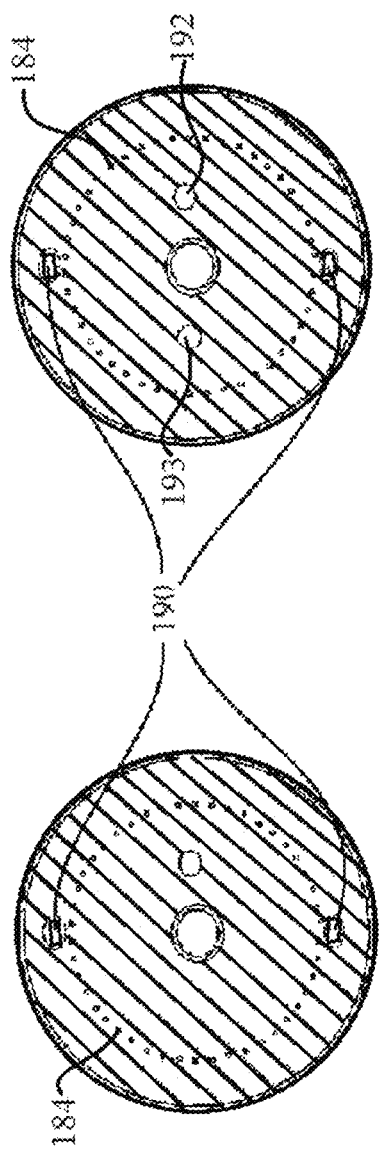
FIG. 18a  FIG. 18b  FIG. 18c  FIG. 18d

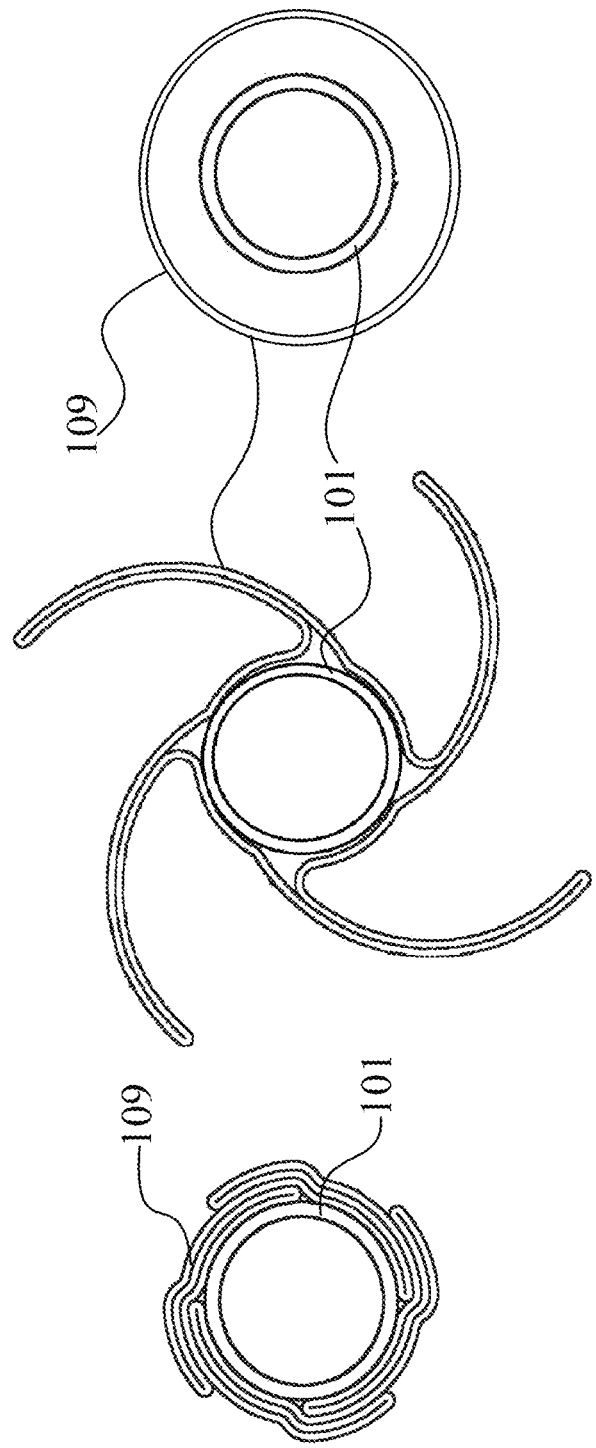

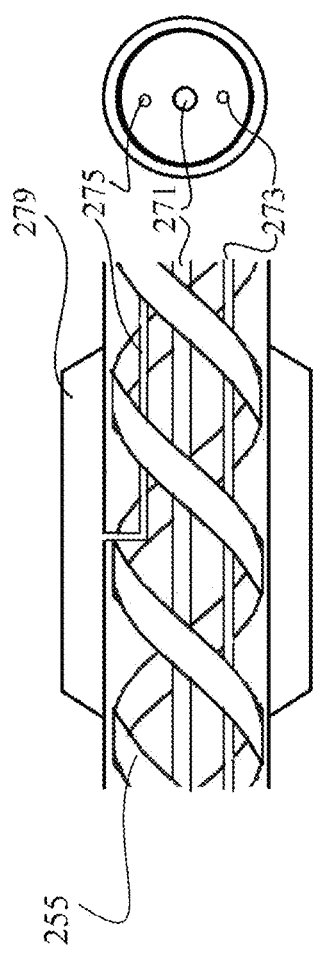
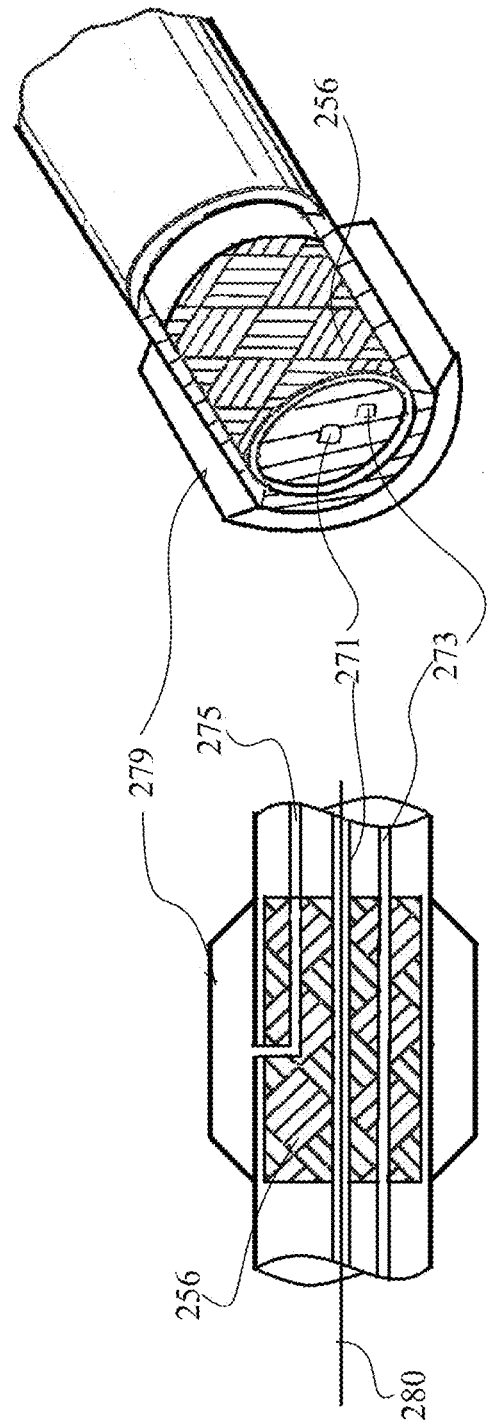
FIG. 25a
FIG. 25b

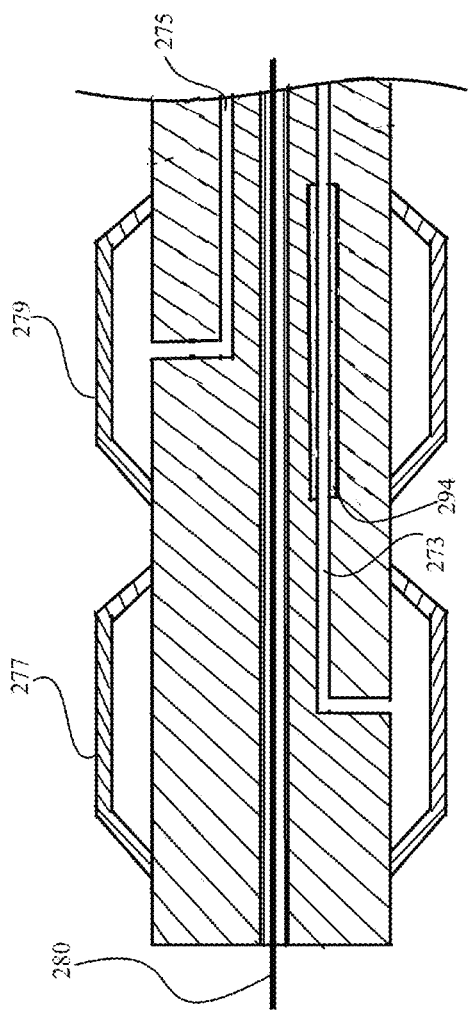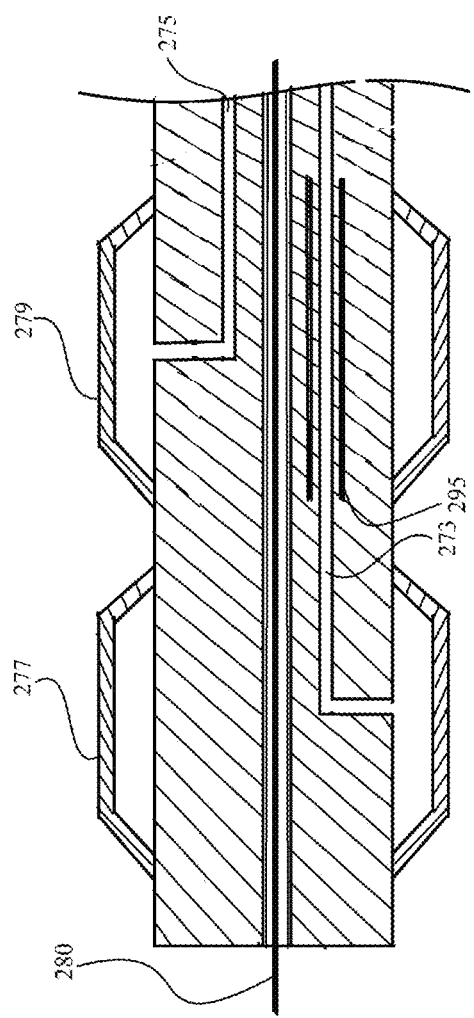
FIG. 26a
FIG. 26b

APPARATUS AND METHOD FOR ADVANCING CATHETERS OR OTHER MEDICAL DEVICES THROUGH A LUMEN

CROSS-REFERENCE TO RELATED APPLICATIONS

This application is a 371 of international application PCT/US21/47186, with international filing date Aug. 23, 2021 and priority date Aug. 24, 2020, which is a continuation-in-part of U.S. patent application Ser. No. 17/221,448, filed Apr. 2, 2021, which is a continuation-in-part of U.S. patent application Ser. No. 17/064,704, filed Oct. 7, 2020, now U.S. Pat. No. 10,994,105, issued on May 4, 2021, which is a continuation of U.S. patent application Ser. No. 17/001,678, filed Aug. 24, 2020, now U.S. Pat. No. 10,828,470, issued on Nov. 10, 2020, and claims benefit of U.S. Provisional Application No. 63/112,474, filed Nov. 11, 2020; the entire content of the above applications is incorporated herein by reference.

FIELD OF THE INVENTION

The invention relates generally to devices, systems, and methods that help deliver catheters or other medical devices to locations within a patient's body. More particularly, the present invention is directed to a transporter catheter, which is located inside an outer catheter, e.g., a sheath, an introducer catheter, a guide catheter or an inner catheter. An orienting balloon at a tip of the transporter catheter assists in the orientation and positioning of the transporter catheter, and an anchoring balloon is used for anchoring the transporter catheter, e.g., anchoring the transporter catheter to an inner surface of a sheath or an introducer catheter or a guiding catheter or an inner catheter as the user maneuvers the system comprising the transporter catheter and the sheath or the introducer catheter or the guiding catheter through the patient's body.

BACKGROUND OF THE INVENTION

Catheters are used for an ever-growing number of medical procedures including diagnostic and/or therapeutic procedures. To facilitate placement of the diagnostic and/or therapeutic catheter at a location of interest within a patient, a catheter may be introduced through a second catheter, which is commonly known as a "sheath" or "introducer catheter," and these two terms will be used interchangeably herein. A system of catheters is commonly known as "catheter system" or "delivery system" or "treatment system," and these terms will be used interchangeably herein. An introducer catheter is a tube that is used to facilitate the placement of other catheters into specific areas of the patient's body. In the field of cardiac ablation, for example, introducer catheters may be used to negotiate the patient's vasculature such that an ablation device may be passed through and positioned to be able to ablate arrhythmia-causing cardiac tissue. The introducer catheter itself may be advanced over a guidewire.

Complex coronary anatomy including tortuosity, calcification, as well as other structural characteristics of the coronary artery can make transit of hardware through the lumen proximal to a stenosis difficult and sometimes impossible. Several advancements in technology such as stiffer guidewires, large bore guide catheters that allow for improved passive support, and hydrophilic coatings that provide reduced friction, have improved the ability to advance balloons and stents through these coronary arteries with some success. Guidewires that allow for dynamic deflection of the tip such as the "Wiggle" wire have also improved hardware transit. However, even with these advances, in view of the expanding indications for percutaneous coronary intervention ("PCI"), there is an unmet need for improving PCI outcomes in complex substrates.

A guide catheter may be located inside an introducer catheter, and an inner support catheter ("daughter" or "child" catheter) placed inside a guide catheter. Advancing the inner support catheter into the coronary artery deeply intubating the proximal coronary-artery lumen has been shown to improve support of the guide catheter and inner catheter composite system, thereby providing an opportunity for improved success for device advancement through a difficult coronary lumen (Guideliner, Guidezilla, Telescope). Frequently, these inner catheters are only able to navigate the proximal simpler portions of the artery anatomy, and do not allow the operator to obtain a position in the artery lumen that provides sufficient support to the guide catheter and inner catheter composite system. The inability to advance these inner catheters further into a patient's vasculature is frequently as a result of the "razor effect" caused by an overhang or transitions between the guidewire and the inner-support catheter.

Generally, it is known that the introducer catheter must have an overall diameter small enough to negotiate through a lumen of a vessel while retaining an inner diameter (or "bore size") large enough to accommodate a diagnostic, a therapeutic and/or an ablation device therethrough. Furthermore, since the path within a patient's vessel is often long and tortuous, steering forces must be transmitted over relatively long distances. Accordingly, it is desirable for the introducer catheter to have enough axial strength to be pushed through the patient's vasculature via a force applied at its proximal end ("pushability"). It is also desirable for the introducer catheter to be capable of transmitting a torque applied at the proximal end through to the distal end ("torqueability"). An introducer catheter should also have enough flexibility to conform substantially to the patient's vasculature and yet resist kinking as it conforms to the patient's vasculature. These various characteristics are often in conflict with one another, with improvements in one often requiring compromises in others. For example, increasing the bore size of an introducer catheter having a given overall diameter requires utilizing a thinner wall. As catheters are used in smaller and smaller passages and vessels, there is a growing need to use introducer catheters that have a smaller outer dimension. However, a thin-walled introducer catheter is more likely to collapse upon itself or kink when a torque or a push force is applied at its proximal end.

In order to facilitate the advancement of an introducer catheter (or an introducer sheath) through a patient's vasculature, the application of a push force and/or torque at the proximal end of the introducer catheter and the ability to orient selectively the distal tip of the introducer catheter in a desired direction can permit medical personnel to advance the distal end of the catheter and to position the distal portion of the introducer catheter at a location of interest.

During use, an introducer catheter shaft should be capable of transmitting torque and resisting compression. Substantial frictional forces sometimes resist transmission of axial forces and torque along the length of the introducer catheter. In some cases, these forces may cause the introducer catheter shaft to twist about a longitudinal axis of the introducer catheter shaft, storing energy in the process in a spring-like fashion. If such energy is released suddenly, the distal end of the introducer catheter, which may have been deflected by a steering mechanism, may be undesirably propelled with significant force.

With respect to resisting compression during use, it is important that users be able to advance the introducer catheter through a vessel, sometimes against significant frictional resistance, without undue axial or radial compression or snaking or fish-mouth distortion of the introducer catheter shaft. Shaft compression may complicate the positioning of the distal end of the introducer catheter shaft at a desired location for a medical procedure. In addition, medical personnel may rely on tactile feedback to attain and verify proper positioning of the introducer catheter, and such feedback can be impaired by excessive compressibility.

Accordingly, there is a need for improved devices, systems and methods to deliver an introducer catheter or a sheath or a guide catheter or an inner catheter at a location of interest within a patient's body via a body lumen without damaging the lumen, or a body vessel, including a tortuous lumen or vessel. The foregoing discussion is intended only to illustrate the present field and should not be taken as a disavowal or limitation of claim scope.

SUMMARY OF THE INVENTION

The devices, systems, and methods for negotiating a patient's vasculature through lumens or vessels are described herein. In particular, the present invention provides improved devices, systems, and methods for procedures including diagnostic, therapeutic, and ablative procedures in arterial and venous systems, as well as for non-vascular lumen and vessel. A catheter system of the present invention comprises a transporter catheter and an introducer catheter. In an exemplary embodiment, a balloon at a distal tip of a transporter catheter facilitates the negotiation of the transporter catheter and/or associated device or system through the body lumens of a patient. The transporter catheter may have at least one anchoring balloon that anchors the transporter catheter to the introducer catheter. The anchoring balloon prevents partially or fully the slippage or "pushback" of the transporter catheter backwards into the lumen of the introducer catheter when the orienting balloon of the transporter catheter experiences increased resistance within the vasculature in the patient's body. Also, when the anchoring balloon is located proximate to the orienting balloon, the anchoring balloon acts as a stopper to prevent the orienting balloon from backing into the lumen of the introducer catheter as the catheter system is being maneuvered through the vasculature of the patient's body. It also prevents the orienting balloon from migrating fully out of the introducer catheter, guide catheter or inner catheter when forward force is applied to the catheter system. In the description of the invention, the transporter catheter is described as being located inside the introducer catheter. The transporter catheter may also be located inside any outer catheter, e.g., a sheath, a mother catheter, a guiding catheter or a daughter catheter, to advance the outer catheter. An orienting balloon at a tip of the transporter catheter assists in the orientation and positioning of the transporter catheter, and an anchoring balloon is used for anchoring the transporter catheter, e.g., anchoring the transporter catheter to an inner surface of an outer catheter as the user maneuvers the system comprising the transporter catheter and the outer catheter through the patient's vasculature. The description and discussion regarding advancing the introducer catheter also applies to advancing any other outer catheter through a patient's vasculature using a transporter catheter.

The catheter system of the present invention may be advanced through the vasculature of a patient's body by (a) pushing and/or torqueing the introducer catheter, (b) pushing and/or torqueing the transporter catheter, or (c) pushing and/or torqueing both the introducer catheter and the transporter catheter. If the user pushes and/or torques the introducer catheter to advance the catheter system through the vasculature of the patient's body, then the anchoring balloon of the transporter catheter pushes and/or torques the transporter catheter as the catheter system moves through the vasculature of the patient's body. If the user pushes and/or torques the transporter catheter to advance the catheter system through the vasculature of the patient's body, the anchoring balloon of the transporter catheter pulls and/or torques the introducer catheter as the catheter system moves through the vasculature of the patient's body. In both cases, the orienting balloon assists in orienting and maneuvering the catheter system through the vasculature of the patient's body.

An embodiment of the invention provides devices, systems, and methods including a transporter catheter comprising a first tube having a length and defining a first open interior lumen, the first open interior lumen connected to a first balloon located at a distal end of the transporter catheter, a second tube having a length and defining a second open interior lumen, the second open interior lumen connected to a second balloon located between the first balloon and the proximate end of the transporter catheter. In another embodiment, the second balloon is proximate to the first balloon. In yet another embodiment, the distance between the proximal end of the first balloon and the distal end of the second balloon is less than half the length of the fully inflated first balloon. In another embodiment, the distance between the proximal end of the first balloon and the distal end of the second balloon is less than half the diameter of the fully inflated first balloon. In one embodiment, the orienting balloon has length in the range from 15-40 mm. In another embodiment, the orienting balloon expands to diameters ranging from 1.5-6 mm after inflation. In yet another embodiment, the orienting balloon expands to diameters in the range of 6-12 mm upon inflation. In another embodiment, the orienting balloon expands to diameters in the range of 12-18 mm upon inflation. In one embodiment, a balloon is fully inflated when the volume of fluid introduced in the balloon is at least the same as the specified design volume of the balloon. In another embodiment, the balloon is fully inflated when the balloon has expanded to reach its maximum structural dimensions, e.g., diameter and length. In another embodiment, a balloon is fully inflated when, upon introduction of fluid, the balloon expands to engage an inner wall of a tube or a catheter within which the balloon may be located, the inner wall of the tube or the catheter preventing further expansion of the balloon. In yet another embodiment, a balloon is fully inflated when, upon introduction of fluid, the balloon expands to engage an inner wall of a lumen or a vessel in a patient's body wherein the balloon may be located.

In one embodiment of the invention, the device comprises a transporter catheter having a proximal end and a distal end, at least a first balloon located at the distal end, substantially at a tip of the transporter catheter, and at least a second balloon located between the distal end and the proximal end of the transporter catheter. The first balloon is an orienting balloon, and the second balloon is an anchoring balloon. The transporter catheter may include a single lumen or more than one lumen. In one embodiment, the shaft of the transporter catheter may be made from a polymer such as polytetrafluoroethylene (PTFE) or PEBAX (polyether block amide). In another embodiment, the shaft of the transporter catheter may comprise a wire-based reinforcement embedded in the polymeric shaft. In another embodiment, the shaft of the transporter catheter may comprise an inner layer and an outer layer. In one embodiment, the inner layer may be made of a material more flexible than the material of the outer layer. In another embodiment, the outer layer comprises a material that has a lower flexural modulus and a higher-yield strain than the material of the inner layer. In one embodiment, the outer layer may comprise braided-wire assembly, said braided-wire assembly being formed by braiding a plurality of flat wires or circular wires. The shaft of the transporter catheter may comprise a plurality of segments of varying hardness characteristics. The hardness of the first segment of the shaft of the transporter catheter located between the orienting balloon and the anchoring balloon may be less than the hardness of the second segment of the shaft between the anchoring balloon and the proximal end of the catheter. In another embodiment, the hardness of a portion of the first segment of the shaft proximate to the orienting balloon may be less than the hardness of a portion of the first segment of the shaft proximate to the anchoring balloon.

Another embodiment of the invention provides devices, systems, and methods that comprise an introducer catheter that has a capability to maneuver through the vasculature of a patient's body independently from the transporter catheter. Such introducer catheters are generally known as "steerable-guide" catheters. One embodiment of the steerable-guide catheter comprises at least a first handle assembly comprising a first deflecting mechanism coupled to a distal end portion of the steerable-guide catheter to apply a deflecting force to bend the distal end portion, the first deflecting mechanism adapted to bend the distal end portion in a first articulated position, and a second deflecting mechanism coupled to the distal end portion of the steerable-guide catheter to apply a deflecting force to bend the distal end portion, the second deflecting mechanism adapted to bend the distal end portion in a second articulated position. The steerable-guide catheter further comprises at least an open interior lumen to accommodate passage of a transporter catheter to assist in the orientation and positioning of the steerable catheter. The transporter catheter located inside the steerable-guide catheter assists in orienting and positioning the steerable catheter and compliments the functioning of the deflecting mechanisms to advance the steerable catheter smoothly. After the steerable-guide catheter is positioned at the desired location, the orienting balloon and the anchoring balloon in the transporter catheter are deflated and the transporter catheter is removed from the interior lumen of the steerable-guide catheter.

BRIEF DESCRIPTION OF THE DRAWINGS

FIG. 18a-d illustrate cross-sectional views of shaft of some embodiments of a transporter catheter.

FIG. 20 is a perspective view of a balloon having pleats to facilitate rewrapping of the balloon upon deflation of the balloon.

FIG. 25a-b depict sectional views of the shaft of the transporter catheter illustrating reinforcement of the shaft underlying at least the anchoring balloon.

FIG. 26a-b depict perspective sectional views of the shaft of the transporter catheter illustrating reinforcements underlying the anchoring balloon to prevent pinching of the lumen connected to the orienting balloon.

DETAILED DESCRIPTION OF THE INVENTION

Embodiments of the present invention are described below with reference to the accompanying drawings. Systems using transporter catheters according to the present invention provide improved maneuverability, flexibility, and kink resistance.

Figure 1:
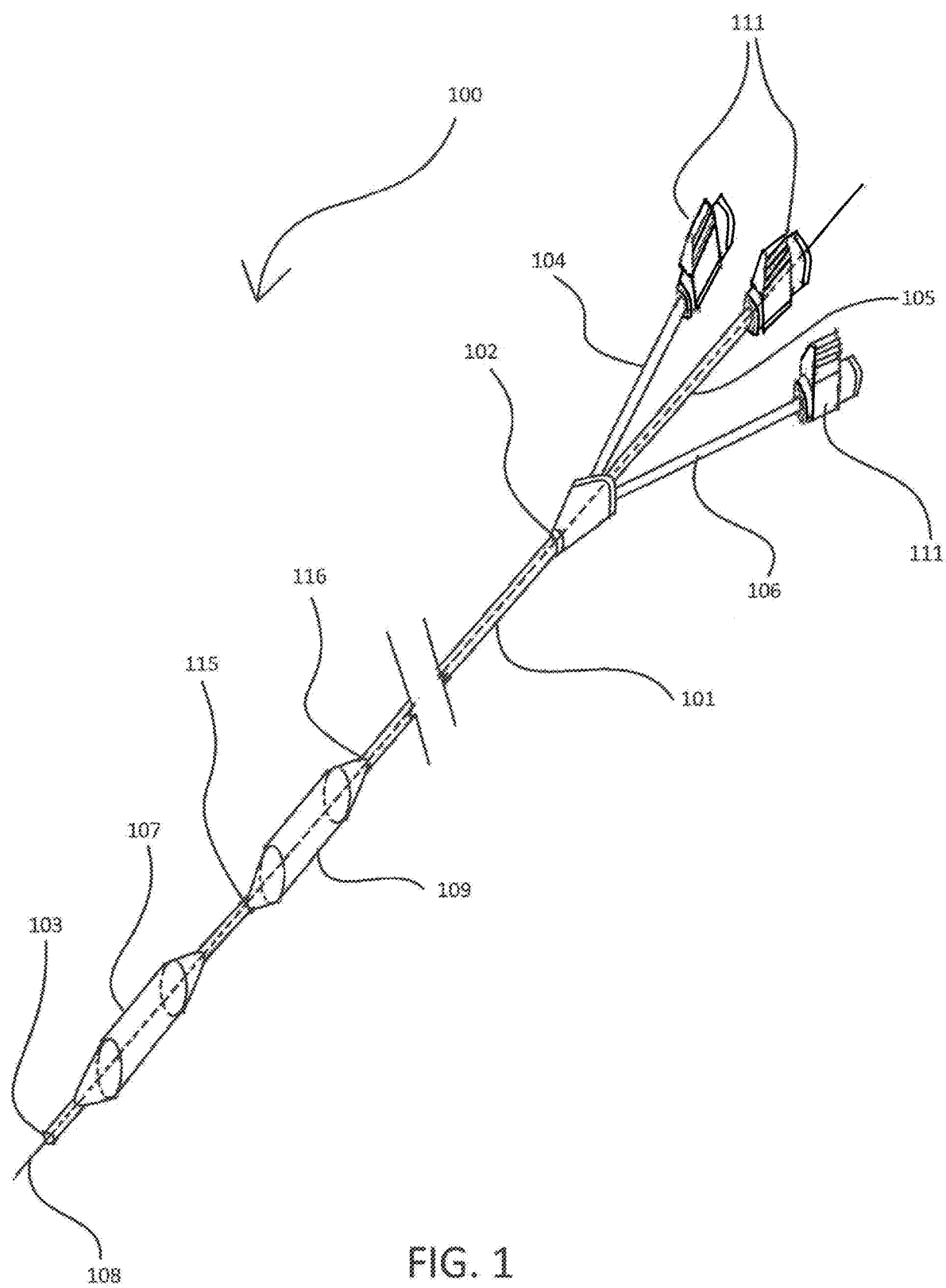
FIG. 1 is a perspective view of a transporter catheter in accordance with one embodiment of the present invention.

In reference to FIG. 1, catheter 100, comprises a shaft 101, having a proximal end 102, and a distal end 103, and a first lumen 104, a second lumen 105, and a third lumen 106. First lumen 104 extends substantially the entire length of said shaft 101 and communicates with an orienting balloon 107 located at about the distal end 103 of said shaft 101. Second lumen 105 extends the entire length of said shaft 101 and allows for the placement of catheter 100 over guidewire 108. Third lumen 106 communicates with an anchoring balloon 109, which is located between the orienting balloon 107 and the proximal end 102 of the shaft 101. In one embodiment, the anchoring balloon is located proximal to the orienting balloon. In another embodiment, the first lumen 104 and the third lumen 106 are diametrically opposed and each lumen extends substantially parallel to the longitudinal axis of the shaft 101. In another embodiment, the first lumen 104 and the third lumen 106 are symmetrically disposed on either side of a longitudinally extending plane bisecting the shaft into a first hemicylindrical portion and a second hemicylindrical portion.

In another embodiment, the third lumen 106 communicating with the anchoring balloon may be adapted to receive a removable stiffening stylet to ease insertion by stiffening the catheter shaft. In yet another embodiment, two removable stiffening stylets may be inserted, one inserted in lumen 104 and another inserted in lumen 106. Stiffening stylet(s) are inserted to extend substantially the entire length of member 101 until just proximal to anchoring balloon 109. If two stylets are used, the practitioner may insert one stylet further than the other to adjust the amount of stiffness as desired. In one embodiment, a stylet is not inserted beyond the anchoring balloon. In another embodiment, the shaft 101 may comprise a stylet lumen dedicated and adapted to receive a removable stiffening stylet. In one embodiment, the stylet lumen may extend from the proximal end 102 to the distal end 115 of the anchoring balloon 109.

Lumens 104, 105 and 106 are attached to Luer connectors 111 at their proximal end. Said Luer connectors are then connected to syringes, valves etc. to provide for the introduction of balloon inflation media. In one embodiment, a radiopaque marker may be located along shaft 101, including distal end 103. In another embodiment, a radiopaque marker may be located on the anchoring balloon 109. In one embodiment, an imaging marker is fixed to shaft 101 at its distal end portion, disposed slightly proximal from the tip 103 and in the area proximate to a front-end portion of the orienting balloon 107. In another embodiment, the imaging marker is fixed on the orienting balloon 107. In yet another embodiment, the imaging marker is fixed on the anchoring balloon 109. In one embodiment, the imaging marker is formed from a radiopaque material (e.g., gold, platinum, tungsten or alloys of these metals or from a silver-palladium alloy, or a platinum-iridium alloy). By so doing, it is possible to confirm the location of the catheter and then to advance the catheter 100 through a patient's vasculature, while monitoring such advancement using radiographic imaging and visualization. In one embodiment, the shaft of the transporter catheter may have a lumen from its proximal end to its distal end to infuse medication at the distal end by using a Luer connector at the proximal end.

The mechanical properties of segments of shaft 101 can be varied by adjusting and varying the properties of the cylindrical-braid structure(s) and the polymeric materials (e.g., the dimension of the cylindrical-braid structure and/or durometers of the polymers). Additionally, the mechanical properties of the segments of shaft 101 can be varied along the length of the shaft 101 in accordance with certain embodiments of the disclosure or can be substantially uniform along the entire length of the shaft 101 in accordance with other embodiments of the disclosure. In another embodiment, the shaft 101 is a monolithic elongate tubular shaft member having an inner core made of a first material and an outer layer made of a second material, the first material of the inner core defining lumens 104, 105 and 106 therein, the cross-sectional dimension of the first lumen 104 being uniform along the length of the first lumen 104, the cross-sectional dimension of the second lumen 105 being uniform along the length of the second lumen 105, and the cross-sectional dimension of the third lumen 106 being uniform along the length of the third lumen 106. In one embodiment, the tubular shaft member has an outer cross-sectional dimension that varies along the length of the tubular shaft member, the outer cross-sectional dimension being greater at the proximal end than at the distal end.

Figure 2:
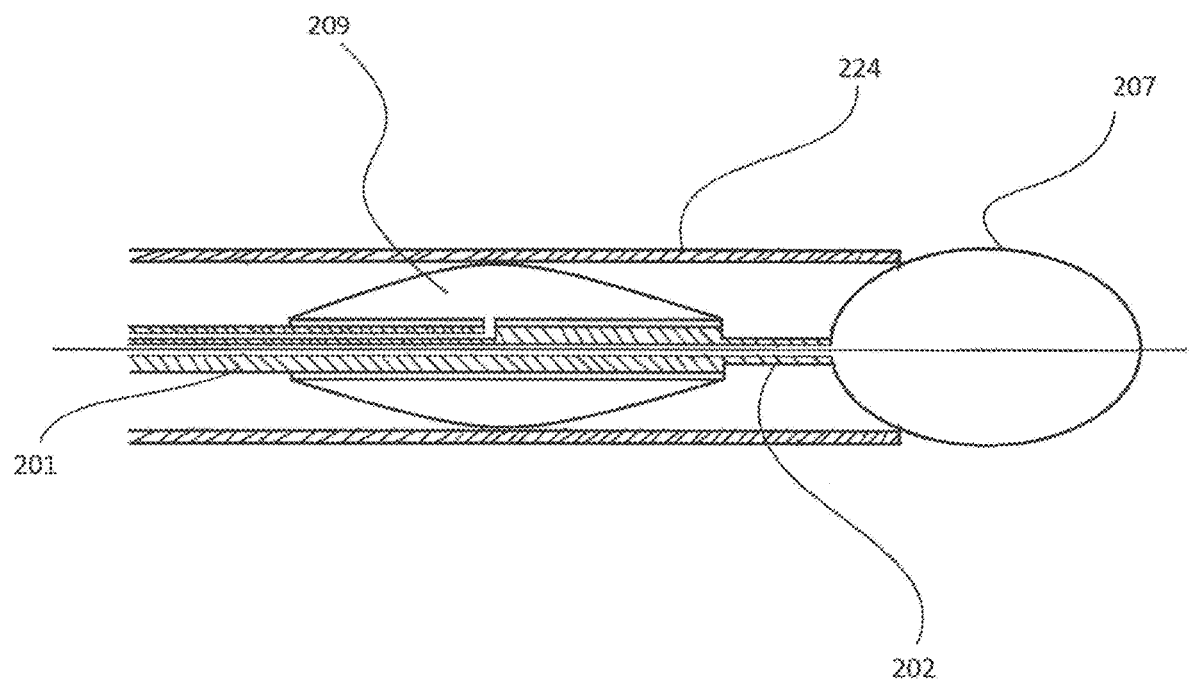
FIG. 2 illustrates a sectional view of a transporter catheter having a first segment of the transporter catheter that is more flexible than a second segment of the transporter catheter.

In one embodiment, the shaft 101 may be provided with a rigidity-imparting structure. In one embodiment, the rigidity-imparting structure is provided using a blade. The blade may be formed of a metal wire or a synthetic-resin wire. In another embodiment, as shown in FIG. 2, the rigidity-imparting structure is provided to the shaft over the entire length 201 of the shaft, except for the distal end portion 202 of the shaft from the anchoring balloon 209 to the orienting balloon 207. The anchoring balloon 209 anchors the rigidity-imparted structure 201 to the inner surface of a lumen of the introducer catheter 224. In another embodiment, the rigidity-imparting structure is provided to the shaft 101 in a range from the proximal end 102 of the transporter catheter to the distal end 115 of the anchoring balloon 109. In one embodiment, the shaft of the transporter catheter has a stiffness and a resistance to kinking. In another embodiment, the shaft of the transporter catheter comprises an inner layer made preferably of a lubricious material, such as polytetrafluoroethylene (PTFE), and an outer layer made preferably of a thermoplastic elastomer, such as PEBAX (polyether block amide). In another embodiment, the inner and the outer layers are made of two different melt-processable polymers. In another embodiment, the shaft of the transporter catheter may comprise more than two layers. In another embodiment, the shaft of the transporter catheter may comprise a single polymeric material. In one embodiment, the shaft of the transporter catheter may comprise a single first polymeric material for a first length of the shaft and a single second polymeric material for a second length of the shaft. In another embodiment, the shaft of the transporter catheter may comprise a single first polymeric material for a first length of the shaft from the proximal end 102 of the shaft to the distal end 115 of the anchoring balloon 109, and a single second polymeric material for a second length of the shaft from the distal end 115 of the anchoring balloon 109 to the distal end 103 of the shaft. In one embodiment, the hardness of the first polymeric material of the first length of the shaft may be greater than the hardness of the second polymeric material of the second length of the shaft. In another embodiment, the inner and/or the outer layer comprises a particulate radiopaque filler material. In another embodiment, the outer surface of the shaft of the transporter catheter may have at least one radiopaque strip along the length of the shaft and/or radiopaque markers at specific locations of the shaft, e.g., at the distal end of the transporter catheter.

In one embodiment, a wire-based reinforcement is embedded in the outer layer. The wire-based reinforcement may be in the form of a plait matrix or a helical coil. The plait matrix may be braided. The plait-matrix layer or the helical-coil layer may be bonded to the inner layer e.g., by melting in place. In one embodiment, a plait-matrix layer or a helical-coil layer is bonded to the inner layer by melting in place using a temporary shrink-wrap tubing as a forming member. The plait-matrix layer or the helical-coil layer may also be known as the torque-transfer layer. In another embodiment, the shaft comprises a plurality of sections with wire reinforcement in a form of a plait-matrix or a helical-coil layer extending continuously along at least one length from the proximal end 102 of the shaft. In another embodiment, the shaft comprises a plurality of sections with the plait-matrix layer or the helical-coil layer extending continuously from the proximal end 102 of the shaft to the distal end 115 of the anchoring balloon 109. In another embodiment, the shaft comprises a plurality of sections with the plait-matrix layer or the helical-coil layer extending continuously from the proximal end 102 of the shaft to the proximal end of the orienting balloon 107. In another embodiment, the shaft 101 comprises a plurality of sections with the plait-matrix layer or the helical-coil layer extending continuously from the proximal end 102 of the shaft to the distal end of the orienting balloon 107. In another embodiment, the plait-matrix layer or the helical-coil layer extends continuously the entire length of the shaft 101 from the proximal end 102 to the distal end 103. In one embodiment, the distal portion 202 of the shaft is more flexible than the outer catheter 224. In another embodiment, the proximal portion 201 of the shaft is more rigid than the outer catheter 224. In one embodiment, the rigidity of the distal portion of the outer catheter is greater than or same as the rigidity of the distal portion of the shaft of the transporter catheter, and the rigidity of the proximal portion of the outer catheter is less than or same as the rigidity of the proximal portion of the shaft of the transporter catheter.

The plait matrix or the helical coil may be made of round wires, elliptical wires, flat wires or combination thereof. Wires of any other cross-sectional shapes may also be used. The wires may be made from various materials and may each be made of the same materials or materials with similar material properties, or different materials having different properties. As an example, such wires may be formed from stainless steel. The material of wires may be stiffer than the plastic materials forming the wall of the shaft. In one embodiment, the flat wire is at least about 0.003" thick by about 0.007" wide. In another embodiment, the wires may be made of Nitinol. In one embodiment, the braided-wire plait matrix has a proximal portion and a distal portion, the braided-wire plait matrix has a first density at the proximal portion and a second density at the distal portion, and wherein the first density differs from the second density, the density of the braided-wire assembly being measured in pixels of braids per inch of the shaft's longitudinal axis (PPI). In another embodiment, the PPI at the proximal portion of the braided-wire plait matrix is greater than the PPI at the distal portion of the braided-wire plait matrix. In another embodiment, the PPI is between about 10 and about 90. In yet another embodiment, the PPI is between about 5 and about 50. In another embodiment, the shaft of the transporter catheter comprises braided-wire plait matrix, wherein the PPI varies gradually from the proximal portion to the distal portion of the shaft whereby the stiffness of the shaft diminishes gradually from the proximal portion to the distal portion. In another embodiment, the braided-wire plait matrix wraps around the inner layer of the shaft. In another embodiment, the helical coil of wire wraps around the inner layer of the shaft. In yet another embodiment, the pitch of the helical coil at the proximal portion of the shaft is smaller than the pitch of the helical coil at the distal portion of the shaft. In another embodiment, the shaft of the transporter catheter comprises a helical coil of wire, wherein the pitch increases gradually from the proximal portion to the distal portion of the shaft whereby the stiffness of the shaft diminishes gradually from the proximal portion to the distal portion.

The torque-transfer layer may be made of stainless steel (304 or 316) wire or other acceptable materials known to those of ordinary skill in the art. In one embodiment, the torque-transfer layer is formed of a braided wire assembly comprised of flat wires, preferably stainless-steel wires including, for example, high tensile stainless-steel wires. The torque-transfer layer may be formed in any combinations of braid patterns, including one-over-one (involving at least two wires) or two-over-two (involving at least four wires) crossover patterns. In one embodiment, the torque-transfer layer may utilize a varying braid density construction along the length of the transporter catheter. For example, the torque-transfer layer may be characterized by a first braid density at the proximal end of the transporter catheter and then transition to one or more braid densities as the torque-transfer layer approaches the distal end of the transporter catheter. The braid density of the distal end may be greater or lesser than the braid density at the proximal end. In one embodiment, the braid density at the proximal end is about 50 PPI and the braid density at the distal end is about 10 PPI. In another embodiment, the braid density at the distal end is about 20-35% of the braid density at the proximal end. The torque-transfer layer may be formed separately on a disposable core and subsequently slipped around an inner liner. One or more portions of the torque-transfer layer may be heat-tempered and cooled before incorporation into the transporter shaft through methods that are known to those of ordinary skill. The action of heat tempering may help to release the stress on the wire and help to reduce radial forces. In another embodiment, the torque-transfer layer may be braided directly on the inner liner. In yet another embodiment, the torque-transfer layer may include at least one helical coil of steel wire. The distance between two consecutive spirals (known as the pitch) of the helical coil may vary along the length of the transporter catheter. For example, the torque-transfer layer may be characterized by a first pitch of helical coil at the proximal end of the transporter catheter and then transition to one or more pitches as the torque-transfer layer approaches the distal end of the transporter catheter. The pitch of the helical coil at the distal end may be greater or less than the pitch of the helical coil at the proximal end. In one embodiment, the pitch at the distal end is about 50-80% greater than the pitch at the proximal end.

Figure 3:
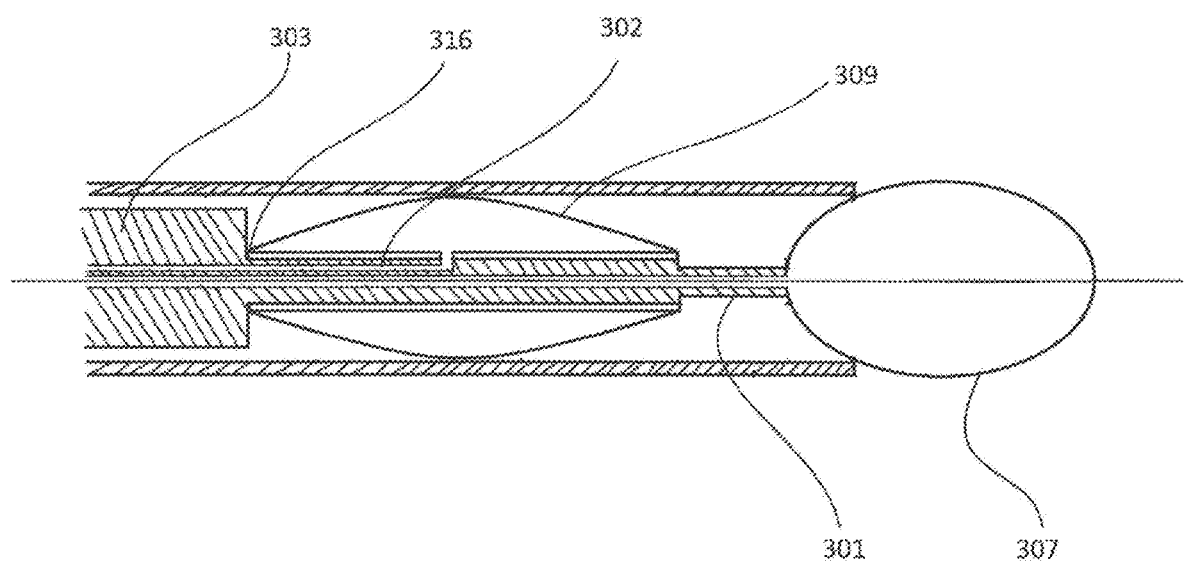
FIG. 3 illustrates a sectional view of a transporter catheter having multiple segments of the transporter catheter with multiple degrees of flexibility.

In another embodiment of the invention shown in FIG. 3, the shaft has a first flexible portion 301 disposed at the distal end of the shaft, a second flexible portion 302, which is continuous with the first flexible portion 301 and flexible, but that has a higher degree of hardness than the first flexible portion 301, and a flexible portion 303, which is continuous with the second flexible portion 302 and that has a higher degree of hardness than the second flexible portion 302. In the embodiment shown in FIG. 3, the most flexible first flexible portion 301 is between the orienting balloon 307 and the anchoring balloon 309. The second flexible portion 302 of the shaft is substantially covered by the anchoring balloon 309. The third flexible portion 303 has a degree of hardness higher than the hardness of the second flexible portion and the first flexible portion and extends from the proximal end 102 of the catheter 100 to the proximal edge 116, 316 of the anchoring balloon 309. The flexibility of transporter catheter becomes stepwise lower from its distal end to its proximal end. Because the portion 301 of the shaft proximate to the orienting balloon 307 is flexible, the orienting balloon 307 is capable of passing through a curved portion of a vessel with greater ease.

Figure 4A:
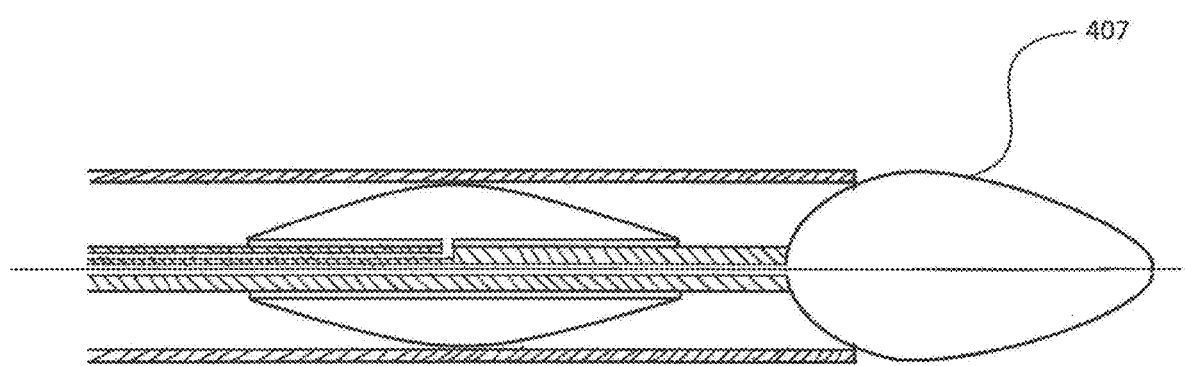
FIG. 4a illustrates a sectional view of a transporter catheter showing a contoured orienting balloon that facilitates smooth movement of the orienting balloon by reducing drag.
Figure 4B:
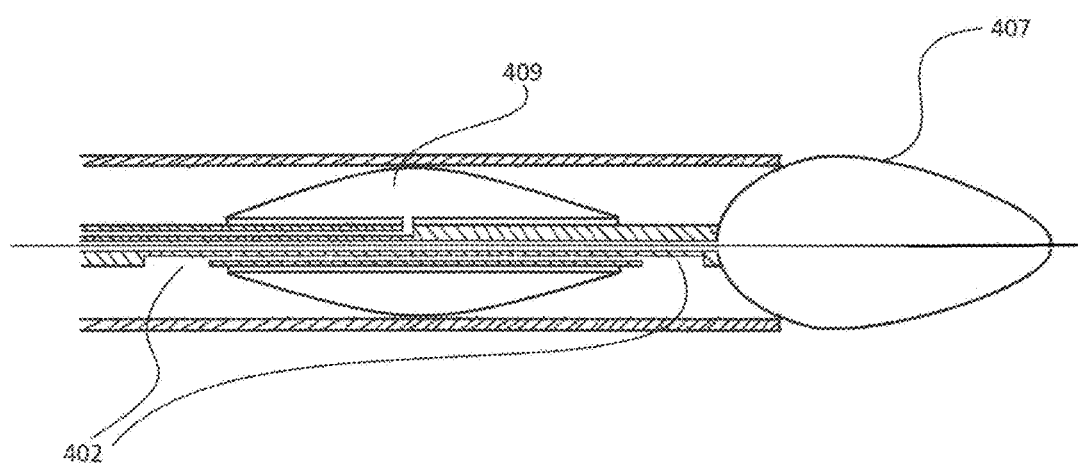
FIG. 4b illustrates a sectional view of a transporter catheter showing a perfusion lumen to perfuse blood across the anchoring balloon when the anchoring balloon is inflated.
Figure 4C:
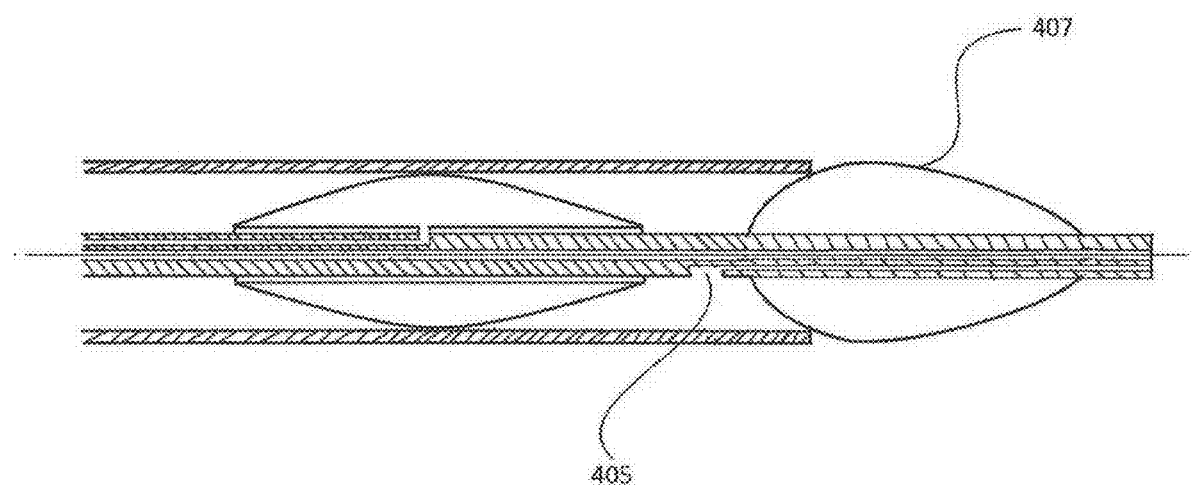
FIG. 4c illustrates a sectional view of a transporter catheter showing a perfusion lumen to perfuse blood across the orienting balloon when the orienting balloon is inflated.
Figure 5:
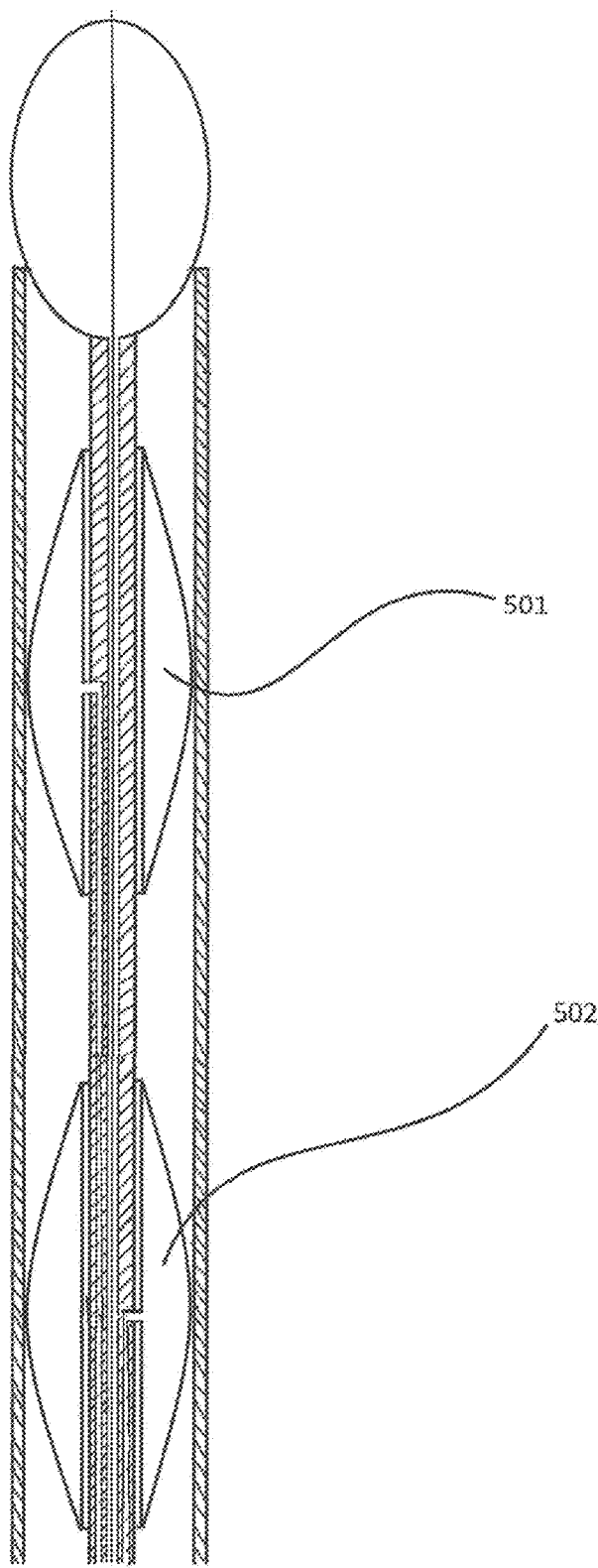
FIG. 5 illustrates a sectional view of a transporter catheter with more than one anchoring balloons.
Figure 6:
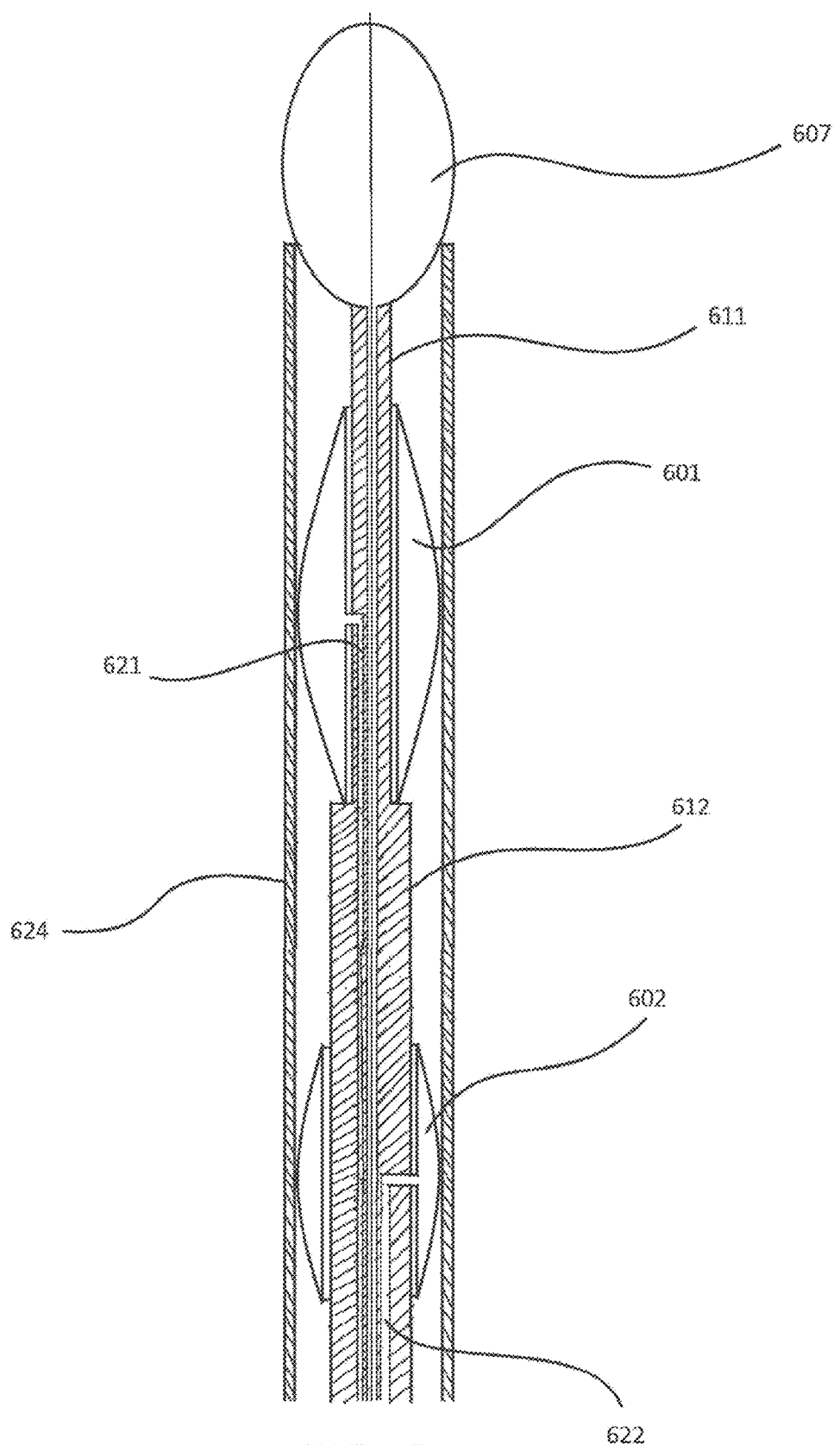
FIG. 6 illustrates a sectional view of a transporter catheter having multiple segments of varying degrees of hardness, with an anchoring balloon present on more than one segment.

In one embodiment as illustrated in FIG. 4a, the distal end of the orienting balloon 407 is smooth and contoured to provide smooth movement of the orienting balloon. In another embodiment, the surface of the orienting balloon is coated with a friction-reducing coating. In another embodiment, the surface of the orienting balloon may have a wavy contour or other three-dimensional contours (not shown) when inflated to provide channels for perfusion of blood across the orienting balloon when the orienting balloon is inflated. In one embodiment as illustrated in FIG. 4b, a perfusion lumen 402 is provided to perfuse blood across the anchoring balloon 409 when the anchoring balloon 409 is inflated. In another embodiment as illustrated in FIG. 4c, a perfusion lumen 405 is provided to perfuse blood across the orienting balloon 407 when the orienting balloon 407 is inflated. In one embodiment as illustrated in FIG. 5 multiple anchoring balloons 501, 502 may be present. In another embodiment illustrated in FIG. 6, at least one anchoring balloon may be present in each flexible portion of the shaft, e.g., a first anchoring balloon 601 is present in a first flexible portion 611 and a second anchoring balloon 602 is present in a second flexible portion 612. The first anchoring balloon 601 is inflated using the first lumen 621 and the second anchoring balloon 602 is inflated using the second lumen 622, thereby the first anchoring balloon 601 may be inflated or deflated independently from the inflation or deflation of the second anchoring balloon 602, and vice versa. In another embodiment (not shown), a single lumen connects a plurality of anchoring balloons, whereby all anchoring balloons inflate or deflate simultaneously. In one embodiment, one or more anchoring balloons may be anchored to the introducer catheter 624 depending on how the orienting balloon 607 advances through the vasculature of a patient's body. More than one anchoring balloon may be inflated independently if the orienting balloon 607 and/or the introducer catheter 624 experiences increased resistance to move in a patient's vasculature. In another embodiment, an orienting balloon may be present at the distal edge of the introducer catheter. In another embodiment, an anchoring balloon may be located in a distal portion of the introducer catheter. An anchoring balloon located on the introducer catheter, upon inflation, may press against the outer surface of the transporter catheter to non-slidably anchor the introducer catheter to the transporter catheter.

Figure 7:
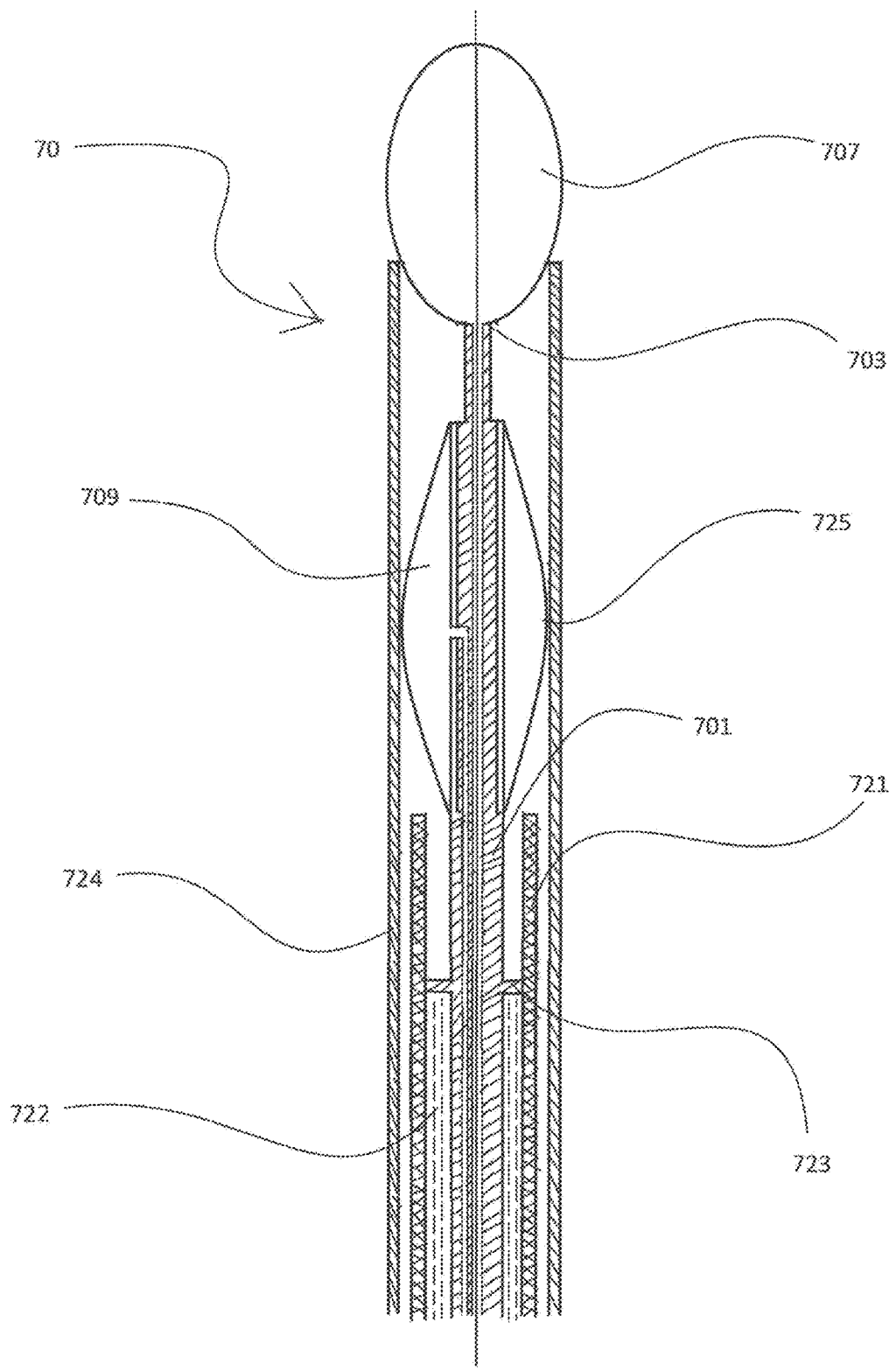
FIG. 7 illustrates a sectional view of a transporter catheter having a hydraulic system to advance the transporter catheter.

In yet another embodiment of the invention shown in FIG. 7, an introducer catheter to which a transporter catheter is anchored is advanced using hydraulic pressure. The system 70 comprises the transporter catheter with a shaft 701, an orienting balloon 707 located at a distal end of the shaft 701, a hydraulic fluid lumen 721, hydraulic fluid 722, and a piston 723 movably disposed in the hydraulic fluid lumen and connected to the shaft 701 of the transporter catheter. The piston forms a seal with an interior surface of the hydraulic fluid lumen. A hydraulic driver, e.g., a syringe, that generates hydraulic pressure against the piston sufficient to advance the shaft 701 of the transporter catheter, is used. The anchoring balloon 709, which is connected to the shaft 701, advances with the shaft. Upon inflation, the anchoring balloon 709 is anchored to the inner surface 725 of the introducer catheter 724, and thereby the advancement of the anchoring balloon 709 also advances the introducer catheter 724 through a patient's vasculature. In one embodiment, the method of advancing the introducer catheter a first distance inside a patient's vasculature comprises the following steps: (a) positioning the transporter catheter inside the introducer catheter; (b) inflating the orienting balloon; (c) adjusting the position of the transporter catheter whereby the orienting balloon is substantially outside the distal end of the introducer catheter; (d) inflating the anchoring balloon to anchor the transporter catheter to the inside surface of the lumen of the introducer catheter; (e) applying hydraulic pressure to the piston to advance the introducer catheter. In another embodiment, after advancing the introducer catheter a first distance using hydraulic pressure, the introducer catheter is advanced a second distance using the following method: (i) deflating the anchoring balloon; (ii) reducing the hydraulic pressure; (iii) repositioning the transporter catheter inside the lumen of the introducer catheter; (iv) inflating the anchoring balloon to anchor the transporter catheter to the introducer catheter; and (v) applying hydraulic pressure again. Steps (i) to (v) may be repeated to continue advancing the catheter system. In one embodiment, the inflation medium comprises a 1:2 mixture of contrast medium and normal saline solution.

In one embodiment, the length of the transporter catheter 100 may be from about 100 cm to about 250 cm. The end use and the length of the introducer catheter may determine the length of the transporter catheter. By way of illustration only and not by way of limitation, and depending on physiology of a patient, a cerebral vasculature application may warrant a transporter catheter length from about 100 cm to about 150 cm; a coronary vasculature application may warrant a transporter catheter length from about 100 cm to about 160 cm in length; a peripheral vasculature application may warrant a transporter catheter length from about 70 cm to about 100 cm in length; a renal vasculature application may warrant a transporter catheter length from about 60 cm to about 90 cm in length; and a hepatic vasculature application may warrant a transporter catheter from about 70 cm to about 100 cm in length. In one embodiment, the outer diameter of the shaft 101 of the transporter catheter 100 may range from about 2 French to about 12 French, or higher. In another embodiment, the outer diameter of the shaft 101 of the transporter catheter 100 may be in the range from about 4 mm to about 10 mm, or higher. However, the dimensions of the shaft 101 of transporter catheter 100 may vary in accordance with various applications of the catheter system and size of the introducer catheter.

In one embodiment, the difference between the outer diameter of the shaft of the transporter catheter and the inner diameter of the introducer catheter is less than 0.5 mm. In another embodiment, the outer diameter of the shaft of the transporter catheter is about 0.5 mm smaller than the inner diameter of the introducer catheter. In another embodiment, the outer diameter of the shaft of the transporter catheter is about 1 mm to about 2 mm smaller than the inner diameter of the introducer catheter. In yet another embodiment, outer diameter of the shaft of the transporter catheter is about half of the inner diameter of the introducer catheter. In another embodiment, the length of the transporter catheter may be from about 20 cm to about 60 cm. In yet another embodiment, the transporter catheter may have short lengths, e.g., in the range of about 3 cm to about 10 cm. In another embodiment, the transporter catheter may have length in the range of about 10 cm to about 300 cm. In one embodiment, an orienting balloon may be located about 3 mm from the distal tip of the transporter catheter. In another embodiment, the gap between the distal end of the anchoring balloon and the proximal end of the orienting balloon may be in the range of about 2-10 mm. In another embodiment, the gap between the distal end of the anchoring balloon and the proximal end of the orienting balloon may be in the range of about 3-5 mm. In one embodiment, the outer diameter of the orienting balloon is about the same as the outer diameter of the introducer catheter. In another embodiment, the outer diameter of the orienting balloon is greater than the outer diameter of the introducer catheter. In one embodiment, the orienting balloon is compliant. In another embodiment, the anchoring balloon is non-compliant or semi-compliant. In yet another embodiment, the orienting balloon is semi-compliant.

The distal end 103 of the shaft 101 may or may not be tapered. In one embodiment, shaft 101 may have a taper, with the proximal end 102 having larger diameter than the distal end 103. The end use and the inside diameter of the introducer catheter may determine the outer diameter of the shaft 101. In one embodiment, shaft 101's inner diameter may range from about 1 French to about 3 French, or higher. If shaft 101 is to receive a guidewire 108, the inner diameter of the shaft will need to be proportioned accordingly. In one embodiment, guidewires up to 1.4 French in diameter may be used. In another embodiment, guidewires may not be used in conjunction with the transporter catheter and the transporter catheter may not have lumen 105 for a guidewire. In one embodiment, the transporter catheter may deliver the introducer catheter to the desired location over a guidewire. In another embodiment, the transporter catheter may deliver the introducer catheter to the desire location without the use of the guidewire. After the introducer catheter is positioned, stylet(s) if present may be removed, then the orienting balloon and the anchoring balloon may be deflated by means of a hand-held syringe or other means. In one embodiment, the transporter catheter is configured to track over a 0.009-0.014" guidewire. In another embodiment, the transporter catheter may have a central lumen capable of accommodating guidewires of various diameters (e.g., guidewire with a diameter in the range 0.010" to 0.065"). In another embodiment, the transporter catheter may have a lumen capable of accommodating guidewire that are not circular, e.g., flat guidewires. In yet another embodiment, the guidewire lumen may have a rectangular cross-sectional shape. In some embodiments, the guidewire lumen may not be at the center of the shaft 101 and may be offset from the center of the shaft 101. In one embodiment, the transporter catheter may be structured in a "rapid exchange" configuration. In another embodiment, the transporter catheter may be structured in an "over-the-wire" configuration. In another embodiment, the transporter catheter may not include an orienting balloon, and may include at least one anchoring balloon and/or may include at least one mechanical connector, said anchoring balloon and/or mechanical connector located at the distal end of the transporter catheter. The at least one anchoring balloon and/or the at least one mechanical connector anchors the distal end of the transporter catheter to the outer catheter. In one embodiment, the distal end of the transporter catheter is anchored to the distal end of the outer catheter. In another embodiment, the at least one anchoring balloon and/or the at least one mechanical connector are located in the distal end portion of the transporter catheter. In yet another embodiment, the distal end portion of the transporter catheter is anchored to the distal end portion of the outer catheter.

Figure 8A:
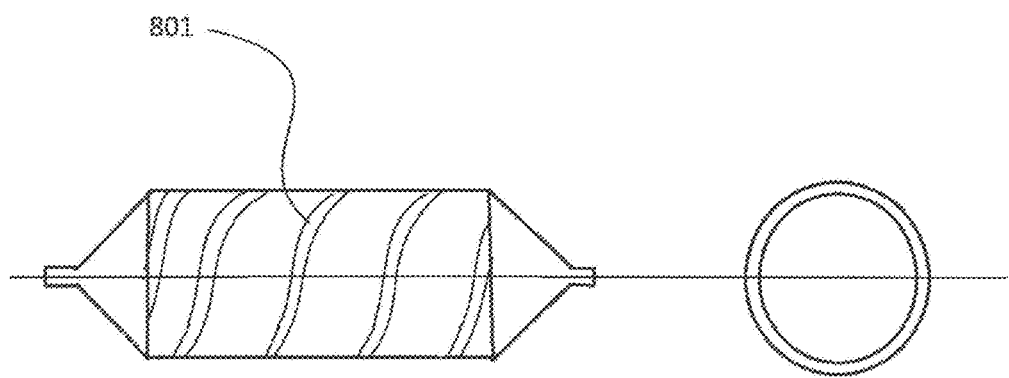
FIG. 8a-d are perspective views of modifications to the surface of the anchoring balloon to enhance anchoring to the inner surface of an introducer catheter.
Figure 8B:
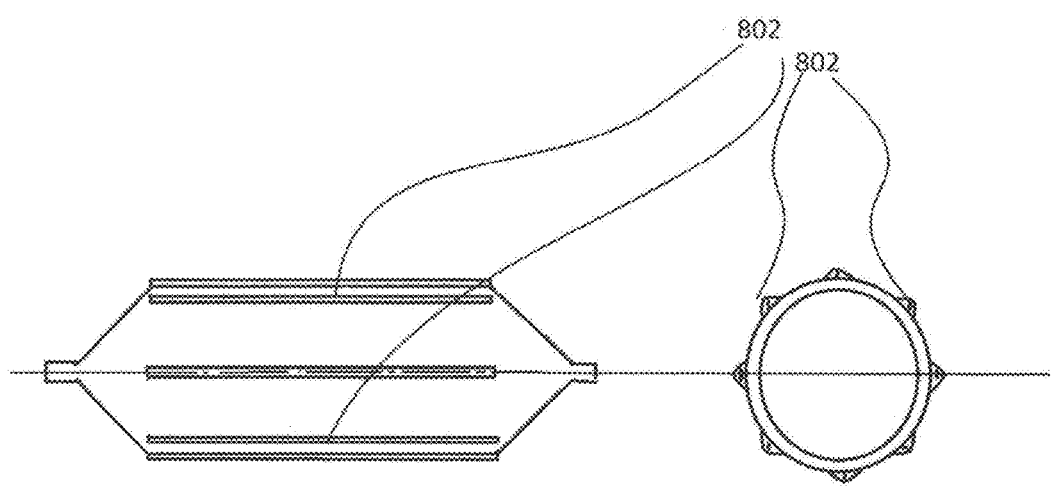
Figure 8C:
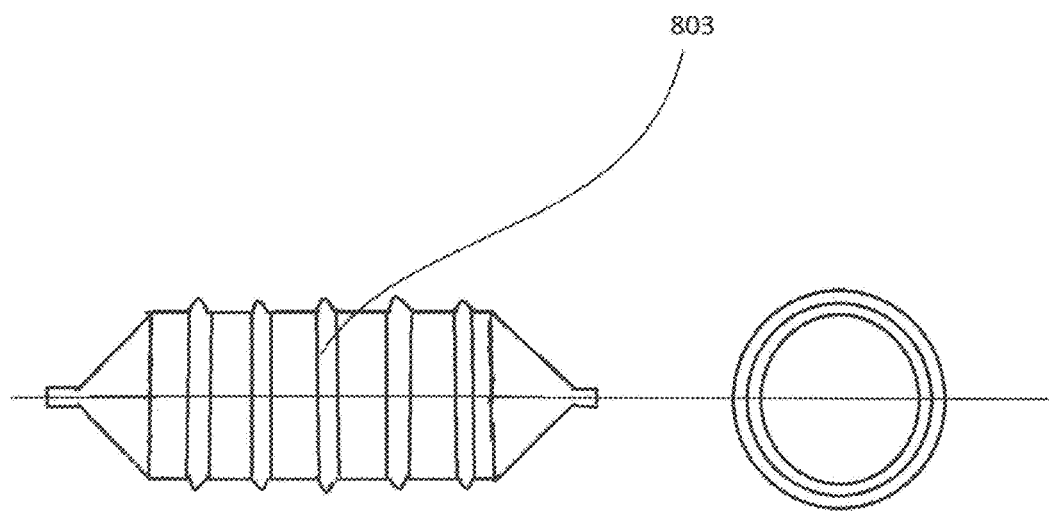
Figure 8D:
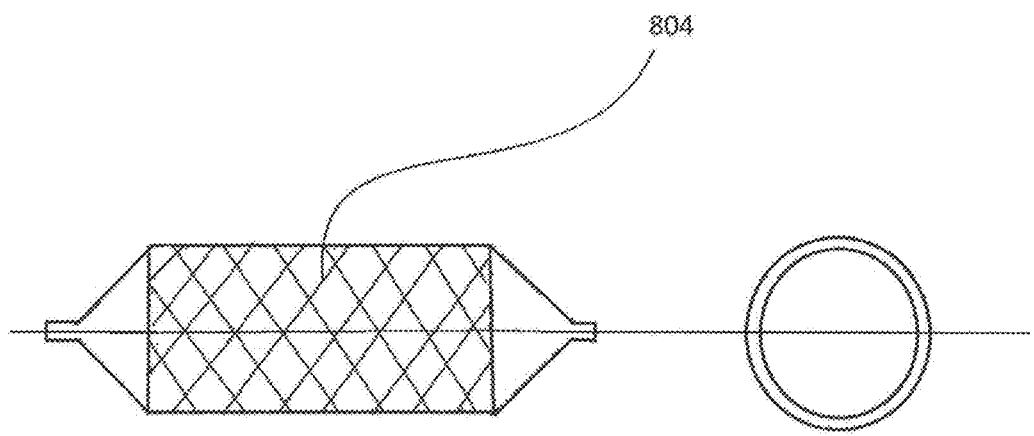

The material for shaft 101, lumens 104, 105 and 106, orienting balloon 107 may contain any one or more of the following additives. By way of illustration only and not limitation, such additives may include radiopaque fillers, slip additives, and hydrophilic coatings. In one embodiment, silicon provides hydrophilic coating. In another embodiment, the material for shaft 101 comprises a particulate radiopaque filler material. In one embodiment, an anchoring mechanism to non-slidably engage and anchor the transporter catheter to the outer catheter is a friction-based mechanism between an outer surface of the transporter catheter and an inner surface of the outer catheter. In another embodiment, the anchoring balloon may be made of materials and/or coated with materials that provide frictional resistance to reduce slippage. In one embodiment, the anchoring balloon may be made of polyurethane. In another embodiment, the anchoring balloon may have serrations 801 as illustrated in FIG. 8*a* and/or raised projections 802 as illustrated in FIG. 8*b* to enhance the anchoring capability of the anchoring balloon to the inside of the introducer sheath after the anchoring balloon is inflated. The serrations and/or raised projections may have spiral shape 801 as shown in FIG. 8*a*, linear shape 802 as shown in FIG. 8*b*, and other shapes, see for example, circular ring shape 803 (see FIG. 8*c*) or crisscross checkered shape 804 (see FIG. 8*d*). The projections may have inserts, e.g., wires. The wires or wire segments may be made from various materials, and may each be made of the same materials or materials with similar material properties, or different materials having different properties. As an example, such wires or wire segments may be formed from stainless steel. The material of wires may be stiffer than the materials forming the wall of the balloon. In another embodiment, the wires may be made of Nitinol. The projections enhance the anchoring capability of the anchoring balloon to the inside surface of the outer catheter, such as an introducer catheter, by coarsening the outer surface of the anchoring balloon and anchoring the outer surface of the anchoring balloon to the inner surface of the introducer catheter. The wire or wire segments forming the projections may also have any cross-sectional geometric shape, including for example, circular, square, or triangular, and different projections may have different cross-sectional shapes. Rounded shapes and/or smooth edges may help to prevent the wire or wire segment forming the projection from perforating the wall of the anchoring balloon. In one embodiment, the wire or wire segments may be hollow to allow for passage of blood, thereby preventing occlusion of blood when the anchoring balloon is inflated. In another embodiment, the inner surface of the outer catheter may be configured at a distal portion of the outer catheter to enhance frictional anchoring capability, e.g., the inner surface of the outer catheter at the distal portion may have a layer of material with higher friction coefficient or may have knurling or serrations or may otherwise treated so as to increase frictional resistance in that portion of the inner surface of the outer catheter.

In one embodiment, the wires or wire segments comprise a material that is radiopaque (either a homogeneous material or a material that is non-radiopaque, but is provided with a radiopaque coating), and thus visible under fluoroscopy. Making the projections visible may also allow the clinician to better discern the location and orientation of the anchoring balloon, as well as the position of the anchoring balloon before inflating and anchoring the balloon to the inner surface of the introducer catheter. In another embodiment, the wall of the anchoring balloon may comprise radiopaque particles.

In one embodiment, at least one mechanical connector is used to connect and anchor the transporter catheter and the introducer catheter. In another embodiment, the transporter catheter comprises a mechanical connector to anchor the transporter catheter to the inner surface of the introducer catheter. In yet another embodiment, the transporter catheter comprises a mechanical connector to anchor the transporter catheter to the introducer catheter at or near the distal edge of the introducer catheter. In another embodiment, the transporter catheter and/or the introducer catheter comprises at least one mechanical connector located in the distal portion of the transporter catheter and/or the distal portion of the introducer catheter. In one embodiment, a handle at the proximal end of the transporter catheter may be used to engage the mechanical connector thereby enabling the anchoring of the transporter catheter to the introducer catheter. The handle at the proximal end of the transporter catheter may also be used to disengage the mechanical connector thereby allowing the removal of the transporter catheter from the introducer catheter. In another embodiment, a handle at the proximal end of the introducer catheter may be used to engage or disengage the mechanical connector. In one embodiment, the mechanical connector is a circular cage of a matrix of round or flat wires wherein the diameter of the cage can be increased or decreased mechanically. In another embodiment, diameter of the cage may be increased or decreased, e.g., by rotating the handle at the proximal end of the transporter catheter, whereby when the handle is rotated in one direction, the cage is torqued to open and increase its diameter, and when the handle is rotated in other direction, the cage is torqued to close and decrease its diameter. The diameter of the cage is increased until it presses against the inner surface of the introducer catheter to anchor the transporter catheter to the introducer catheter. In another embodiment, the mechanical connector may be located on the introducer catheter and the mechanical connector engages, e.g., presses against or locks the transporter catheter to anchor the introducer catheter to the transporter catheter.

In operation, a transporter catheter and an outer catheter may be advanced from various arterial access sites, such as femoral, radial, brachial, axillary and carotid artery to gain percutaneous or operative entry to arterial circulation. In one embodiment, once access is gained, a device is advanced from the access point via the aorta to the desired target location for diagnostic or interventional procedure. Introduction of a catheter directly through an arteriotomy increases the possibility of abrasion by the catheter edge against the inner arterial wall (also known as intima). To reduce the risk of this possible interaction, a guidewire is typically first advanced through an arteriotomy. The guidewire is typically a soft tipped, lower profile, flexible object, e.g., with a tip that is atraumatic. The placement of the guidewire and introduction of the catheter over the guidewire centers the catheter in the lumen of the artery and reduces the risk of abrasion of the catheter against the inner arterial wall. Despite the decreased risk to the intima of the arterial circulation because of guidewire placement and over-the-wire advancement, there still remains a risk of abrasion of the internal wall of the arterial vessels by the overhang of the catheter in view of the fact that the guidewire is frequently significantly smaller in diameter compared to the catheter. This abrasive effect of the catheter, which is generally termed as "razor effect", may lead to dislodgement of elements from the inner arterial wall, such as atherosclerotic as well as other debris. Liberated atherosclerotic, as well as other debris, then may follow the arterial circulation and may lodge into a small distal branch based on the size of such debris. This event may lead to tissue death or necrosis, which may lead to permanent organ dysfunction, including ischemic necrosis of the bowel because of an athero-embolic event, acute kidney injury because of a similar embolic event, as well as cerebrovascular events from liberation of atheroma that may be caused by catheter transit through the ascending aorta and the aortic arch. An embodiment of the present invention comprising the orienting balloon generally provides resolution of the overhang, reducing the potential of the transitions, and hence reducing the razor effect and lowering the risk of embolic events that may result from catheter transit.

Figure 9:
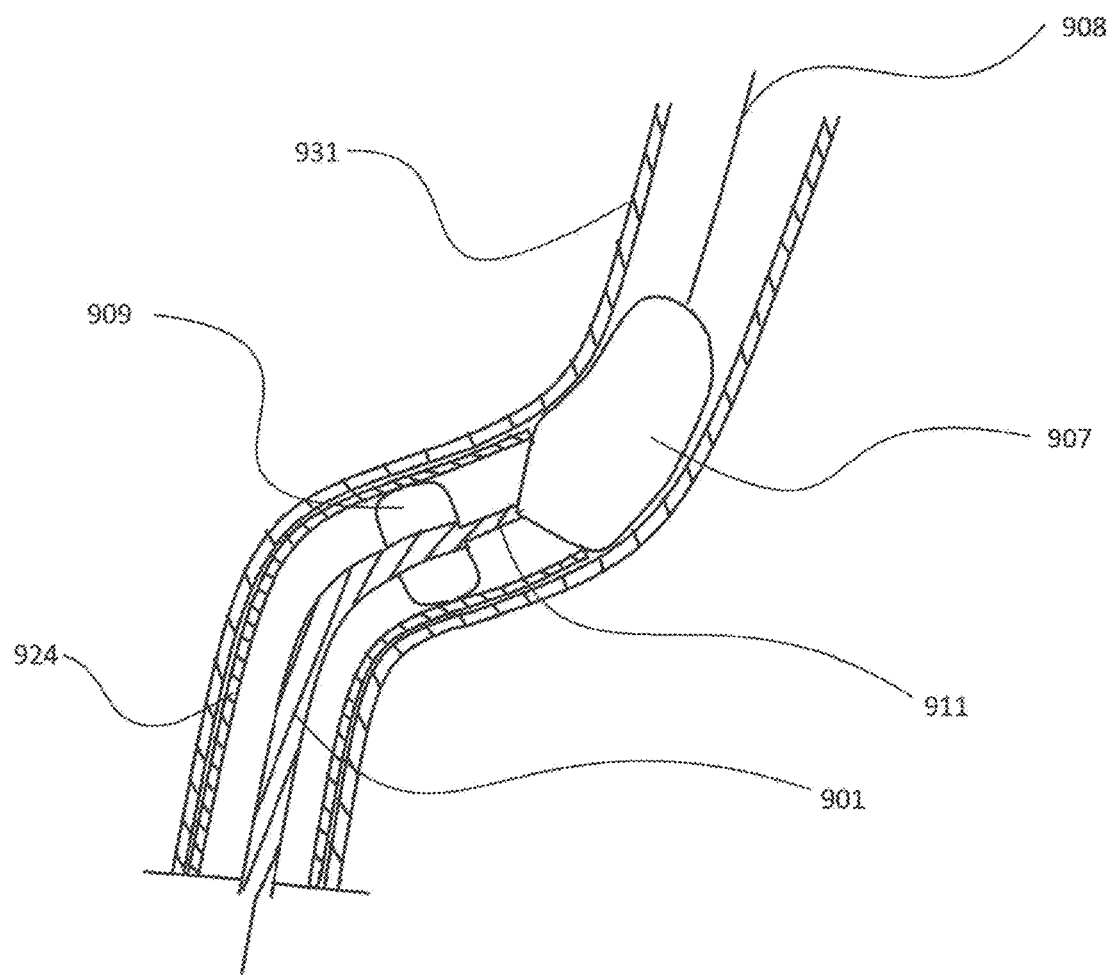
FIG. 9 is a perspective view of a catheter system comprising a transporter catheter and an introducer catheter advancing through a vasculature of a patient's body.

In operation as illustrated in FIG. 9, the orienting balloon 907 orients and maneuvers the catheter system comprising the introducer catheter 924 and the transporter catheter 901 through the curves of the vasculature 931 in a patient's body. The orienting balloon 907 protrudes outside the introducer catheter 924. In one embodiment, about 50% of the orienting balloon protrudes outside the introducer catheter 924. In another embodiment, more than 50% of the orienting balloon 907 protrudes outside the introducer catheter. In yet another embodiment, about 80% of the orienting balloon 907 protrudes outside the introducer catheter 924. In another embodiment, less than 50% of the orienting balloon 907 protrudes outside the introducer catheter 924. In one embodiment, the orienting balloon may be inflated using a pressure from about 2 atmospheres to about 10 atmospheres or higher. In another embodiment, the orienting balloon may be inflated to a pressure in the range 12-15 atmospheres. In another embodiment, the orienting balloon is inflated using a pressure of about 4 atmospheres. In one embodiment, the diameter of protruding portion of the orienting balloon, that protrudes out from the introducer catheter may be larger than the outer diameter of the introducer catheter thereby substantially reducing or eliminating a potential razor effect of the edge of the introducer catheter. In one embodiment, two orienting balloons may be present. In another embodiment, the diameters of the two orienting balloons may be the same. In yet another embodiment, the diameter of the distal orienting balloon may be less or greater than the diameter of the proximal orienting balloon. In one embodiment, the proximal orienting balloon is partially inside the introducer catheter and partially protrudes outside the introducer catheter, and the distal orienting balloon is entirely outside the introducer catheter. In some embodiments, more than two orienting balloons may be present. In one embodiment, the diameters of the orienting balloons may gradually decrease from the proximal orienting balloon to the distal orienting balloon located near the tip of the introducer catheter. In one embodiment, the orienting balloons are coated and/or contoured to minimize friction between the orienting balloons and the inner surface of the patient's vasculature. Upon expansion, at least one orienting balloon engages the inner surface of the patient's vasculature. In one embodiment, an orienting balloon may slidably engage the inner surface of the patient's vasculature upon full expansion of the balloon. In another embodiment, an orienting balloon may slidably engage the inner surface of the patient's vasculature upon partial expansion of the balloon. In an embodiment where more than one orienting balloon is present, the first orienting balloon may engage the inner surface of the patient vasculature and the second orienting may not engage the inner surface of the patient's vasculature. In another embodiment, the proximal orienting balloon protruding outside the introducer catheter engages the inner surface of the patient's vasculature upon full expansion of the proximal orienting balloon and the distal orienting balloon upon full expansion does not engage the inner surface of the patient's vasculature. The anchoring balloon 909 anchors the shaft of the transporter catheter 901 to the inner surface of the lumen of the introducer catheter 924. In one embodiment, a guidewire 908 may be present. In another embodiment, segment 911 between the anchoring balloon 909 and the orienting balloon 907 may be more flexible than segment 901 of the transporter catheter. The catheter system may be advanced by pushing and/or torqueing the introducer catheter 924, or the transporter catheter 901, or both. If the catheter system is advanced by pushing the introducer catheter, the wall of the introducer catheter should have enough axial strength to be pushed through the patient's vasculature via a force applied at its proximal end ("pushability"). It is also desirable for the introducer catheter to be capable of transmitting a torque applied at the proximal end along the length of the shaft through to the distal end ("torqueability"). An introducer catheter should also have enough flexibility to conform substantially to the patient's vasculature and yet resist kinking as it is pushed and/or torqued through the patient's vasculature and conforms to the patient's vasculature.

The wall of an introducer catheter 924 that is advanced by pushing the introducer catheter is thick and increasing the bore size of an introducer catheter having a given overall diameter requires utilizing a thinner wall. Now that catheters are used in smaller and smaller vessels and body lumens, there is a growing need to use introducer catheters that have a smaller wall thickness. However, a thin-walled introducer catheter that is pushed through the patient's vasculature is more likely to collapse upon itself or kink when a push force and/or torque is applied at its proximal end. On the other hand, if the introducer catheter 924 is pulled through the patient's vasculature by an anchoring balloon 909 of a transporter catheter, then the wall of the introducer catheter 924 may be relatively thinner. A thin wall may be used because when the introducer catheter 924 is pulled through the patient's vasculature 931, a pulling tensile force is applied to the wall of the introducer catheter 924. The tensile force has a stretching effect on the wall of the introducer catheter and prevents kinking of the wall of the introducer catheter 924. On the other hand, if the introducer catheter 924 is pushed through the patient's vasculature, a compressive force is applied to the wall of the introducer catheter 924. If the introducer catheter 924 experiences resistance and push-back from a patient's lumen, the compressive force could result in kinking of the wall of the introducer catheter 924. In one embodiment, pushing the transporter catheter to advance the outer catheter to a desired location in a patient's body results substantially in pulling the outer catheter to the desired location. In one embodiment, thickness of the wall of the introducer catheter 924 is less than thickness of the wall of the transporter catheter 901. In another embodiment, the wall of the introducer catheter 924 is more flexible than the wall of the transporter catheter 901. In another embodiment, the wall of the transporter catheter 901 comprises a structure of wires to increase the stiffness of the wall of the transporter catheter. In another embodiment, the wall of the introducer catheter 924 does not comprise a structure of wires. In yet another embodiment, the introducer catheter 924 in the proximal end portion of the introducer catheter may be more flexible than the transporter catheter 901 in the proximal end portion of the transporter catheter. In one embodiment, thickness of the wall of the introducer catheter 924 is less than 0.2 mm. In another embodiment, the thickness of the wall of the introducer catheter 924 is less than 0.1 mm. In yet another embodiment, the thickness of the wall of the introducer catheter 924 is less than 0.5 mm. In one embodiment, the outer wall of the introducer catheter 924 is provided with a hydrophilic coating to reduce friction between the outer wall of the introducer catheter 924 and the inner wall of a lumen 931 through which the introducer catheter is being advanced.

Figure 10A:
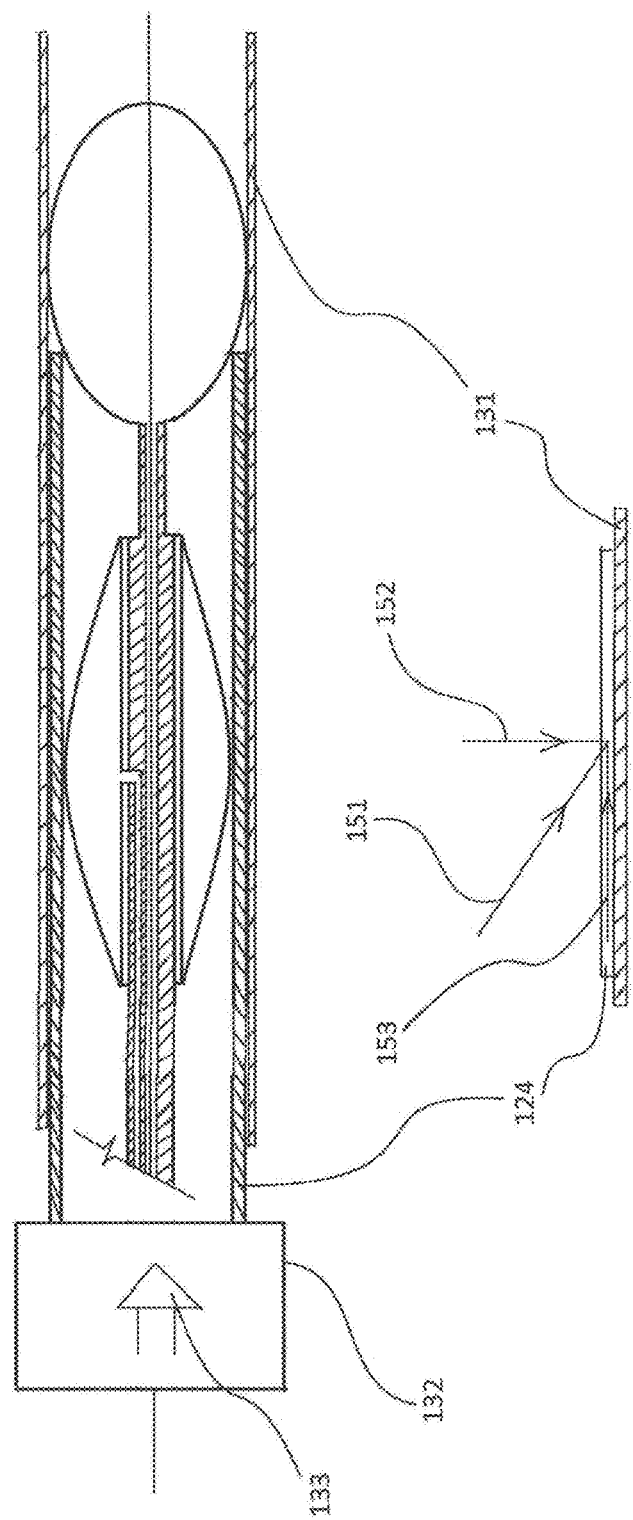
FIG. 10a-b is a schematic of forces acting on a wall of an introducer catheter when it is pushed at its proximal end or pulled at its distal end.

FIG. 10a is a schematic of the forces that act on the introducer catheter when a user pushes the introducer catheter in direction 133 at the proximal end of the introducer catheter 124 using a handle 132. The push force 151 on the wall of the introducer catheter has a horizontal component 153 that advances the introducer catheter 124 through the vasculature 131 of the patient's body, and a vertical component 152 that presses the wall of the introducer catheter 124 against the wall of the vasculature 131. Because component 152 is directed towards the wall of the vasculature 131, the component 152 adds frictional resistance and drag to the introducer catheter as it advances through the vasculature. Because of the additional frictional resistance, a greater push force is required, thereby requiring a thicker wall for the introducer catheter so that the introducer catheter does not collapse or kink. A greater push force also results in additional frictional resistance because of a larger vertical component 152. Total frictional resistance depends on the contact area between the introducer catheter and the vasculature and therefore depends in part on the length of the introducer catheter that is inserted into the vasculature of a patient's body. Because of the compounding of the frictional resistance with increase in push force, the length to which an introducer catheter can be pushed inside the vasculature may be limited.

Figure 10B:
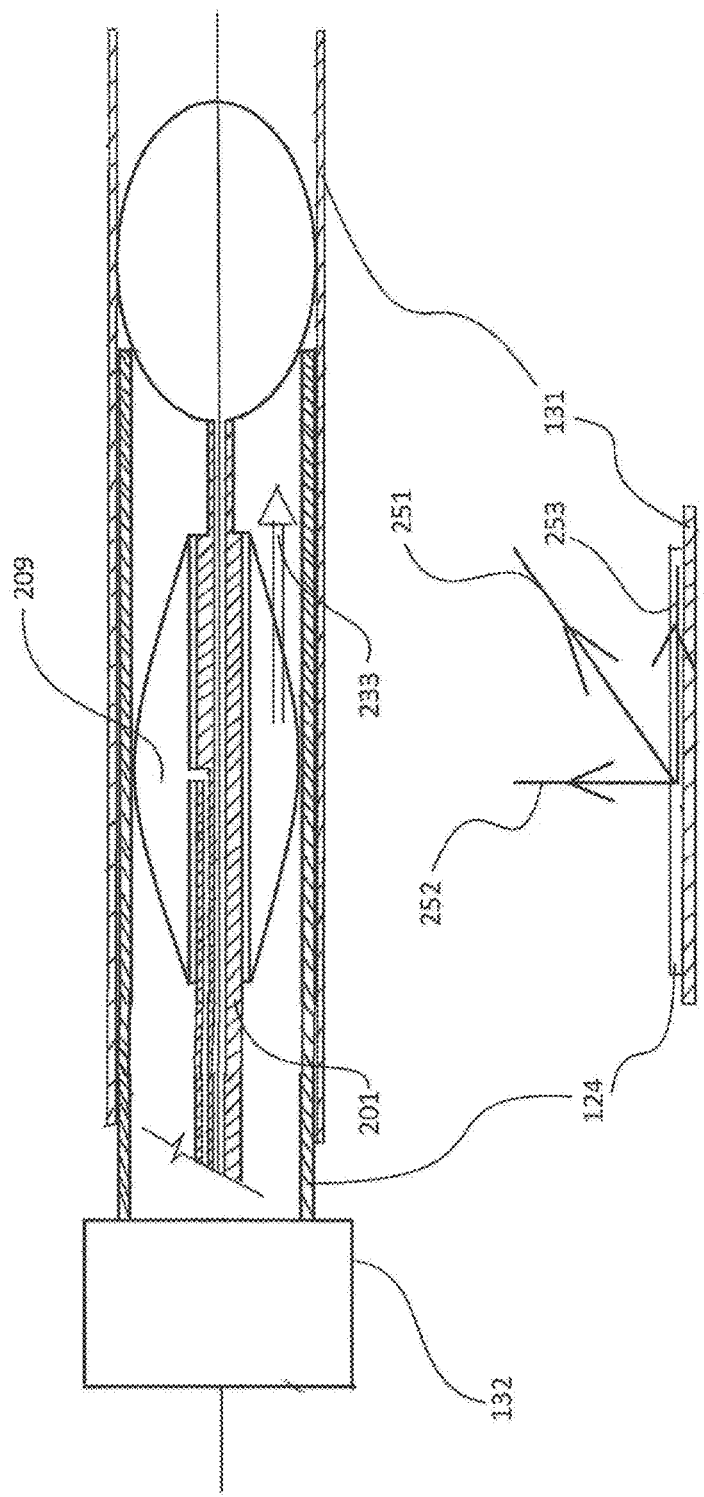

FIG. 10b is a schematic of the forces that act on the introducer catheter as it is pulled by the anchoring balloon of the transporter catheter when the user pushes the transporter catheter to advance the introducer catheter. When a user pushes the transporter catheter 201 and with it, its anchoring balloon 209 in the direction 233, the anchoring balloon exerts a pull force 251 on the wall of the introducer catheter 124. The pull force 251 on the wall of the introducer catheter has a horizontal component 253 that advances the introducer catheter 124 through the vasculature 131 of the patient's body, and a vertical component 252 that pulls the wall of the introducer catheter 124 away from the wall of the vasculature 131. Because component 252 is directed away from the wall of the vasculature, the component 252 reduces the frictional resistance and the drag on the introducer catheter as it advances through the vasculature. Consequently, a smaller push force is required on the transporter catheter to advance the catheter system through the vasculature. Furthermore, because the walls of the introducer catheter experience a pull force at the distal end (rather than a push force at the proximal end), the possibility of kinking the wall of the introducer catheter is reduced, and a thinner wall may be used for the introducer catheter. The transporter catheter is removed after the introducer catheter is positioned at a desired location. Thus, for a given outer diameter of an introducer catheter and by using a transporter catheter to advance the introducer catheter (or to advance any other outer catheter such as a sheath, a guide catheter, or a mother catheter), the user may use an introducer catheter with a thinner wall, thereby providing a larger diameter of its inner lumen. In one embodiment, the transporter catheter may be used to pull the introducer catheter through the tortuosity of arteries, including celiac and mesenteric arteries. In another embodiment, a catheter system comprising the transporter catheter may be used to perform revascularization as well as devascularization in cerebral circulation. In yet another embodiment, a catheter system comprising the transporter catheter may be used to cannulate a middle coronary vein, while implanting a CRT-D device or other devices. In one embodiment, a catheter system comprising the transporter catheter may be used in a remote tele-robotic procedure, such as stroke management. In another embodiment, a system comprising the transporter catheter may be used to assist in the maneuvering and positioning of an endoscopy tube or a colonoscopy tube inside a tract of a digestive system of a patient.

Figure 11:
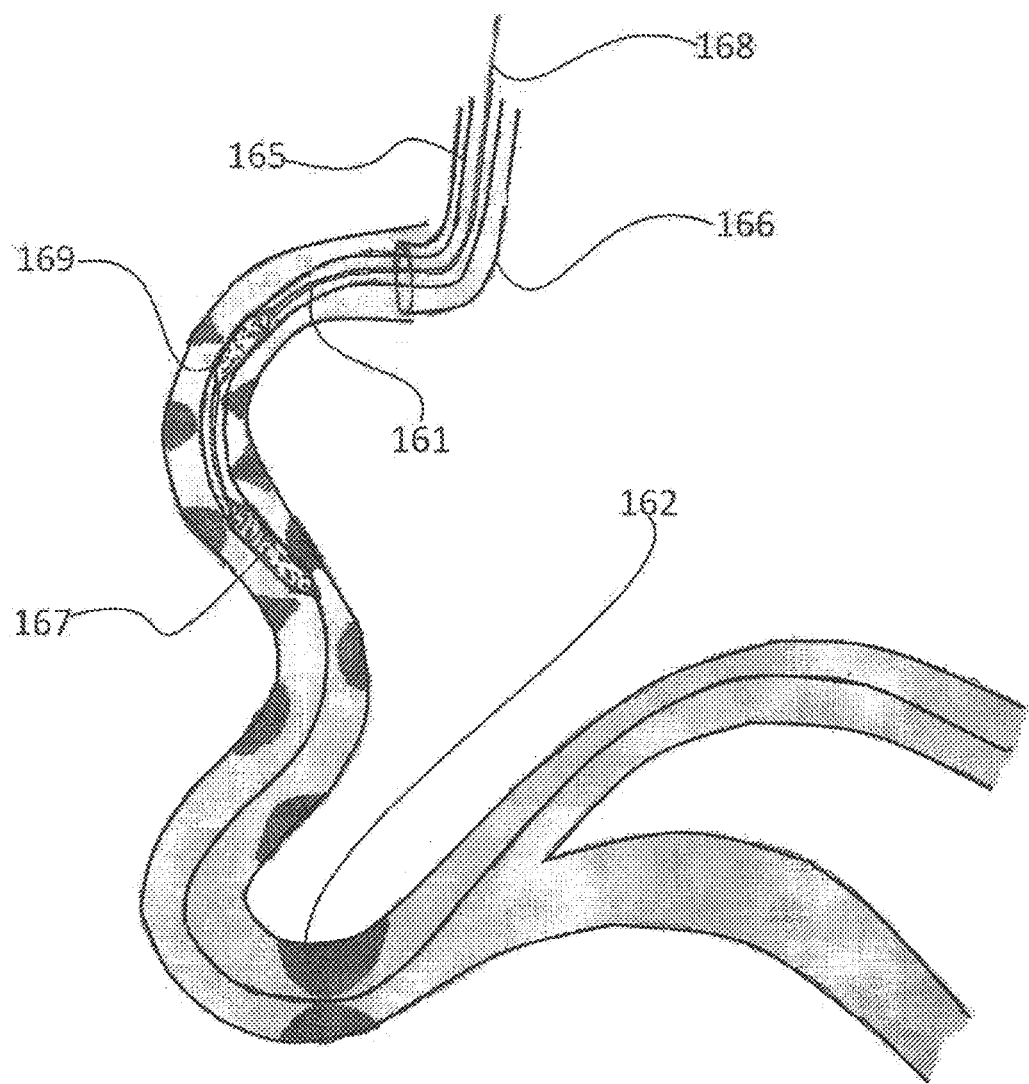
FIG. 11 is a perspective view of a catheter system comprising a mother catheter, an inner support catheter and a transporter catheter advancing through an adverse arterial lumen.
Figure 12:
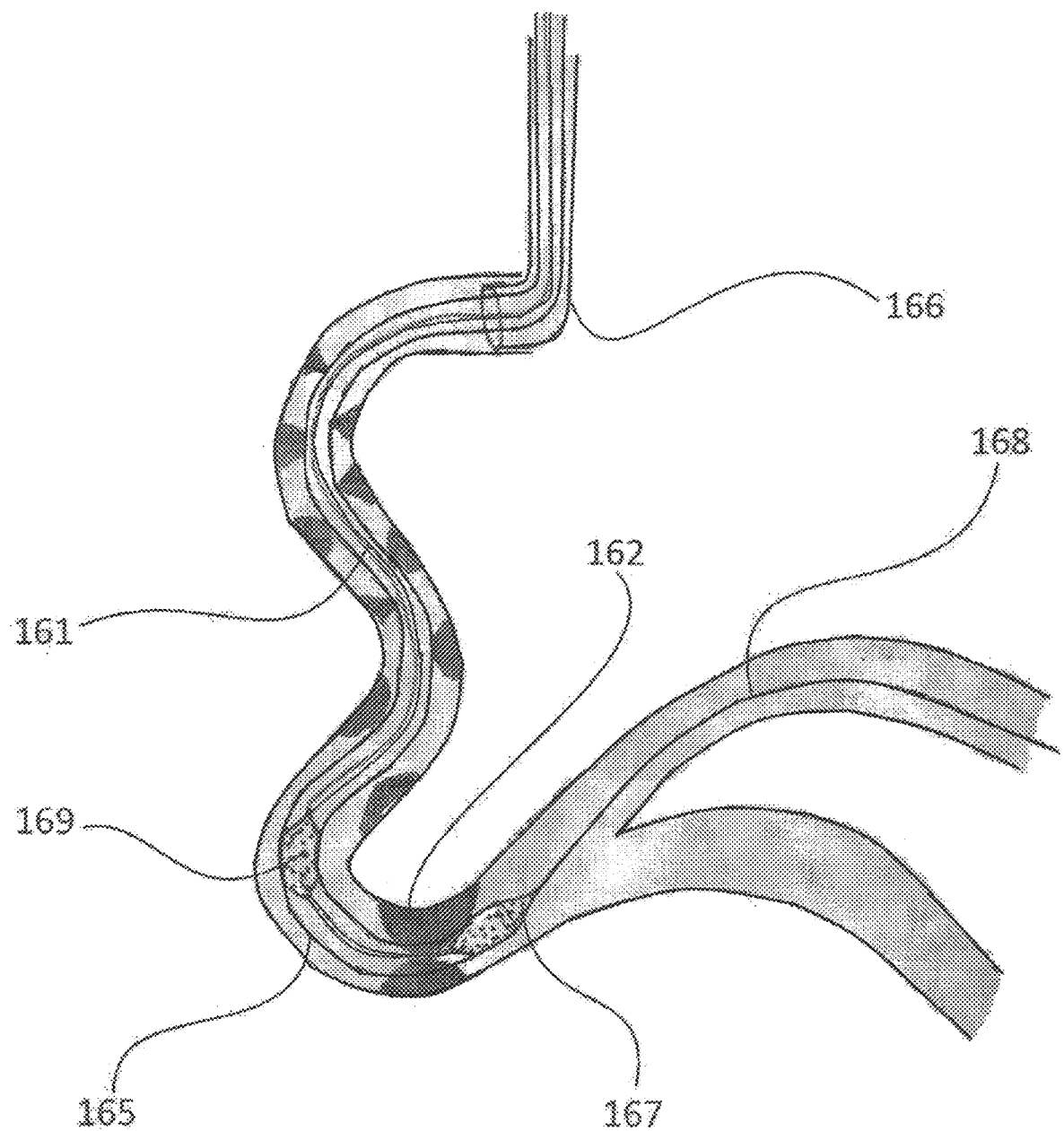
FIG. 12 is a perspective view of a catheter system comprising a mother catheter, an inner support catheter and a transporter catheter that has advanced through an adverse arterial lumen.
Figure 13:
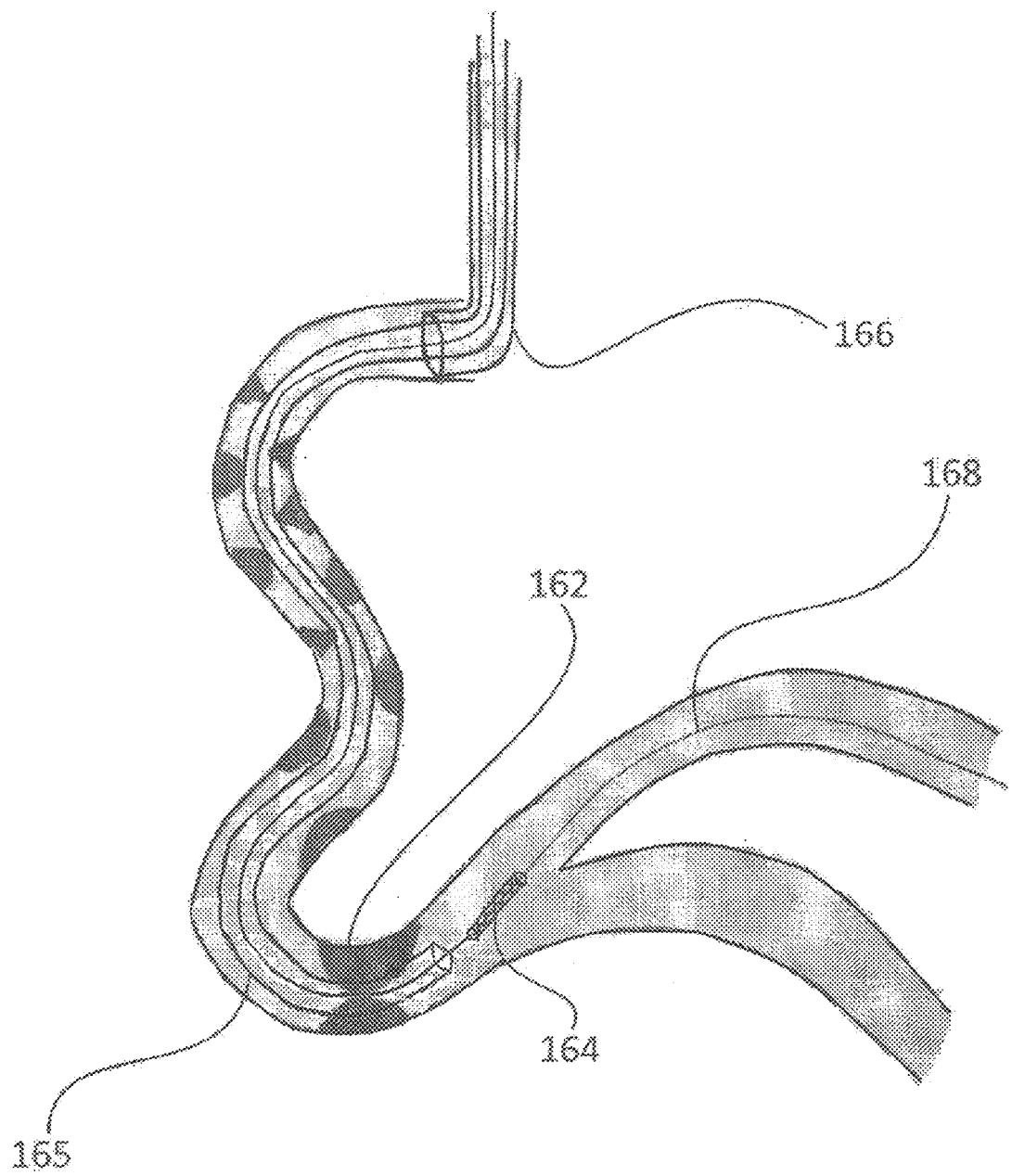
FIG. 13 is a perspective view of positioning of a stent in an adverse arterial lumen using a catheter system comprising a mother catheter, an inner support catheter and a transporter catheter.
Figure 14A:
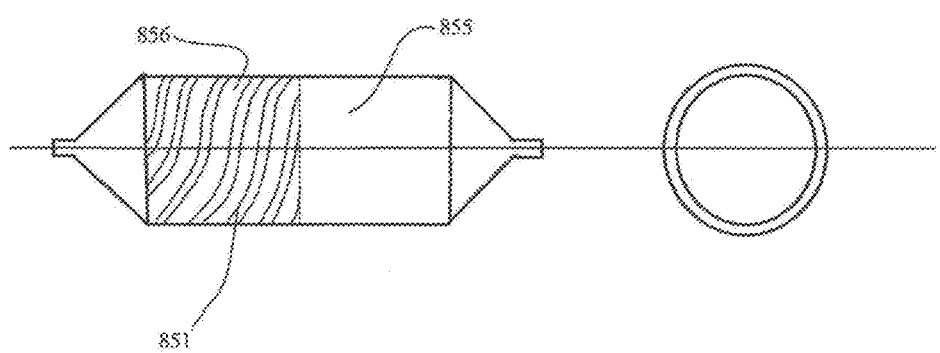
FIG. 14a-d are perspective views of modifications to the surface of the proximal portion of balloon to enhance anchoring of the proximal portion of the balloon to the inner surface of an introducer catheter.
Figure 14B:
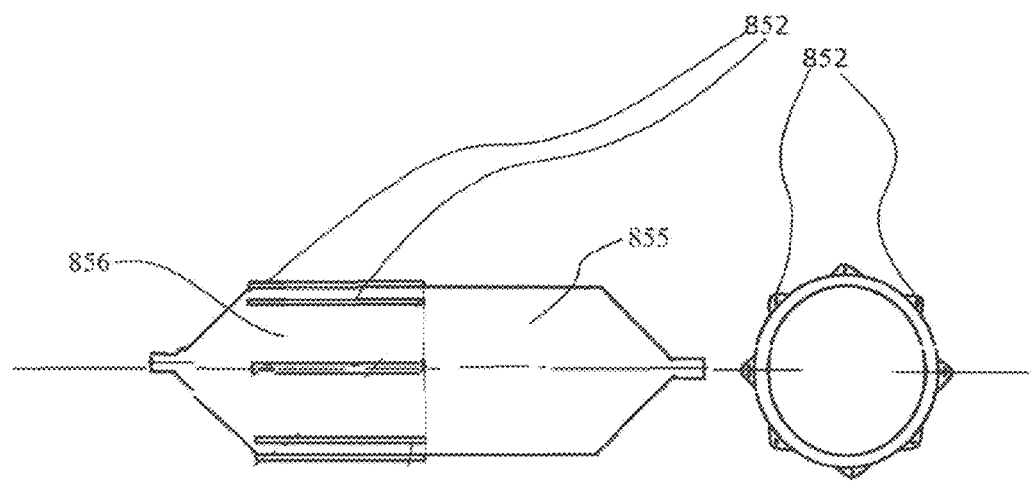
Figure 14C:
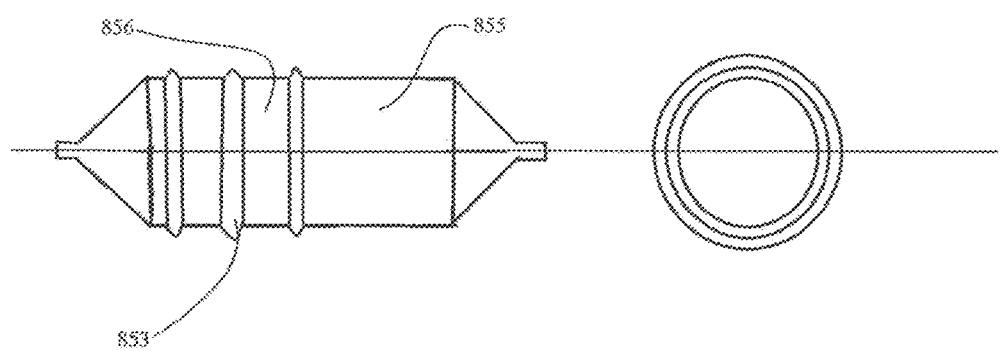
Figure 14D:
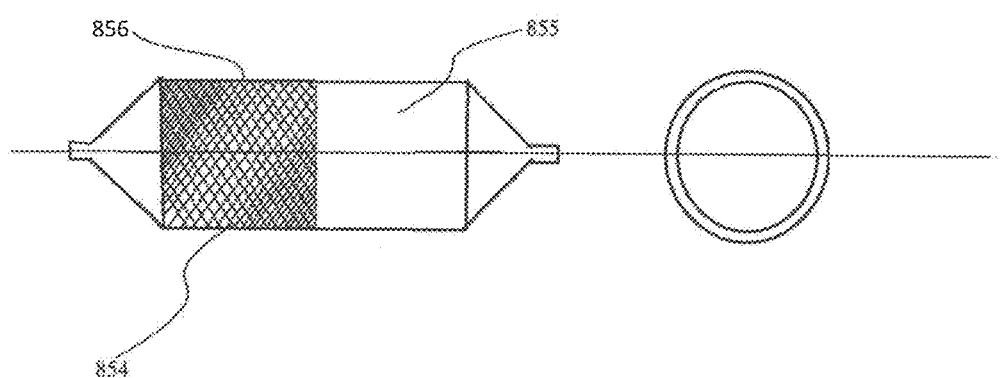

In another embodiment (see FIGS. 11 and 12) comprising a mother catheter 166 and an inner support catheter (daughter or child catheter) 165 advanced on a guidewire 168, the inner support catheter 165 is advanced by placing a transporter catheter 161 inside a lumen of the inner support catheter 165, with the transporter catheter having an orienting balloon 167 protruding from the tip of the inner support catheter and another balloon 169, which is inside the lumen of the inner catheter 165 providing anchoring. Using this multi-balloon transporter catheter 161 to advance the inner catheter 165, the double balloon catheter composite may be advanced through an adverse arterial lumen, beyond the stenosis 162. After the inner support catheter has been successfully placed beyond the stenosis 162, the transporter catheter is withdrawn after deflating the orienting and the anchoring balloons. Then a stent 164 (see FIG. 13) or other hardware may be placed through the inner support catheter 165 distal to the stenosis 162 or in another preferred position. Subsequently the inner support catheter is withdrawn and the stent 164 may be then positioned usually by pulling the stent 164 to the site of interest and deploying the stent 164 (FIG. 13). In one embodiment, at least one hole may be provided in the structure of the inner support catheter to provide for perfusion of blood from outside the inner support catheter into the inner support catheter. In one embodiment, the transporter catheter is inserted in the outer catheter and the orienting balloon is left partially protruding out of the tip of the outer catheter. The orienting balloon is then inflated with sufficient pressure using a fluid to achieve a certain diameter. In one embodiment, the diameter of the inflated orienting balloon is at least equal to the inner diameter of the outer catheter tip. In another embodiment, the diameter of the protruding portion of the orienting balloon is at least equal to the outer diameter of the outer catheter tip. In yet another embodiment, the diameter of the protruding portion of the orienting balloon is greater than the outer diameter of the outer catheter tip. A guidewire may be placed through the orienting balloon before, during or after inflation.

The inner support catheter may include a hydrophilic coating to reduce friction between the arterial lumen and the external surface of the inner support catheter. The wall of the inner support catheter can be made thin whereby the diameter of the inner lumen of the support catheter is large and the outer dimensions of the inner support catheter conforms to the geometry of the coronary artery or other vessels. Because the transporter catheter is used to advance the inner support catheter, the inner support catheter does not require as much structure (such as larger wall thickness) to transmit longitudinal axial forces.

In one embodiment, the transporter catheter has at least one balloon that functions as both the orienting balloon and the anchoring balloon. The transporter catheter comprises a shaft, said shaft comprising a proximal end and a distal end; at least one balloon positioned adjacent to the distal end of the shaft, the at least one balloon (see FIG. 14a-d) comprising a distal portion 855 and a proximal portion 856; the distal portion 855 of the at least one balloon, upon inflation, has a surface configured for smooth movement of the transporter catheter through a patient's vasculature, and the proximal portion 856 of the at least one balloon, upon inflation, has a surface configured for anchoring the transporter catheter to an outer catheter 224 (see FIG. 15); wherein, in operation, the transporter catheter is located within a lumen 226 of the outer catheter 224 and the proximal portion 856 of the at least one balloon upon inflation presses against an inner surface 857 of the lumen of the outer catheter thereby anchoring the transporter catheter 859 near the distal end of the transporter catheter to the outer catheter 224 near a distal end of the outer catheter (see FIG. 15); and, thereafter, when the transporter catheter is pushed and/or torqued to advance the outer catheter to a desired location in the patient's vasculature, the transporter catheter in effect pulls the outer catheter to the desired location in a patient's vasculature. In another embodiment, an interface 858 between the distal portion and the proximal portion of the at least one balloon comprises a radiopaque marker. In yet another embodiment, the distal portion of the at least one balloon is smooth and contoured to assist with smooth advancing of the transporter catheter through the vasculature of the patient's body. In one embodiment, the surface of the distal portion of the at least one balloon is coated with a friction-reduction coating. In another embodiment, the proximal portion of the at least one balloon, after anchoring to the inner surface of the lumen of the outer catheter, reduces slippage or pushback of the transporter catheter backwards into the lumen of the outer catheter when the at least one balloon experiences increased resistance within the patient's vasculature. In yet another embodiment, the surface of the distal portion of the at least one balloon comprises channels for perfusion of blood across the at least one balloon after the at least one balloon is inflated.

Figure 16:
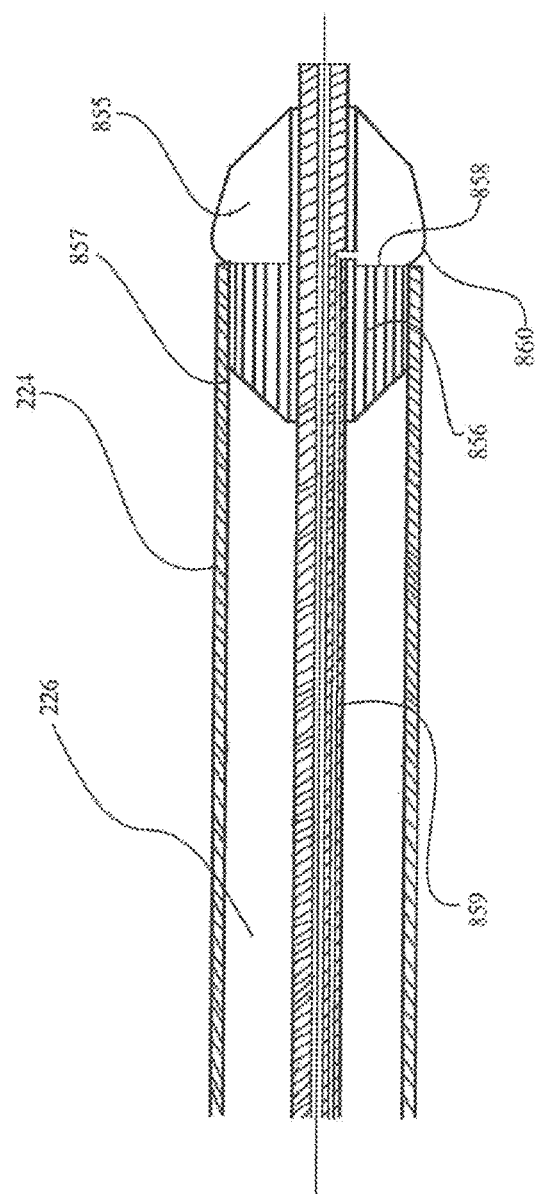
FIG. 16 illustrates a sectional view of a transporter catheter having a balloon having a diameter at a distal portion which, upon inflation, is greater than an outer diameter of the outer catheter.

In one embodiment (see FIG. 16), a diameter of a distal portion 860 of the at least one balloon, upon inflation, is greater than an outer diameter of the outer catheter, thereby substantially reducing or eliminating a potential razor effect of an edge of the outer catheter. In another embodiment, the proximal portion of the at least one balloon anchors the transporter catheter to the outer catheter using a friction-based mechanism between an outer surface of the proximal portion of the at least one balloon and an inner surface of the lumen of the outer catheter. In one embodiment, the friction-based mechanism comprises at least serrations 851 (FIG. 14a) and/or raised projections 852 (FIG. 14b), wherein the serrations and/or the raised projections have shapes comprising spiral 851 (FIG. 14a), linear 852 (FIG. 14b), circular 853 (FIG. 14c), crisscrossed 854 (FIG. 14d) or combinations thereof. In another embodiment, the friction-based mechanism comprises at least an outer layer covering at least partially the outer surface of the proximal portion of the at least one balloon that comes in contact with the inner surface of the lumen of the outer catheter, said outer layer comprising materials providing higher frictional resistance. In one embodiment, the outer layer may comprise of etched polymeric material, e.g., etched polytetrafluoroethylene (PTFE) layer. In another embodiment, a layer of interlaced and/or braided wires may be embedded on the outer surface of the balloon, or the wires may be glued or otherwise connected to the outer surface of the at least one balloon.

Figure 17:
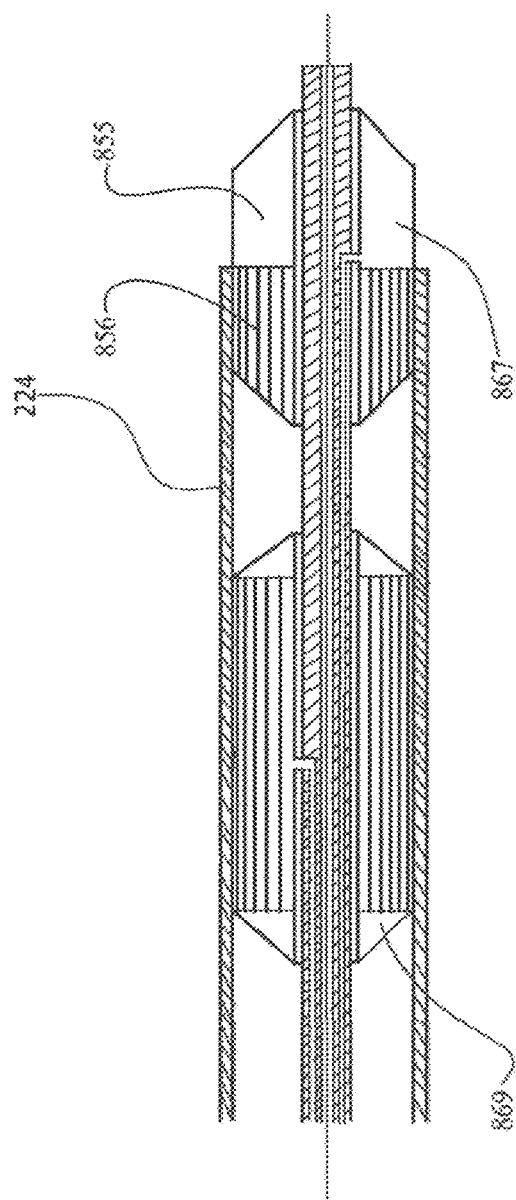
FIG. 17 illustrates a sectional view of a transporter catheter having two balloons, a first balloon with a surface at its distal portion configured for smooth movement through a patient's vasculature and a surface at its proximal portion configured for anchoring to an outer catheter, and a second balloon for additional anchoring to the outer catheter.

In one embodiment, the transporter catheter comprises at least two balloons (see FIG. 17). A first balloon 867 is located near the distal end of the transporter catheter, said first balloon 867 having a distal portion 855 that facilitates the orienting and the maneuvering of the transporter catheter and a proximal portion 856 that anchors the transporter catheter to the inner surface of the outer catheter 224. A second balloon 869 is an anchoring balloon and is located near the first balloon 867. In one embodiment of a method to advance the outer catheter 224, both the first balloon and the second balloon may be inflated separately and independently to anchor the transporter catheter to the outer catheter. Next the transporter catheter is pushed and/or torqued to advance the outer catheter substantially near a location of treatment in a patient's vasculature. Subsequently, the second balloon may be deflated and upon further pushing and/or torqueing of the transporter catheter, the first balloon pulls the distal end of the outer catheter to the location of the treatment site or beyond the treatment site. Subsequently the first balloon may be deflated, and the transporter catheter removed from inside the outer catheter and then a treatment system may be advanced inside the outer catheter to a location at the treatment site or beyond the treatment site. In another embodiment of the method, the first and the second balloon may be deflated, and the transporter catheter may be removed after the outer catheter is advanced to a desired location.

Figure 15:
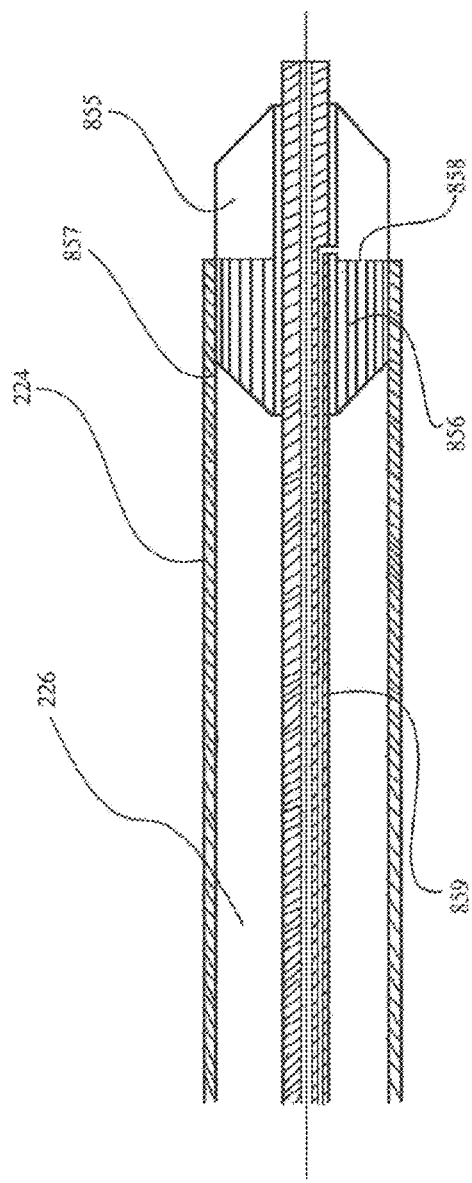
FIG. 15 illustrates a sectional view of a transporter catheter having a balloon with a surface at its distal portion configured for smooth movement through a patient's vasculature and a surface at its proximal portion configured for anchoring to an outer catheter.

FIG. 18a depicts a cross-sectional view of an embodiment of a shaft of the transporter catheter as shown in an embodiment depicted in FIG. 15. The transporter catheter is comprised of a tubular polymeric inner liner 182, a torque-transfer layer 184, a core 186 comprised of a melt-processing polymer, and a heat-shrink layer 188. Lumen 191 provides for passage of a guidewire and lumen 192 provides for inflating or deflating the orienting balloon. FIG. 18b depicts a cross-section view of an embodiment of a shaft of the transporter catheter as shown in an embodiment depicted in FIG. 17. Lumen 193 provides for inflating or deflating the anchoring balloon 869.

Figure 19:
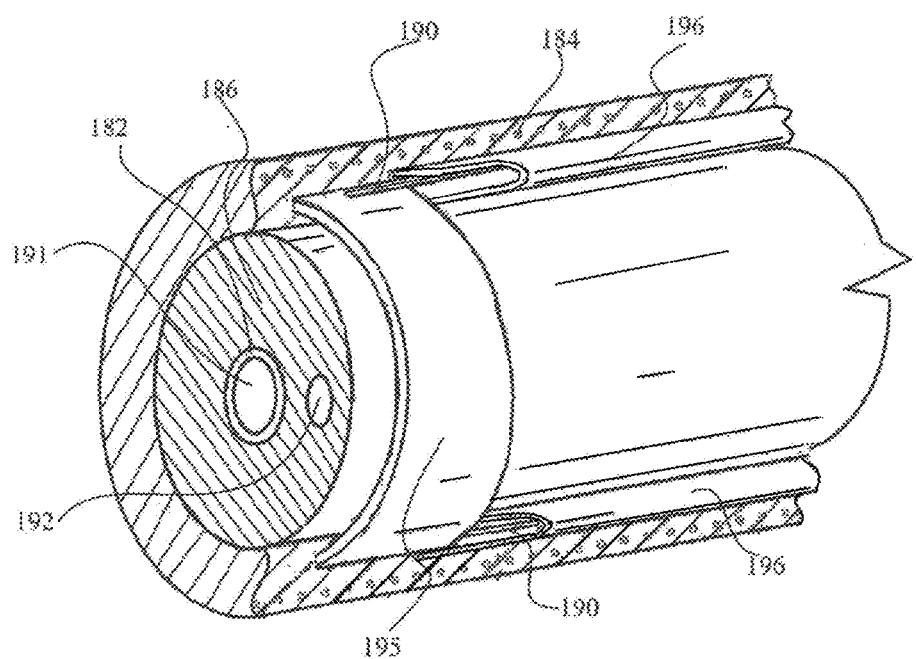
FIG. 19 is a perspective sectional view of a distal end portion of an embodiment of a transporter catheter that is steerable using pull-wires.

In one embodiment, the transporter catheter is steerable using pull-wires. In another embodiment, the pull-wires comprise at least one flat wire 190 disposed longitudinally along the length of the transporter catheter (See FIGS. 18c and 18d). A flat pull-wire 190 typically has a rectangular cross section, though the cross section of the pull-wire need not be perfectly rectangular. In another embodiment, the cross-sectional shape of the pull-wire may be oval or circular. A transporter catheter 100 (see FIG. 1) may include an elongated pull-wire extending through a pull-wire lumen of the shaft 101 of the transporter catheter 100 and terminating within the distal end portion of the shaft. In one embodiment, the pull-wire has a proximal end operatively connected to a handle assembly and a distal end anchored to the distal end portion of the transporter catheter. In another embodiment as shown in FIG. 19, the steerable transporter catheter may include a pull-wire anchor ring or steering ring 195 mechanically coupling a distal end of the pull-wire to the distal end portion of the transporter catheter. In one embodiment, the steering ring 195 may be located at or near the distal end 115 of the anchoring balloon 109. In another embodiment, the steering ring 195 may be located under the anchoring balloon 109. In yet another embodiment, the steering ring 195 may be located near the proximal or the distal end of the orienting balloon 107. In another embodiment, more than one steering ring may be present. In one embodiment, the torque-transfer layer 184 may be disposed between the inner liner 182 and the pull-wire 190. In another embodiment, the torque-transfer layer may be disposed between the pull-wire 190 and the heat-shrink layer 188. In another embodiment, the heat shrink layer may not be present. In one embodiment the pull-wire 190 may be covered with lubricious materials before placement inside the transporter catheter. The lubricious materials comprise silicone and other lubricious materials. In another embodiment, the pull-wire 190 may be smooth and coated with a lubricious layer. In one embodiment, the pull-wire is made of stainless steel. In another embodiment, more than one pull-wire may be used. In another embodiment, two pull-wires may be used and spaced 180 degrees apart (See, e.g., FIG. 18d). In one embodiment, the pull-wires 190 are connected to at least one anchor ring 195 located near the distal end of the introducer (see FIG. 19). The proximal ends of the pull-wires 190 are operably connected to a steering mechanism (not shown) allowing for the steering of the transporter catheter 100 during operation. In one embodiment, a pull-wire may be housed inside a polymeric tube 196 forming a lumen.

In one embodiment, the inner liner 182 is a polymeric material, such as polytetrafluoroethylene (PTFE) or etched PTFE. The inner liner 182 may also be made of other melt-processing polymers, including, without limitation, polyether block amides, nylon and other thermoplastic elastomers. Once such elastomer is Pebax (Pebax is a registered trademark and Pebax is made by Arkema, Inc.). Pebax of various durometers may also be used, including without limitation, Pebax 30D to Pebax 70D. In one embodiment, the core 186 of the shaft is made of an extruded Pebax or PTFE tubing. The melt-processing polymer of the core 186 occupies a plurality of voids of the wire mesh in the torque-transfer layer. The core 186 may also be made of other melt-processing polymers, including, without limitation, etched PTFE, polyether block amides, nylon and other thermoplastic elastomers, of varying durometers. The core 186 may also comprise more than one layer, including, for example, two or more tubes of a melt-processing polymer (see FIG. 19).

In one embodiment, a method for intravascular treatment using a transporter catheter, comprises the steps of: (i) assembling a system comprising a transporter catheter and an outer catheter, the transporter catheter comprising a shaft having at least a first wall, a proximal end, a distal end and at least one internal channel for a guidewire, the outer catheter comprising a substantially cylindrical lumen having a second wall, a proximal end and a distal end, the transporter catheter extending within the lumen of the outer catheter with the distal end of the transporter catheter substantially aligned with the distal end of the outer catheter, an anchoring mechanism displaced in an operative coupling with the transporter catheter and/or the outer catheter whereby the anchoring mechanism anchors at least a distal portion of the transporter catheter to at least a distal portion of the outer catheter, the anchoring mechanism controllably actuated for anchoring or for removal of anchoring of the transporter catheter to the outer catheter; (ii) extending a guidewire along the internal channel of the transporter catheter with a proximal end of the guidewire extending beyond the proximal end of the of the transporter catheter and a distal end of the guidewire extending beyond the distal end of the transporter catheter; (iii) advancing the distal end of the guidewire towards a desired location in a vessel of interest at a treatment site; (iv) controlling said anchoring mechanism to anchor at least the distal portion of the outer catheter to at least the distal portion of the transporter catheter; (v) advancing the system by pushing and/or torqueing at least the transporter catheter along the guidewire towards the treatment site until the system is brought in alignment with or beyond the treatment site; (vi) actuating the anchoring mechanism to remove the anchor hold between the transporter catheter and the outer catheter; (vii) removing the transporter catheter from inside the outer catheter; and (viii) advancing a treatment system inside the outer catheter to a location at the treatment site or beyond the treatment site. In another embodiment, the stiffness of the tip of the transporter catheter is dynamically adjusted in real time by the user by adjusting the pressure of fluid inside the orienting balloon. In yet another embodiment, the stiffness in the distal tip region of the transporter catheter is dynamically adjusted in real time by the user by adjusting the pressure of fluid inside the orienting balloon and/or the anchoring balloon. When a balloon is fully inflated, the stiffness of the balloon increases when the pressure of fluid inside the balloon is increased, and the stiffness of the balloon decreases when the pressure of fluid inside the balloon is decreased. The stiffness of balloon at inflation pressure of 12 atmospheres is greater than the stiffness of balloon at inflation pressure of 4 atmospheres. When the stiffness of the balloon is increased, the stiffness of the treatment system in the region of the balloon increases. For example, when the pressure inside the orienting balloon is increased, the stiffness proximate the tip (tip region) of the treatment system increases. Similarly, when the stiffness of the balloon is decreased, the stiffness of the treatment system in the region of the balloon decreases. For example, when the pressure inside the orienting balloon is decreased, the stiffness proximate the tip (tip region) of the treatment system decreases. Dynamic variation and control of stiffness of the treatment system using orienting balloon and anchoring balloon may be done in real time when advancing the treatment system through a patient's vasculature during a procedure by adjusting pressures in the balloons to navigate complex physio-anatomy. More than one anchoring balloon may be used (see FIG. 5) whereby the stiffness of the treatment system may be dynamically varied and controlled over an extended length of the treatment system beyond the tip region of the treatment system.

Figure 21A:
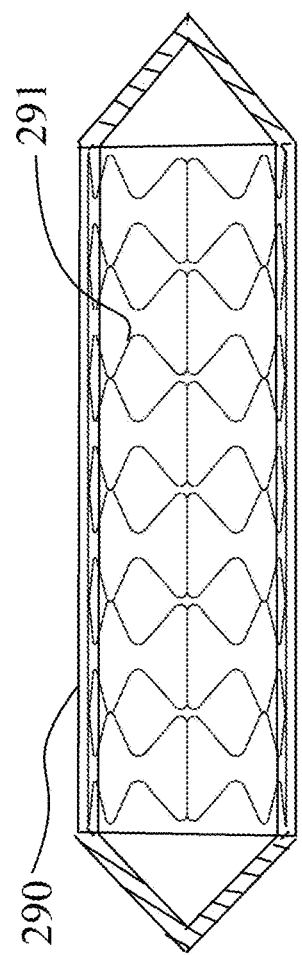
FIG. 21a-b are perspective views of balloons having a web or a coil embedded in the wall of the balloon to facilitate rewrapping of the balloons upon deflation of the balloons.
Figure 21B:
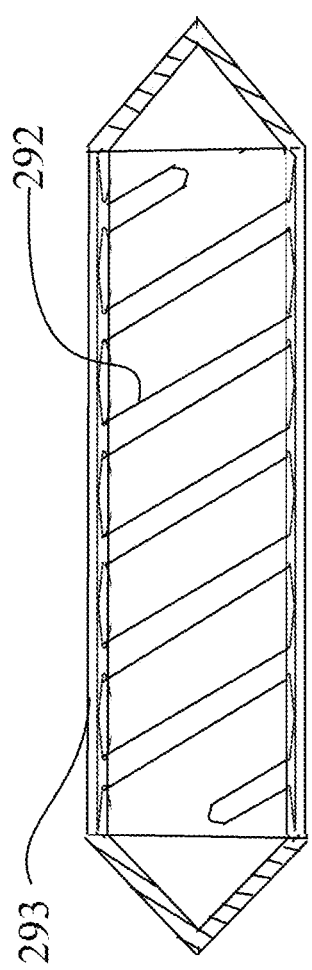

In one embodiment, the transporter catheter 100 is manufactured via an extrusion process. Given that extrusion processes are well known in the art, the general process is not discussed in detail herein. In general, the extrusion process begins by heating the polymer until melted. The melted polymer is then forced under pressure through an extrusion tip and die. As the melted polymer exits the extrusion tip and die, it is cooled. A typical cooling method employs a water bath. The cooling step solidifies the device with the desired dimensions. An aspect of the invention is withdrawing or removing the transporter catheter from inside the outer catheter after the outer catheter is advanced to a location of interest or treatment inside a patient's vasculature. Before withdrawing the transporter catheter, the orienting balloon 107 and the anchoring 109 balloon are deflated. Upon deflation, the orienting balloon 107 and the anchoring balloon 109 are configured or have structures that minimize the contact of the balloon outer surface with the inner surface of the outer catheter. When withdrawing the transporter catheter, the dynamic frictional force between the outer surface of the balloons (i.e., the orienting balloon 107 and/or the anchoring balloon 109) is less than the static frictional force between the outer surface of the outer catheter and the inner surface of the patient's vasculature. Frictional pull created by the orienting balloon 107 and the anchoring balloon 109 on the inner surface of the outer catheter while the transporter catheter is being withdrawn does not significantly move the outer catheter from its position at the location of interest. In one embodiment, the orienting balloon 107 and/or the anchoring balloon 109 can be rewrapped to substantially its pre-inflation structure after an inflation-deflation cycle thereby minimizing the contact of the balloon outer surface with the inner surface of the outer catheter. In another embodiment, the orienting balloon 107 and/or the anchoring balloon 109 has a pleated configuration (see FIG. 20) that facilitates rewrapping of the balloon. FIG. 20a depicts an anchoring balloon 109 wrapped in a pleated configuration around the shaft 101. FIG. 20b depicts the pleated balloon as it is being inflated or deflated, and FIG. 20c depicts a fully inflated balloon. In another embodiment, the wall 290 of the balloon comprises a web 291 that expands as the balloon expands upon introduction of a fluid in the balloon and the web 291 contracts when the fluid is withdrawn from the balloon (see FIG. 21a). The contraction of the web facilitates rewrapping of the balloon. In another embodiment, the wall 293 of the balloon may comprise a spring-like coil 292 that stretches when the balloon expands and the coil 292 returns substantially to its original shape when the balloon contracts (see FIG. 21b). The returning of the coil to its original shape facilitates in rewrapping the balloon substantially to its original structure. The web or the coil may be made of metal, metal alloy or plastic. Nitinol may be used in the construction of the web or the coil.

Figure 22:
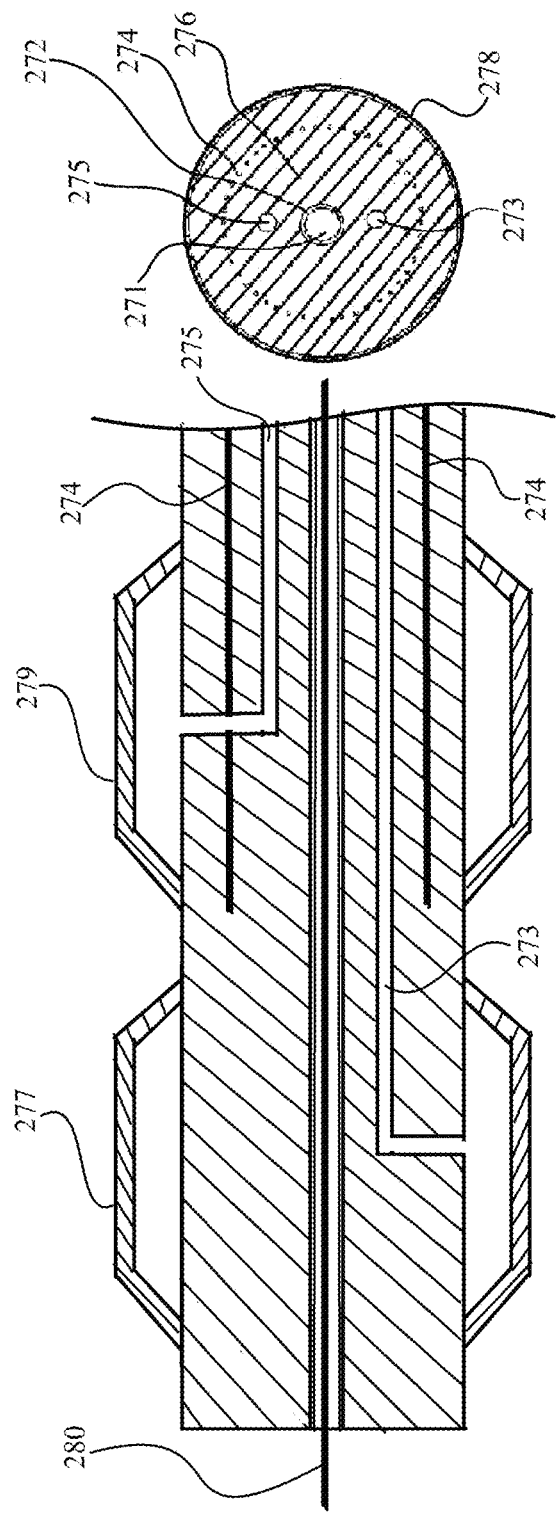
FIG. 22 illustrates a sectional view of the shaft of the transporter catheter.

FIG. 22 depicts a perspective sectional front view and sectional end view of an embodiment of a shaft of the transporter catheter. The shaft of the transporter catheter is comprised of a tubular polymeric inner liner 272, a torque-transfer layer 274, a core 276 comprised of a polymer, and a heat-shrink layer 278. Lumen 271 provides for passage of a guidewire 280, and lumen 273 provides for inflating or deflating the orienting balloon 277. Lumen 275 provides for inflating or deflating the anchoring balloon 279. In one embodiment, the torque-transfer layer 274 extends from the proximal end 102 of the catheter 100 up to distal end 115 of the anchoring balloon 109 (see FIG. 1 and FIG. 22). In another embodiment, the torque-transfer layer 274 extends from the proximal end 102 of the catheter 100 to the distal end 103 of the catheter (not shown).

Figure 23:
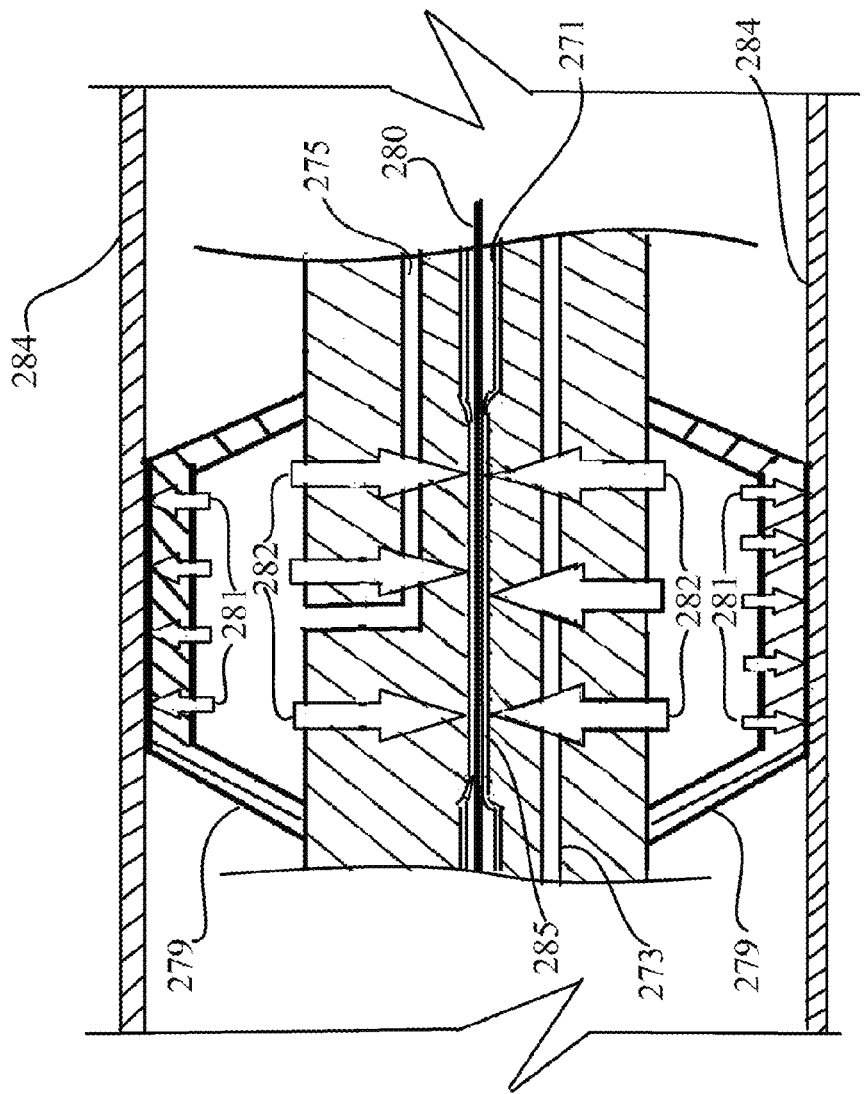
FIG. 23 is a view of an inflated anchoring balloon illustrating the forces exerted on the shaft of the transporter catheter.
Figure 24A:
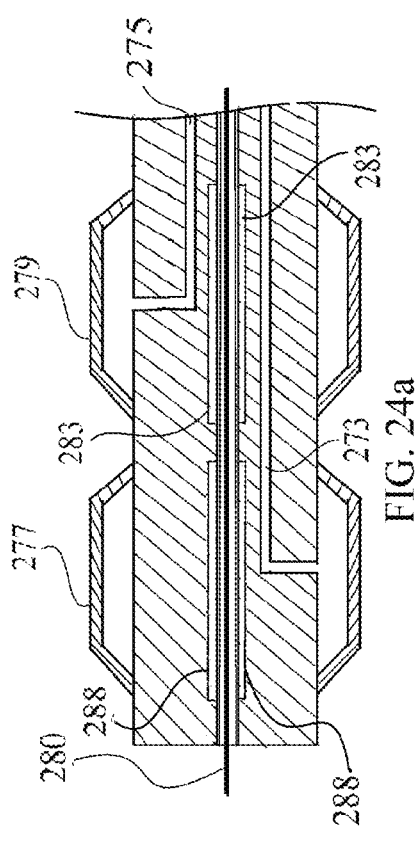
FIG. 24a-b depict sectional views of the shaft of the transporter catheter illustrating reinforcements underlying the anchoring balloon and the orienting balloon to prevent locking of the transporter catheter to the guidewire.
Figure 24B:
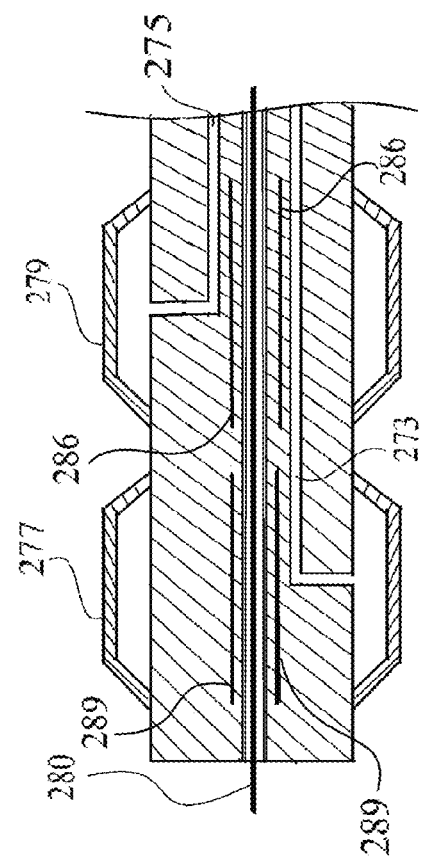

When the anchoring balloon 279 is inflated, it exerts pressure 281 on the inner surface of the outer catheter 284 (see FIG. 23). The fluid in the inflated anchoring balloon 279 also exerts pressure 282 on the shaft underlying the anchoring balloon. The pressure 282 on the shaft may compress the shaft and lead to narrowing and constriction 285 of the guidewire lumen 271 underlying the anchoring balloon. Consequently, the inflation of the anchoring balloon 279 may result in locking of the transporter catheter to the guidewire 280. However, the transporter catheter has to be able to track or move over the guidewire 280 with the anchoring balloon 279 inflated. To allow the transporter catheter to track over the guidewire 280 with the anchoring balloon 279 inflated, in one embodiment of the invention, at least a portion of the guidewire lumen 271 underlying the anchoring balloon is provided with reinforcement to prevent the guidewire lumen 271 from narrowing when the anchoring balloon 279 is inflated. In another embodiment, the entire guidewire lumen 271 is reinforced to prevent locking of the transporter catheter to the guidewire when the anchoring balloon and/or the orienting balloon is inflated. In one embodiment, the reinforcement of the guidewire lumen 271 is done by having the tubular inner liner 272 made of a material that is more rigid than the material of the core 276 of the shaft. In another embodiment, the reinforcement of the guidewire lumen underlying the anchoring balloon may be done by including a tube 283 made of a stiff material to encapsulate the guidewire lumen underlying the anchoring balloon (see FIG. 24a). Materials used to provide greater rigidity or stiffness may vary widely. Examples of the materials include PTFE, high density polyethylene, polyimide, and composites of these materials. In yet another embodiment, the reinforcement of the guidewire lumen underlying the anchoring balloon may be done by including a cylindrical braided-wire plait matrix 286 embedded in the core 276 of the shaft and located proximate to the guidewire lumen 271 (see FIG. 24b). In another embodiment, the guidewire lumen underlying the orienting balloon may also be provided reinforcement 288, 289 in a manner similar to reinforcing of the guidewire lumen underlying the anchoring balloon. In another embodiment, the torque-transfer layer 274, 184 is designed to function also as a reinforcement layer that prevents constriction of the guidewire lumen 271 when the anchoring balloon 279 and/or the orienting balloon 277 are pressurized. In yet another embodiment, a wire-based reinforcement may be provided at least in a portion of the shaft underlying the anchoring balloon 279. In one embodiment, the wire-based reinforcement may be in the form of a helical coil 255 (see FIG. 25a). In another embodiment, the wire-based reinforcement may be in the form of a plait-matrix 256 (see FIG. 25b). The wire-based reinforcement may be proximate to the outer surface 257 of the shaft. In yet another embodiment, the entire length of the guidewire lumen 271 may be reinforced, e.g., with a cylindrical braided-wire plait matrix. In one embodiment of the invention shown in FIG. 15, only a portion of the guidewire lumen underlying the anchoring portion 856 of the balloon is reinforced.

Figure 27A:
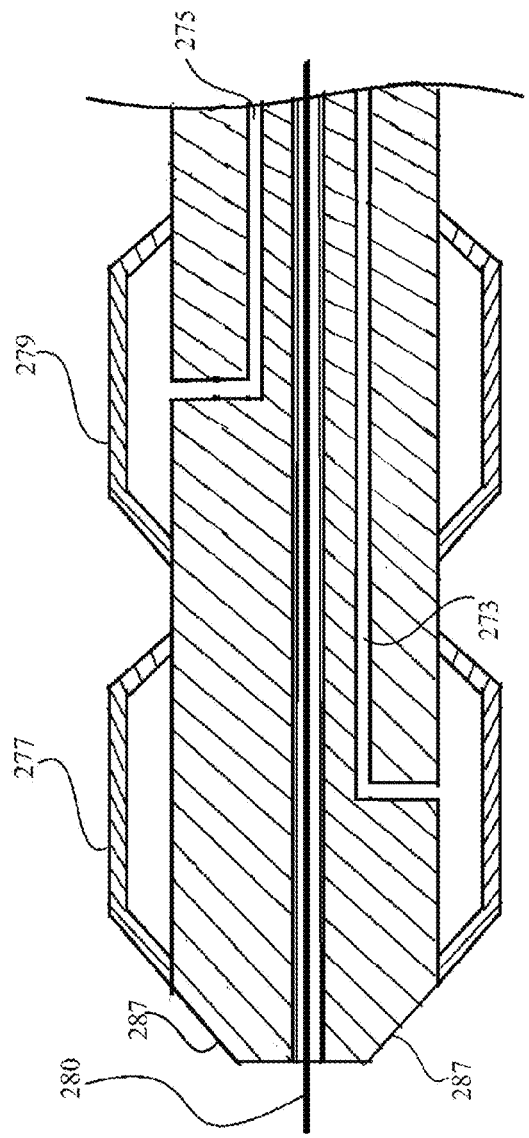
FIG. 27a-b are schematic sectional views of distal end of the shaft of the transporter catheter showing tapered and contoured distal end of the shaft.
Figure 27B:
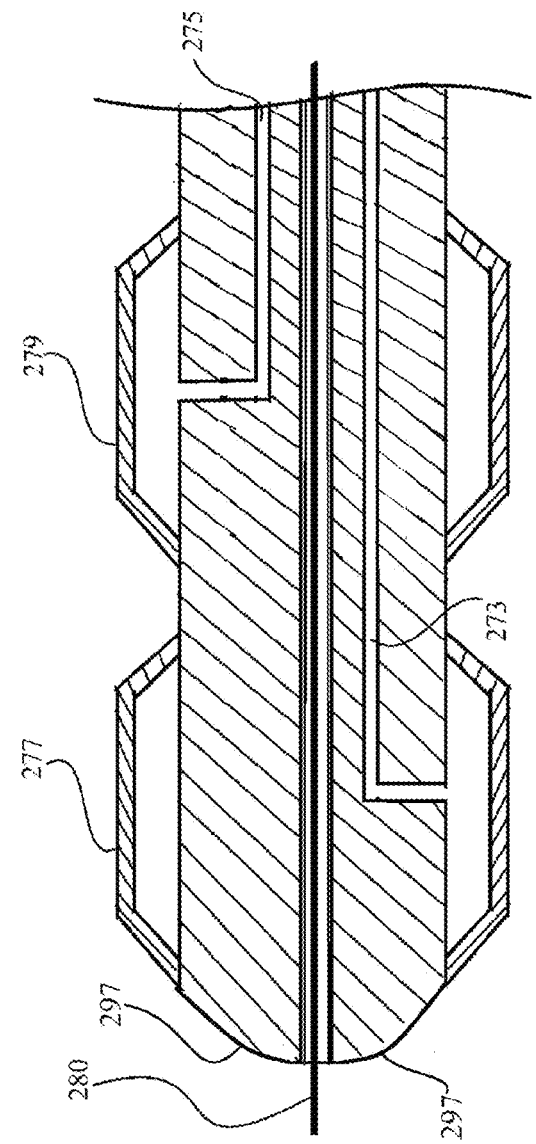

In another embodiment of the invention (see FIG. 26), the lumen 273 provided for inflating and deflating of the orienting balloon 277 is reinforced at least in a portion underlying the anchoring balloon. When the anchoring balloon is inflated, the fluid in the anchoring balloon exerts pressure on the shaft. If the shaft is compressible, the lumen 273 underlying the anchoring balloon may be narrowed and constricted because of the pressure of the fluid in the anchoring balloon. A constriction in the lumen 273 would make operation of the orienting balloon difficult for a user. The portion of the lumen 273 underlying the anchoring balloon may be reinforced by encapsulating in a tube 294 made of a material that is more rigid than the material of the core 276 of the shaft. In another embodiment, the reinforcement of the lumen 273 underlying the anchoring balloon may be done by including a cylindrical braided-wire plait matrix 295 embedded in the core 276 of the shaft and located proximate to the lumen 273 (see FIG. 25). In another embodiment, the distal end 103 of the shaft 101 has a taper 287 (see FIG. 27a) or a contour 297 (see FIG. 27b). The tapering and/or the contouring of the distal end 103 of the shaft 101 is done to minimize razor effect on the patient's vasculature due to the distal end 103 of the shaft 101 as the transporter catheter is advanced in the patient's vasculature.

Figure 28:
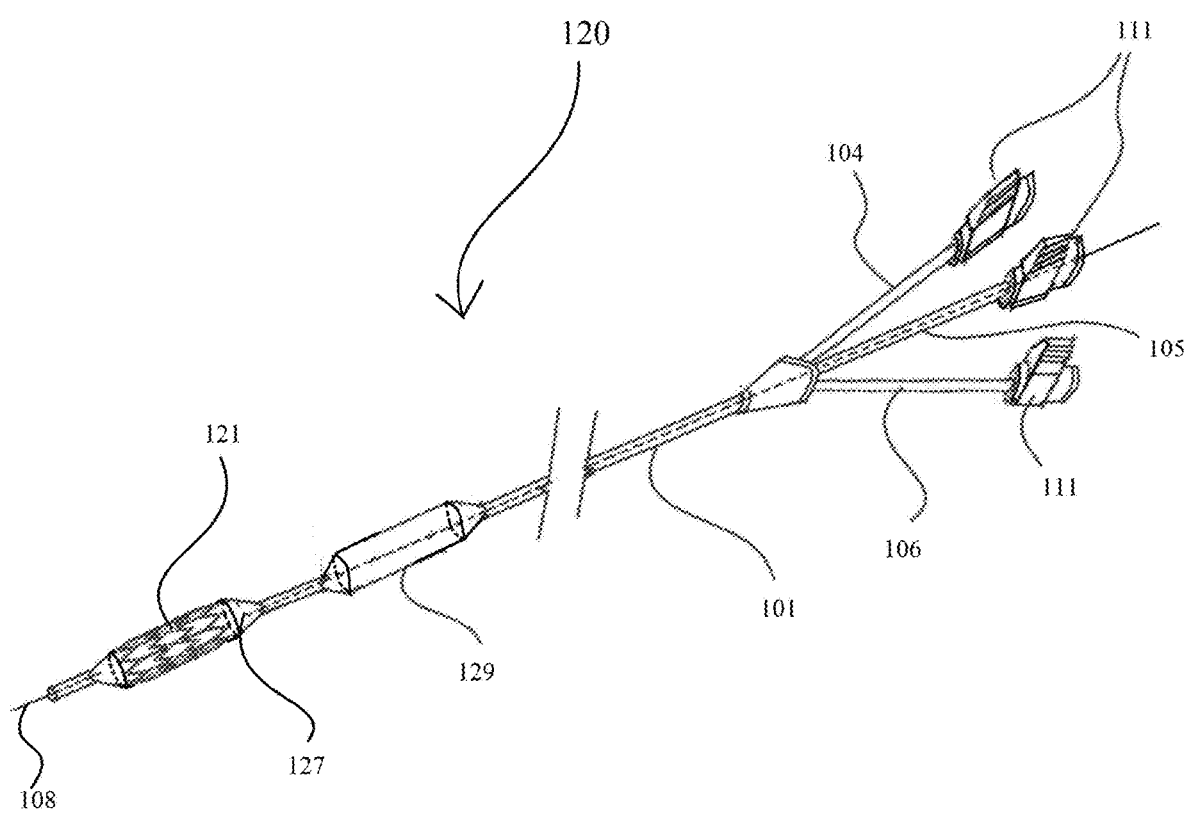
FIG. 28 is a perspective view of a transporter catheter in accordance with one embodiment of the present invention showing a heart valve disposed on a first balloon.

Another embodiment of the present invention provides a heart valve delivery system for delivery of a prosthetic (i.e., replacement) heart valve to a native valve site within a patient's vasculature. In yet another embodiment, the transporter catheter may be used to deliver tools to a target location in a patient's body. In one embodiment, the system advances a prosthetic valve through an aorta for replacing a stenotic aortic valve. The prosthetic valve may be disposed over the orienting balloon at the distal end portion of the transporter catheter. FIG. 28 depicts a prosthetic heart valve mounted on the orienting balloon at the distal end portion of the transporter catheter. The system of the present invention may be configured to deliver the prosthetic heart valve to one of the native valves of the heart (e.g., the aortic, mitral, pulmonary, or tricuspid valves).

In one embodiment, a method for intravascular treatment using a transporter catheter, comprises the steps of: (i)

assembling a system comprising a transporter catheter and an outer catheter, the transporter catheter comprising a shaft having at least a first wall, a proximal end, a distal end and at least one internal channel for a guidewire, the outer catheter comprising a substantially cylindrical lumen having a second wall, a proximal end and a distal end, the transporter catheter extending within the lumen of the outer catheter with the distal end of the transporter catheter substantially aligned with the distal end of the outer catheter, an anchoring balloon displaced in an operative coupling with the transporter catheter whereby the anchoring balloon anchors at least a distal portion of the transporter catheter to at least a distal portion of the outer catheter, the anchoring balloon controllably inflated for anchoring or deflated for removal of the anchoring of the transporter catheter to the outer catheter; (ii) extending a guidewire along the internal channel of the transporter catheter with a proximal end of the guidewire extending beyond the proximal end of the of the transporter catheter and a distal end of the guidewire extending beyond the distal end of the transporter catheter; (iii) advancing the distal end of the guidewire towards a desired location in a vessel of interest at a treatment site; (iv) inflating said anchoring balloon to anchor at least the distal portion of the transporter catheter to at least the distal portion of the outer catheter; (v) advancing the system with the anchoring balloon inflated by pushing and/or torqueing at least the transporter catheter along the guidewire towards the treatment site until the system is brought in alignment with or beyond the treatment site; (vi) deflating the anchoring balloon to remove the anchor hold between the transporter catheter and the outer catheter; (vii) removing the transporter catheter from inside the outer catheter; and (viii) advancing a treatment system inside the outer catheter to a location at the treatment site or beyond the treatment site, wherein the guidewire lumen underlying the anchoring balloon is configured not to constrict under pressure from the pressurized fluid in the inflated anchoring balloon thereby not locking the transporter catheter to the guidewire and allowing the transporter catheter to track and advance on the guidewire while the anchoring balloon is pressurized and inflated. In another embodiment, the transporter catheter is tracked and advanced on the guide wire while both the anchoring balloon and the orienting balloon are pressurized and inflated.

Shaft 101 and lumens 104, 105 and 106 may be manufactured using any commercially available catheter materials. Materials may include, without limitation, polyethylene, polyamide, and urethane. It may be also possible to use polyolefin, such as polypropylene; polyesters including polyamide and polyethylene terephthalate; fluorine-based polymer including PTFE (polytetrafluoroethylene); PEEK (polyether ether ketone); polyimide; synthetic resin elastomers including an olefinic elastomer (e.g., a polyethylene elastomer and a polypropylene elastomer), polyamide elastomer, styrenic elastomer (e.g., a styrene-butadiene-styrene copolymer, a styrene-isoprene-styrene copolymer, a styrene-ethylene butylene-styrene copolymer); polyurethane, urethane-based elastomer, and fluorine-based elastomer; synthetic rubber, including urethane rubber, silicone rubber, and butadiene rubber. The material chosen will depend on the end use of the catheter, the size of the vessel to be accessed, and/or whether or not a stylet or stylets will be used to assist during insertion and advancement of the catheter system. The desired end use will determine the degree of stiffness, flexibility, strength and/or slipperiness of the material(s) to be used. Orienting balloon 107 and anchoring balloon 109, may be manufactured using any commercially available balloon materials. Materials include, without limitation, latex, silicone, ethylvinylacetate, and urethane.

In another embodiment, the transporter catheter is configured to perform a diagnostic, therapeutic, or interventional procedure where access to a target location inside a patient's body is desired. For example, the transporter catheter can be used to deliver and deploy a prosthetic device in the body, to deliver tools to a target location in the body, or to deliver or introduce drugs or other agents, to name a few exemplary uses.

Figure 29:
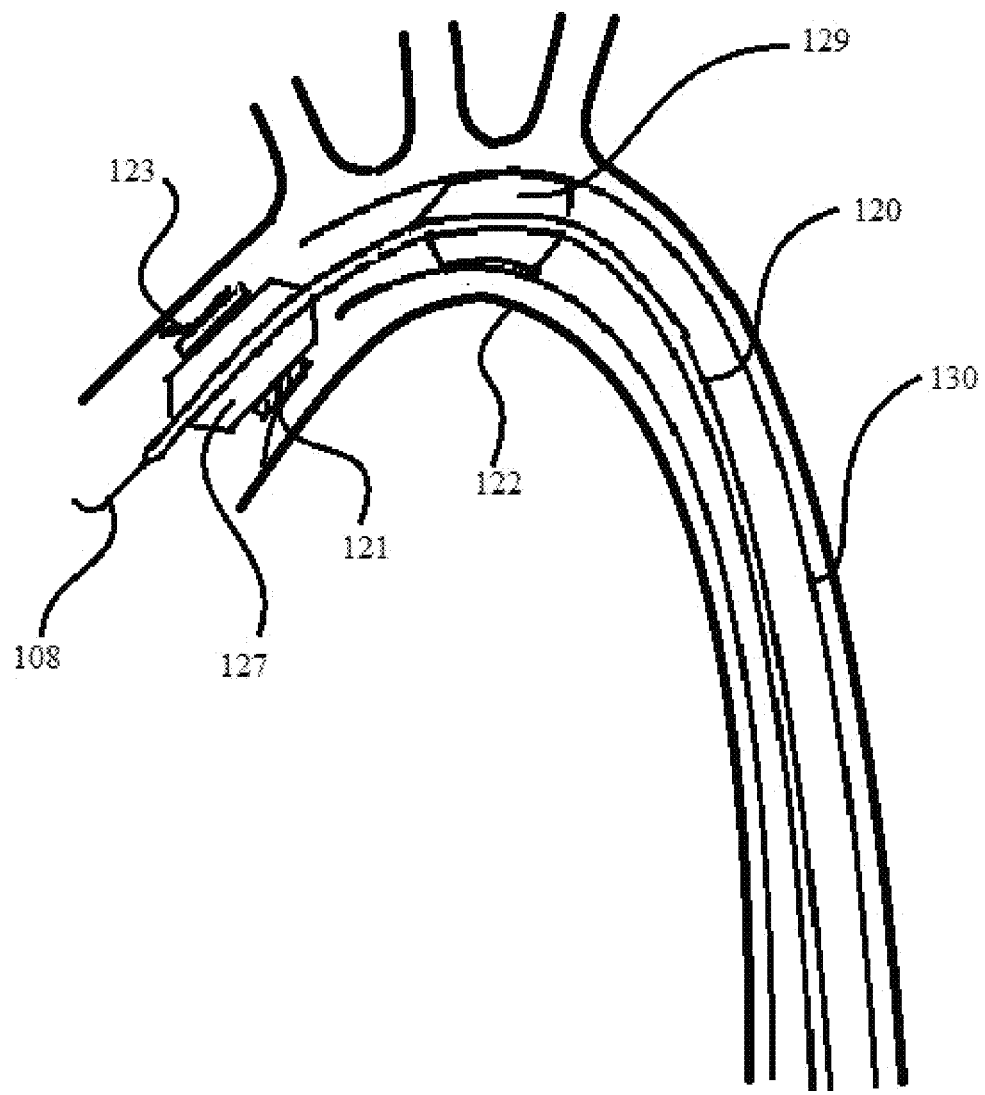
FIG. 29 is a perspective view of heart valve delivery system that has been advanced to a diseased valve.

In one embodiment (see FIG. 28), the first balloon 127 of the transporter catheter 120 is configured to deliver a prosthetic valve 121 to a native valve site. An expandable prosthetic valve 121 is disposed over the first balloon 127. The transporter catheter 120 is placed inside an outer catheter 130 to form a heart valve delivery system (See FIG. 29). The anchoring balloon 129 of the transporter catheter 120 anchors the transporter catheter 120 to the outer catheter 130 whereby the heart valve delivery system can be advanced through a patient's vasculature as a single unit over a guidewire 108. In one embodiment, the prosthetic valve 121 is crimped over the first balloon 127. In another embodiment, the first balloon 127 holds the prosthetic valve in place inside the outer catheter 130 when the first balloon 127 is pressurized to a first pressure and the first balloon 127 deploys the prosthetic valve 121 when the first balloon is pressurized to a second pressure, wherein the second pressure is greater than the first pressure.

Figure 30:
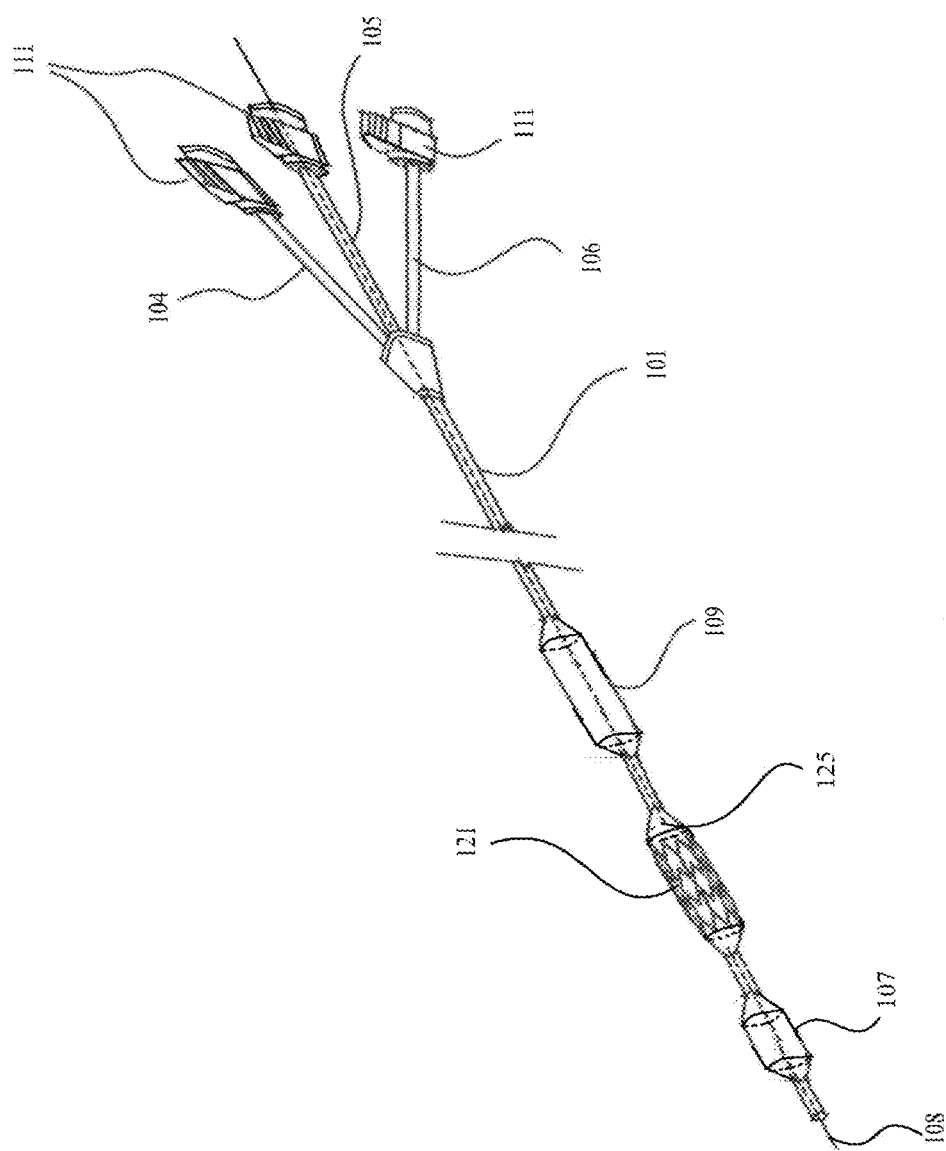
FIG. 30 is a perspective view of a transporter catheter in accordance with one embodiment of the present invention showing a heart valve disposed on a balloon located between an orienting balloon and an anchoring balloon.

In another embodiment (see FIG. 30), the prosthetic valve 121 is disposed over a second balloon 125 located between an orienting balloon 107 and an anchoring balloon 109 (see FIG. 30). In one embodiment, the orienting balloon 107 and the second balloon 125 are connected by a single lumen for inflation and deflation whereby the orienting balloon and the second balloon can be inflated and deflated at the same time. In another embodiment, the orienting balloon 107 has a first lumen for inflation and deflation and the second balloon 125 has a second lumen for inflation and deflation, whereby the orienting balloon 107 and the second balloon 125 can be inflated and deflated independently of each other. In one embodiment, the diameter of the orienting balloon 107 is smaller than the diameter of the second balloon 125. In another embodiment, the length of the orienting balloon 107 is in the range of 10 mm to 20 mm. In yet another embodiment, the length of the orienting balloon 107 is less than the length of the second balloon 125. In another embodiment, the diameter of the orienting balloon 107 is in the range of 4-10 mm. In another embodiment, the diameter of second balloon 125 is in the range of 20 mm-30 mm. In one embodiment, the valve is crimped on the second balloon 125 whereby the diameter of the crimped valve is less than 10 mm.

In one embodiment, the outer catheter is steerable. In another embodiment, the transporter catheter is steerable. In yet another embodiment, both the transporter catheter and the outer catheter are steerable. In one embodiment, the transporter catheter has a steerable section that is actuated by one or more pull-wires. In one embodiment, the outer catheter has a steerable section that is actuated by one or more pull-wires. In another embodiment, two pull-wires may be symmetrically located at opposite ends of a diameter of the transporter catheter and/or the outer catheter. In yet another embodiment, the two pull-wires may be eccentrically located, i.e., the two pull-wires are not located at the opposite end of a diameter of the transporter catheter and/or the outer catheter. In one embodiment, the steerable section comprises a flexible metal or plastic tube that has a plurality of notches to facilitate bending of the flexible tube. In another embodiment, the flexible tube is a plastic or a stainless-steel hypo-tube, which is known in the art. In one embodiment, the flexible tube is embedded in the polymeric structure of the catheter.

Figure 31:
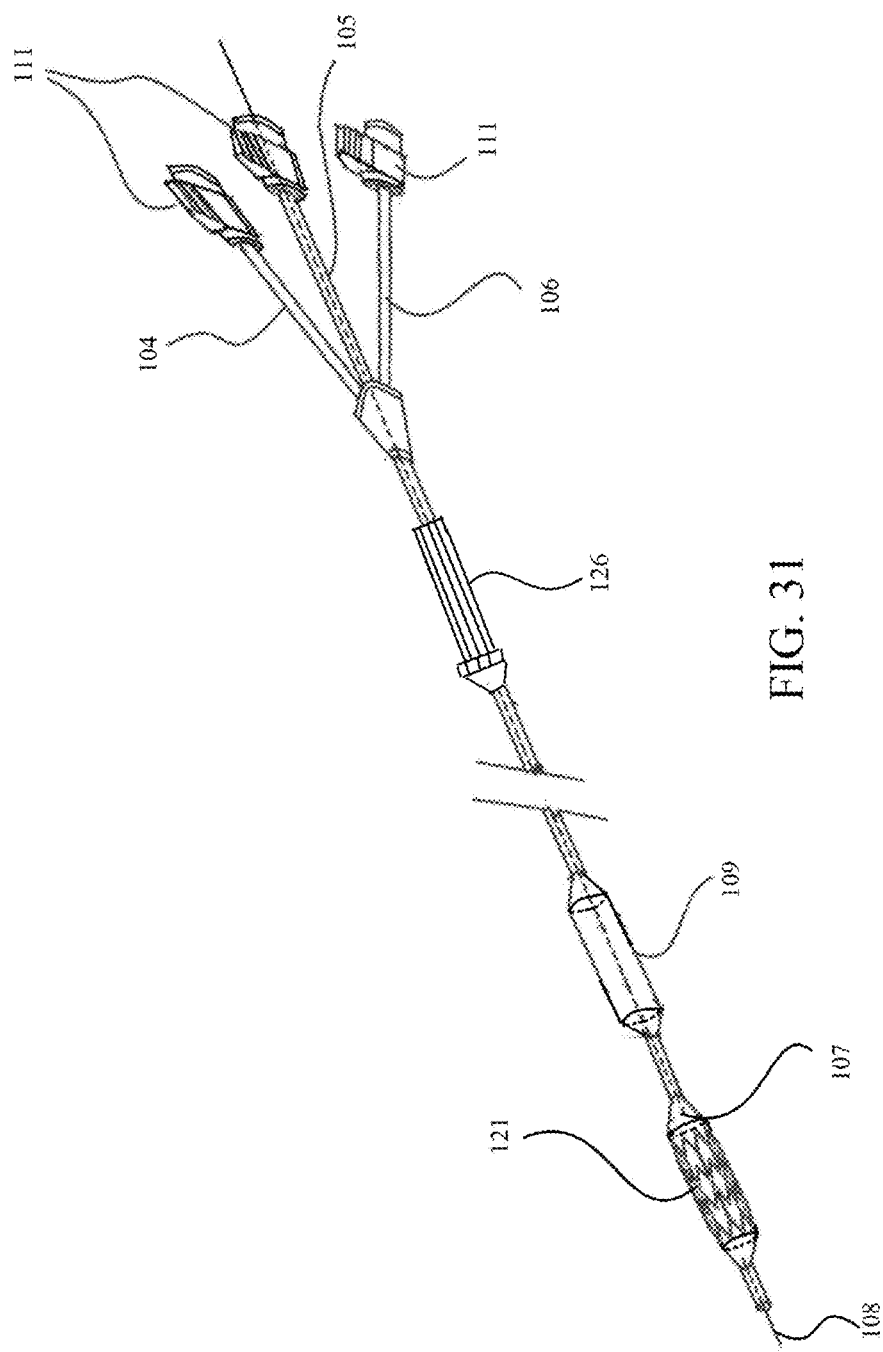
FIG. 31 is a perspective view of a transporter catheter in accordance with one embodiment of the present invention showing a handle connected to pull-wires.

In one embodiment, the steerable section of the transporter catheter comprises a flexible tube (e.g., a hypo-tube) and/or a ring. At least one pull-wire is connected to the flexible tube and/or the ring at the distal end of the pull-wire. The proximal end of the pull-wire is connected to a movable member of a handle 126 (see FIG. 31). A linear or a rotational motion of the moving member results in a pull-force being applied to the pull-wire. When the pull-wire is pulled using the handle 126, the pull-wire draws the portion of the flexible tube that is connected to the pull-wire towards the handle 126. If the pull-wire is connected to a ring, the pull-wire draws the side of the ring to which the pull-wire is connected toward the handle 126. The side of the catheter through which the pull-wire is being pulled bends. The steerable section has a first configuration wherein the steerable section is substantially straight and a second configuration wherein the steerable section is curved. The steerable section is enveloped by a covering, wherein the covering is stretchable such that it biases the steerable section from the second configuration to the first configuration. The covering is preferably formed with a soft durometer polyether block amide known as Pebax.

Figure 32:
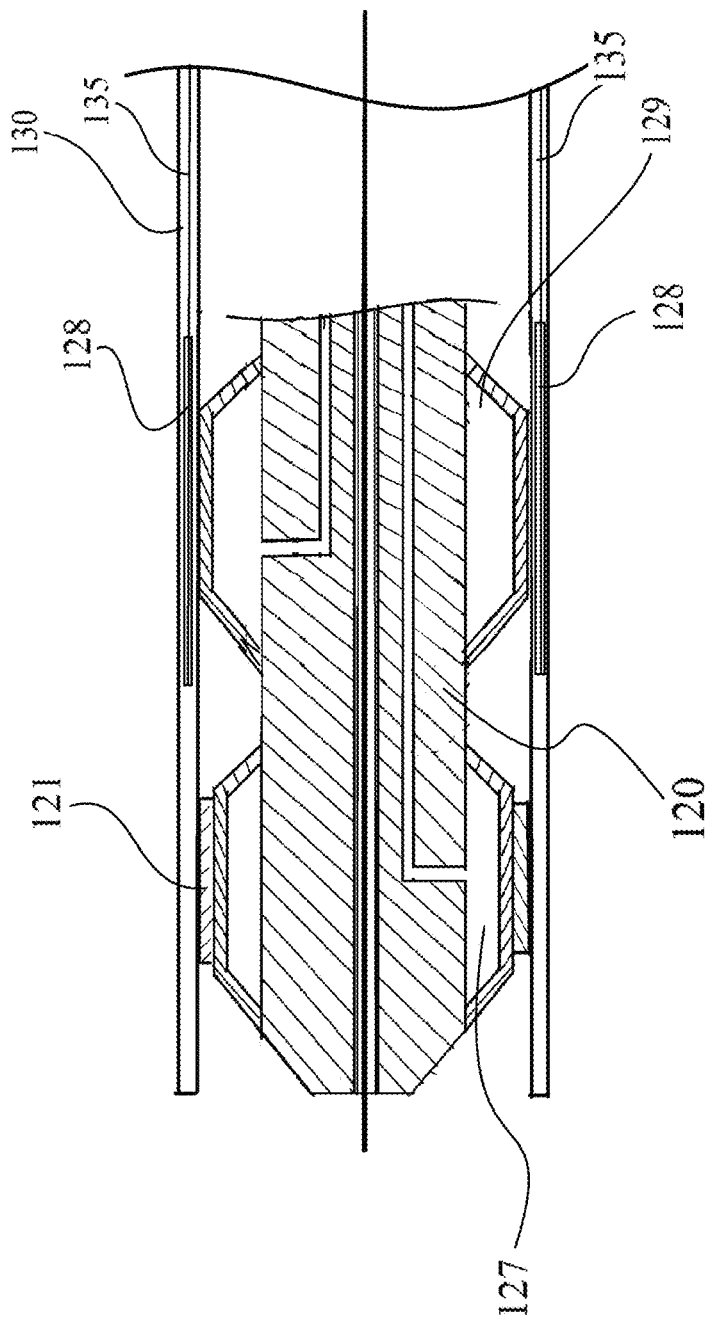
FIG. 32 illustrates a sectional view of a transporter catheter and an outer catheter comprising a flexible tube connected to pull-wires.

In one embodiment, the heart valve delivery system comprises an outer catheter 130 with a flexible tube 128 located at a distal portion of the outer catheter 130 (See FIG. 32), pull-wires 135 connected to the flexible tube 128, a transporter catheter 120 placed inside the outer catheter 130 with the anchoring balloon 129 positioned proximate to the flexible tube 128 of the outer catheter whereby when the anchoring balloon 129 is inflated, it presses on at least a portion of the flexible tube 128 of the outer catheter 130. The system further comprises a prosthetic heart valve disposed over the first balloon 127. In another embodiment, the anchoring balloon 129 is formed on a flexible tube included in the transporter catheter 120. Inflating the anchoring balloon 129 anchors the transporter catheter 120 to the outer catheter 130, and the outer catheter 130, the transporter catheter 120 and the prosthetic heart valve 121 may be advanced as a single unit through a patient's vasculature. A fluid is used to inflate or deflate the balloons. Increasing the pressure of the fluid inside the anchoring balloon increases the stiffness of the anchoring balloon. Decreasing the pressure of the fluid inside the anchoring balloon reduces the stiffness of the anchoring balloon and makes the anchoring balloon flexible. The variations in flexibility allowed by the anchoring balloon(s) to the heart valve delivery system provides ease of maneuvering to the user when the advancing of the heart valve delivery system through curvatures in the patient's vasculature.

After the heart valve delivery system has been advanced such that the valve is located proximal to the native diseased valve 123 (see FIG. 29), the transporter catheter 120 may be disengaged from the outer catheter 130 by deflating the anchoring balloon 129 and the transporter catheter 120 may be distally advanced relative to the outer catheter 130 to better position the valve 121 within the native leaflets 123. The ability of the anchoring balloon 129 to engage with and to disengage from the outer catheter 130 at desired locations inside the outer catheter allows the user to align the prosthetic valve 121 with respect to the native diseased valve 123. As a result, after the transporter catheter 120 is advanced distally, the prosthetic valve 121 may be advanced into the center of the native diseased valve 123. Furthermore, the transporter catheter 120 provides sufficient push-ability to push the prosthetic valve 121 across the stenotic leaflets 123.

In another embodiment (see FIG. 29), a method of delivering a prosthetic valve to a native valve site comprises disposing an expandable prosthetic valve over the first balloon 127 (see FIG. 28) or the second balloon 125 (see FIG. 30) formed at a distal-end portion of a transporter catheter, placing the transporter catheter 120 inside the outer catheter 130 having a steerable section, which is actuated by a pull-wire, anchoring the transporter catheter 120 to the outer catheter 130 using the anchoring balloon 129, and advancing the heart valve delivery system for the prosthetic valve towards the native valve site. The prosthetic valve 121 may be advanced outside of the outer catheter after navigating the aortic arch 122. After reaching the native valve site, the first balloon 127 (if the catheter is FIG. 28 was used) or the second balloon 125 (if the catheter in FIG. 30 was used) is inflated to deploy the prosthetic valve at a location of the diseased valve 123.

Figure 33:
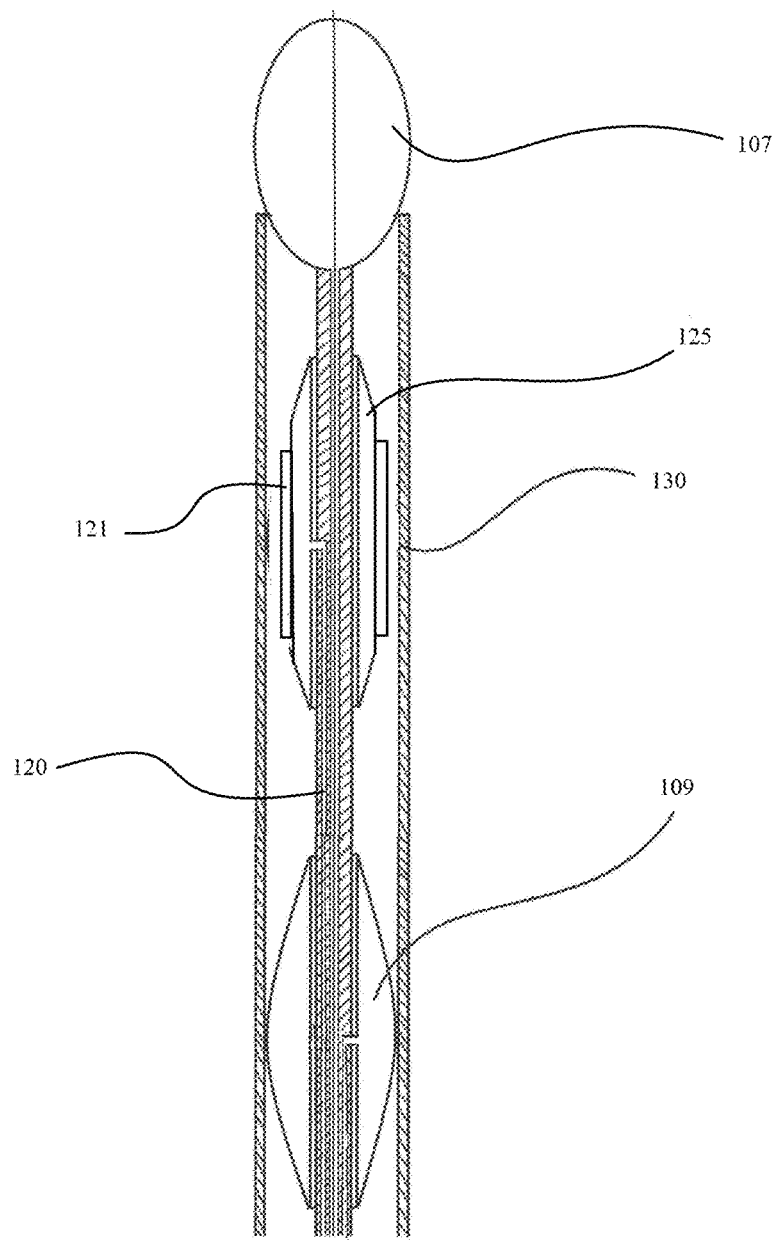
FIG. 33 illustrates a sectional view of a transporter catheter and an outer catheter showing an orienting balloon protruding outside the outer catheter, a heart valve crimped on a second balloon and an anchoring balloon anchoring the transporter catheter to the outer catheter.
Figure 34:
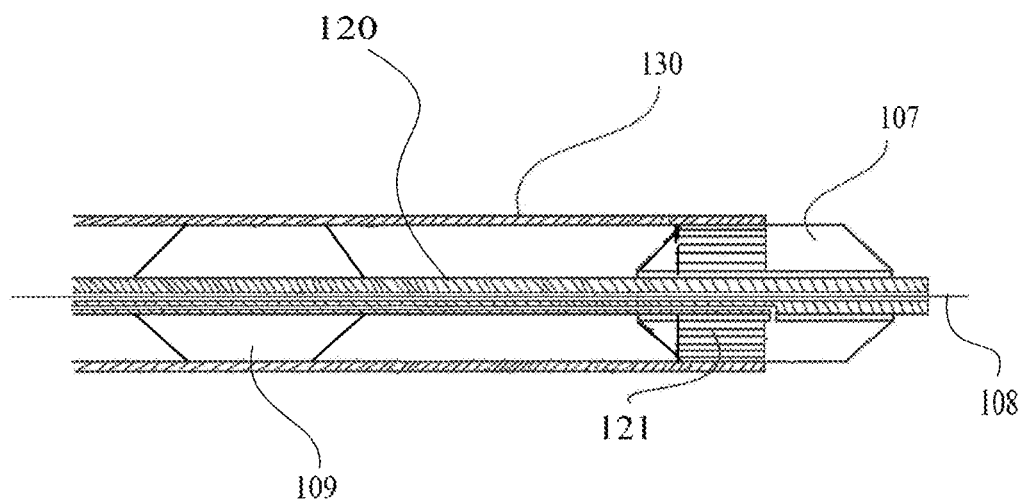
FIG. 34 illustrates a sectional view of a transporter catheter and an outer catheter showing a first portion of an orienting balloon protruding outside the outer catheter, a valve disposed on a second portion of the orienting balloon inside the outer catheter, and an anchoring balloon anchoring the transporter catheter to the outer catheter.

An embodiment illustrated in FIG. 33 shows a transporter catheter 120 inside an outer catheter 130, with the orienting balloon 107 protruding outside the outer catheter 130. The valve 121 is crimped on the second balloon 125, and the anchoring balloon 109 anchors the transporter catheter 120 to the outer catheter 130. FIG. 34 illustrates an embodiment in which a first part of the orienting balloon 107 protrudes outside the outer catheter 130 and the valve 121 is disposed over a second part of the orienting balloon that is located inside the outer catheter 130. The anchoring balloon 109 anchors the transporter catheter 120 to the outer catheter 130.

Figure 35:
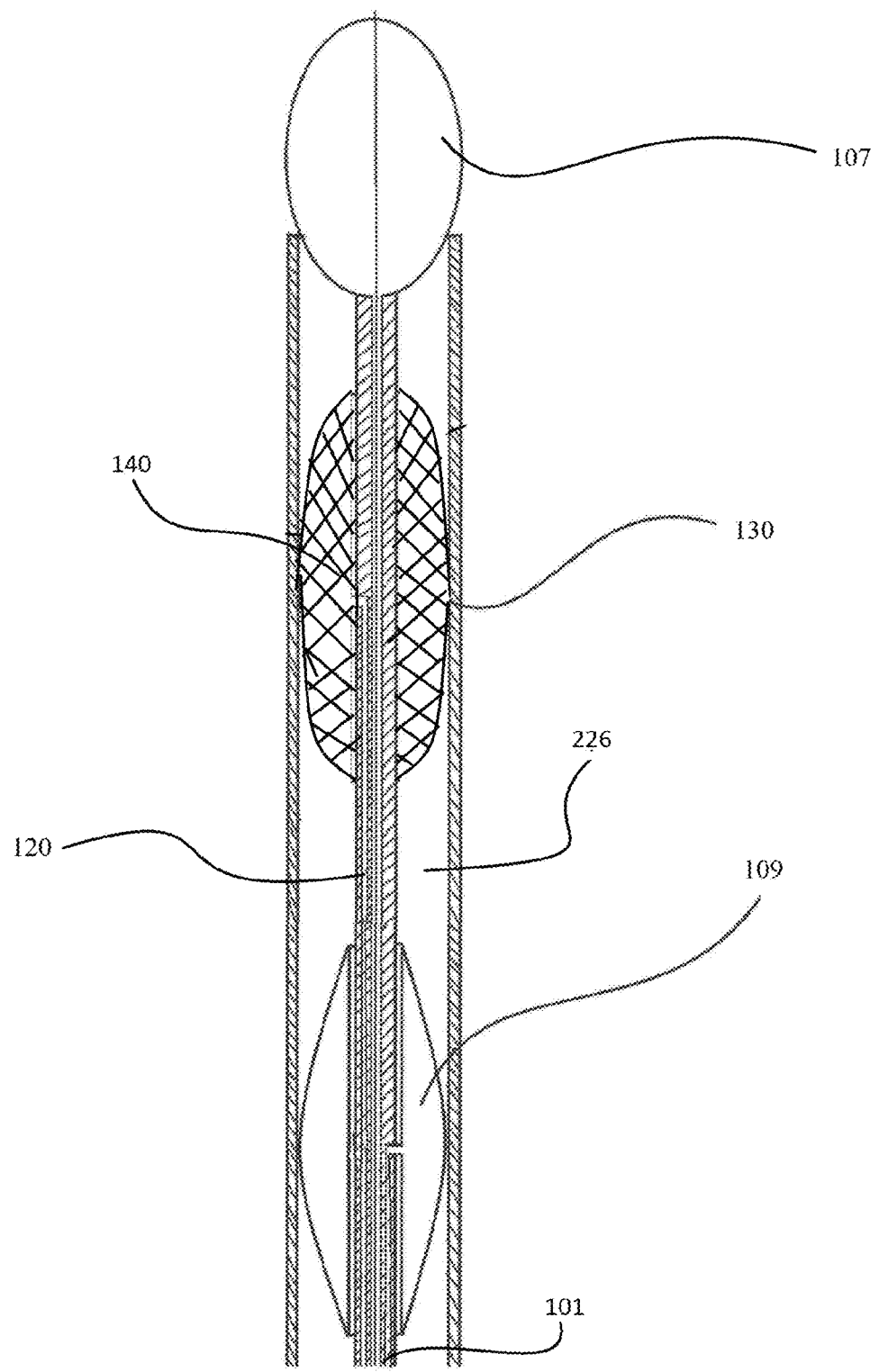
FIG. 35 is a perspective view of a transporter catheter in accordance with one embodiment of the present invention showing a clot treatment device disposed on the transporter catheter.

In another embodiment of the invention, the transporter catheter is configured to transport a clot treatment device in a system for treating embolism. The clot treatment device is configured for restoring blood flow through a clot and for removing at least a portion of the clot. An embodiment illustrated in FIG. 35 depicts a transporter catheter 120 inside an outer catheter 130, with the orienting balloon 107 protruding outside the outer catheter 130 and the anchoring balloon 109 anchors the transporter catheter 120 to the outer catheter 130. In one embodiment, the clot treatment device 140 is positioned on the transporter catheter at a location between the orienting balloon 107 and the anchoring balloon 109. The clot treatment device 140 is constrained by the outer catheter 130 and is in its undeployed or compressed state. The clot treatment device 140 is compressed to fit within the diameter of a lumen 226 of the outer catheter 130 in the undeployed state.

In some embodiments, the clot treatment device 140 comprises a braided material. The shaft 101 of the transporter catheter 120 is configured to push or pull the transporter catheter. When the shaft 101 is pushed, the clot treatment device 140 is also pushed and when the shaft 101 is pulled, the clot treatment device 140 is also pulled. When the anchoring balloon 109 is inflated and the transporter catheter 120 is anchored to the outer catheter 130, the pushing and pulling of the transporter catheter 120 also results in pushing and pulling of the outer catheter 130. In one embodiment, the clot treatment device 140 has a generally cylindrical shape that, during use, creates a flow lumen through the clot material that restores blood flow across a clot. The treatment device 140 is not, however, limited to a generally cylindrical shape. For example, the shape can be generally conical, generally concave or generally convex along its axis such that the clot treatment device 140 creates a lumen for restoring the blood flow.

Figure 36:
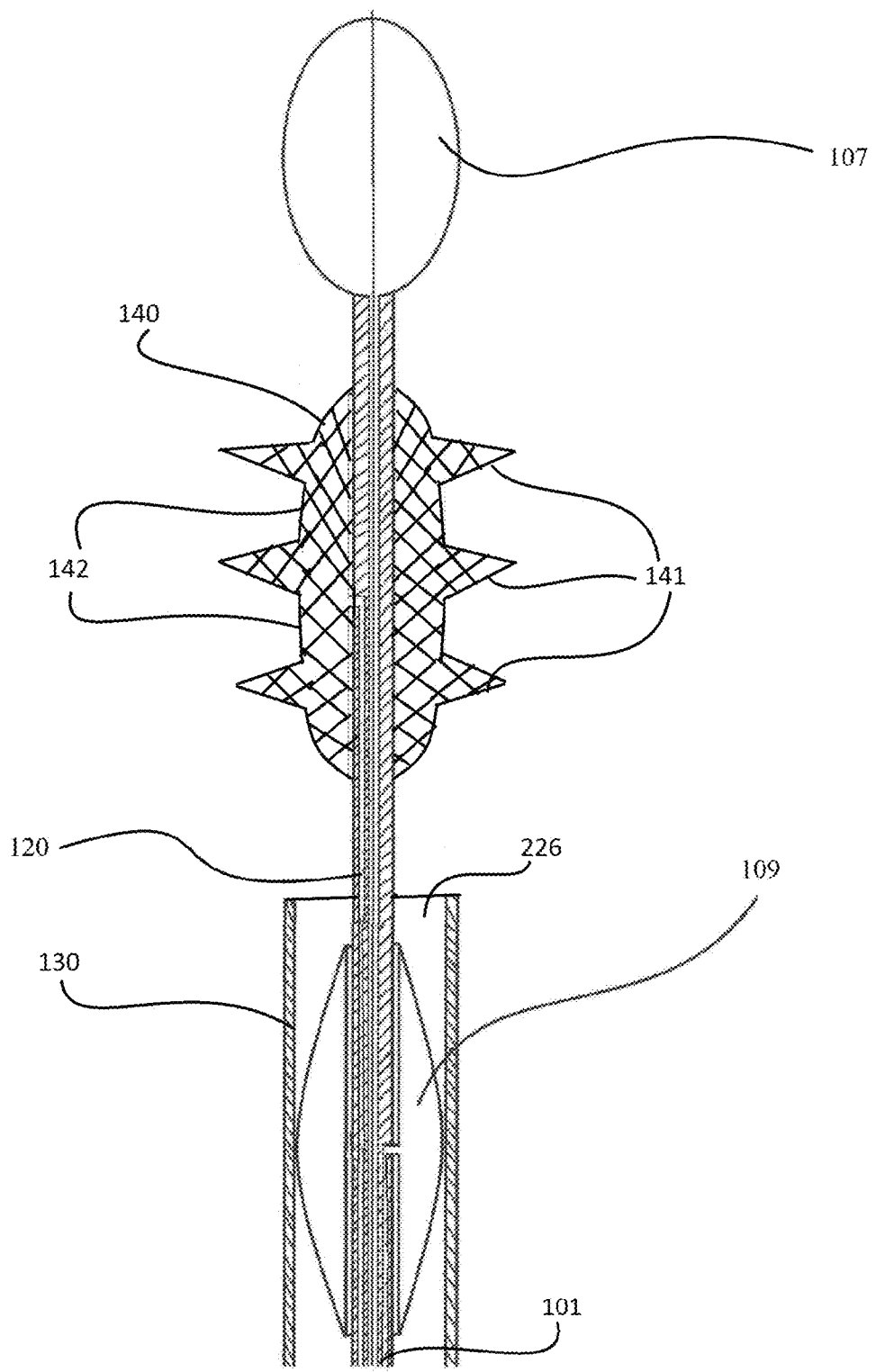
FIG. 36 is a perspective view of a transporter catheter in accordance with one embodiment of the present invention showing a deployed state of the clot treatment device.

FIG. 36 depicts an embodiment of a deployed state of the clot treatment device 140. The clot treatment device 140 has a plurality of capture elements, such as a series of radially extending capture portions 141 which are separated from each other by flow restoration portions 142. The flow restoration portions 142 are configured to expand outwardly from the low-profile undeployed state within the outer catheter lumen 226 to a first cross-sectional dimension (e.g., diameter) in the deployed state. For example, the flow restoration portions 142 can be generally cylindrical braided sections that expand radially outward from the undeployed stated to the deployed state. In some embodiments, the first cross-sectional dimension is greater than the diameter of the delivery catheter lumen 226. The capture portions 141 are configured to expand outwardly from the low-profile undeployed state to a second cross-sectional dimension greater than the first cross-sectional dimension in the deployed state. The capture portions 141 can project into the clot such that they extend transverse to a longitudinal axis of the clot treatment device 140, while the flow restoration portions 142 expand radially outward into the clot to open a passage through which blood can quickly resume flow through the vessel.

The clot treatment device 140 can be porous so blood flows therethrough. In this regard, many embodiments of the clot treatment device 140 are made from a mesh or braided material. The material can be a super-elastic material such as Nitinol or an alternative material such as cobalt chrome alloy. The device can be made from a wire lattice, wire braid or stent. The clot treatment device 140 can self-expand from the undeployed state to the deployed state. For example, the clot treatment device 140 can be a shape-memory material, such as Nitinol, and may be formed as a braid or a stent that is set to have the expanded configuration of the deployed state shown in FIG. 36 unless it is otherwise deformed or constrained, such as being elongated along the longitudinal axis to fit within the outer catheter as shown in FIG. 35. In other embodiments, the clot treatment device 140 can be actuated by a push/pull wire, tube or coil to move from the low-profile undeployed state to the expanded deployed state.

Figures 37A, 37B:
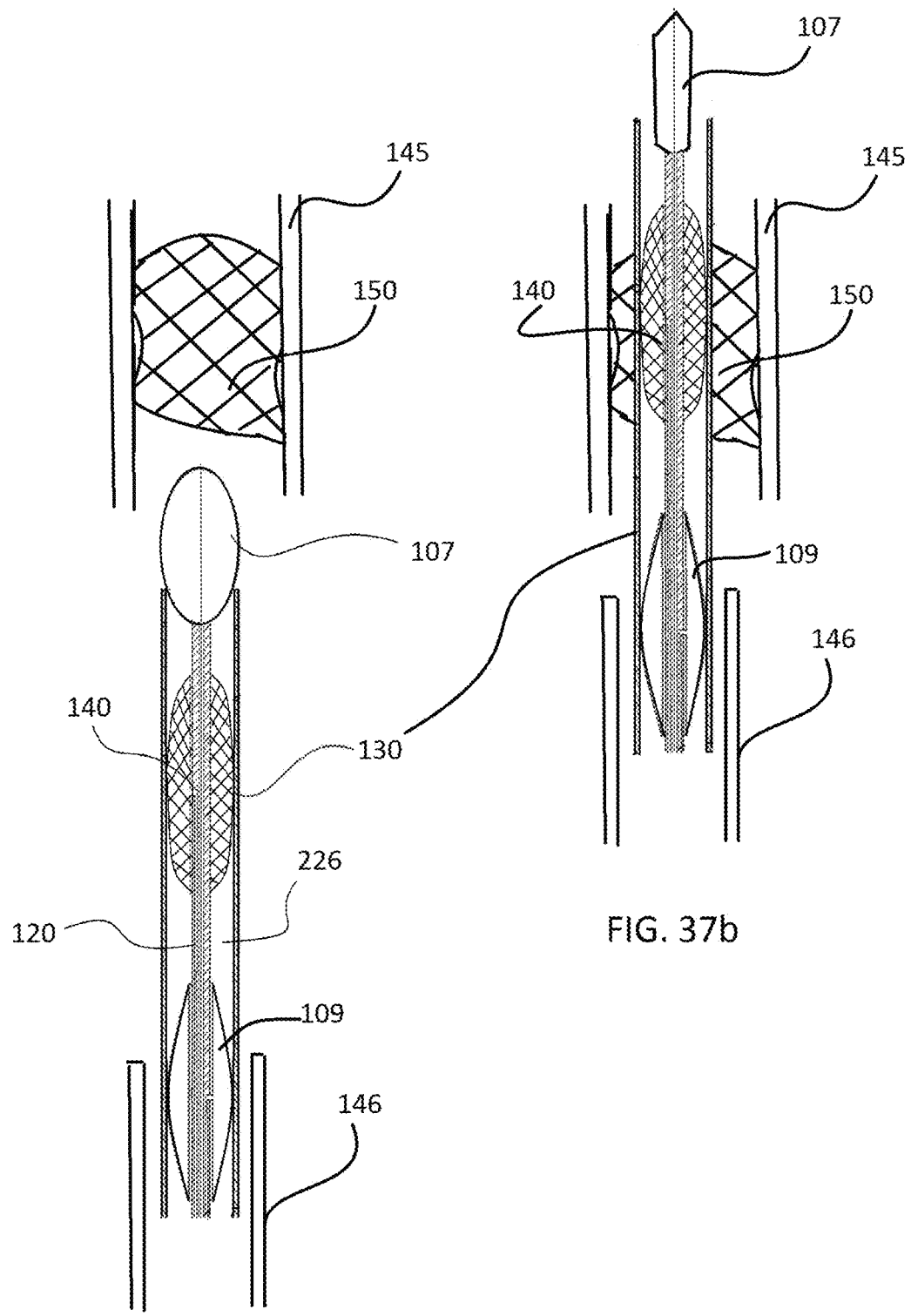
FIG. 37a-c are perspective views of a transporter catheter in accordance with one embodiment of the present invention showing advancing, positioning and deploying of the clot treatment device in a patient's vasculature using a transporter catheter.
Figure 37C:
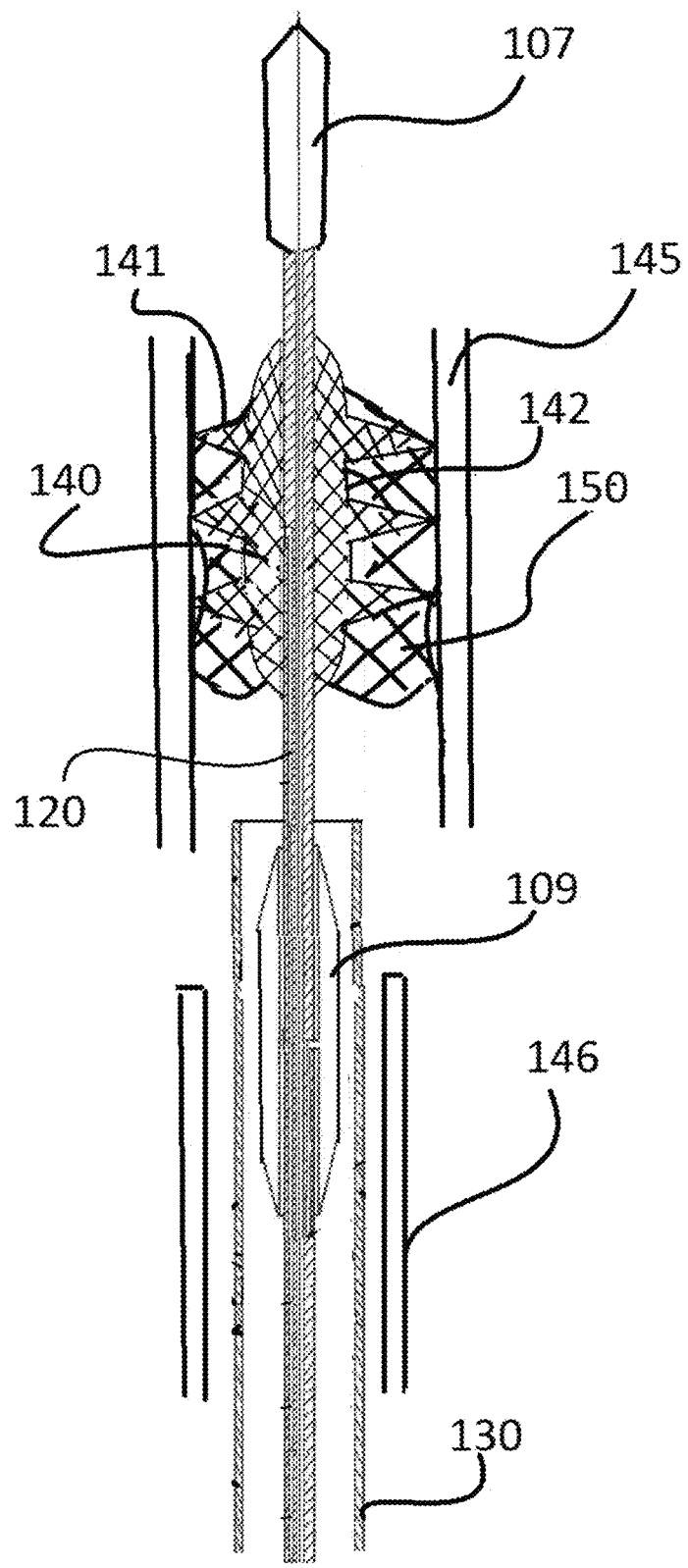

FIG. 37a depicts the clot treatment device 140 in its undeployed (i.e., compressed) state moved on a transporter catheter 120 and the outer catheter 130 until it is positioned proximal to the clot 145. The outer catheter may be moved through a mother catheter 146. As depicted in FIG. 37b, the outer catheter may then be pushed through the clot. The outer catheter and the transporter catheter may then be disengaged, e.g., by deflating the anchoring balloon (see FIG. 37c) and the outer catheter retracted from the clot and the clot treatment device 140 deployed. The clot treatment device 140 radially expands into the clot 150 and, in some embodiments, at least a portion of the clot treatment device 140 expands distal of the clot 150. For example, at least one of the radially extending capture portions 141 of the clot treatment device 140 is located distal to the clot 150 upon expansion of the clot treatment device 140. Additionally, the flow restoration portions 142 between the capture portions 141 also expand outwardly against a portion of the clot 150 to form a flow passage through the clot treatment device 140. The transporter catheter and the clot treatment device are then retracted in the outer catheter and during retraction a portion of the clot is also pulled in the outer catheter. In addition to restoring blood flow, the expansion of the clot treatment device 140 also deforms the clot material by pushing, penetrating and/or otherwise cutting into the clot material. This enhances the subsequent removal of the clot 150 since portions of the clot 150 may be captured and retained (1) between the radially extending portions 141; (2) through the pores of the mesh forming the radially extending portions 141; (3) along the longitudinal cylindrical sections 142 between the radially extending portions 141 of the removal device 140; and (4) within the clot treatment device 140 itself.

It should be appreciated that several of the above-disclosed and other features and functions, or alternatives or varieties thereof, may be desirably combined into many other different systems or applications. Also, it should be appreciated that various alternatives, derivatives, modifications, variations or improvements thereof or therein may be subsequently made by those skilled in the art, which are also intended to be encompassed by the following claims.

In the description above, for the purposes of explanation, certain requirements and certain details have been included in order to provide an understanding of the embodiments. It will be apparent however, to one skilled in the art, that one or more other embodiments may be practiced without some of the requirements or details. The particular embodiments described are not provided to limit the invention, but merely to illustrate it. The scope of the invention is not to be determined by the specific examples provided above. In other instances, well-known structures, devices, and operations have been shown in block diagram form or without detail in order to avoid obscuring the understanding of the description. Where appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in fewer than all features of a single disclosed embodiment. In another situation, an inventive aspect may include a combination of embodiments described herein or in a combination of fewer than all aspects described in a combination of embodiments.

The invention claimed is:

1. A system for advancing a treatment device through a lumen of a patient's vasculature, said system comprising: at least an outer sheath; at least a catheter located inside the outer sheath, said catheter comprising a proximal portion and a distal portion and the treatment device, said catheter configured to be pushed and/or torqued to advance and maneuver the system through the distal portion of the catheter and the treatment device is constrained in a compressed state; an orienting balloon positioned on the catheter distal the treatment device and at least an anchor comprising a mechanical connector positioned on the catheter, said anchor configured to be fully inflated or expanded to engage an inner wall of the outer sheath while the orienting balloon is configured to be fully inflated to engage the inner wall of the outer sheath such that the anchor and the orienting balloon are configured to apply a pull force on the outer sheath when the anchor and orienting balloon engage the inner wall of the outer sheath with the catheter, and the catheter is pushed and/or torqued forward; wherein a handle at a proximal end of the catheter is used to engage or disengage the catheter and the outer sheath using the mechanical connector; and wherein the catheter is steerable.

2. The system of claim 1, wherein a shaft of the catheter comprises at least one internal channel for a guidewire.

3. The system of claim 1, wherein the catheter is steerable.

4. The system of claim 1, wherein the at least one anchor comprises the mechanical connector and wherein a handle at a proximal end of the catheter is used to engage or disengage the catheter and the outer sheath using the mechanical connector.

5. The system of claim 1, wherein a shaft of the catheter comprises a varying degree of stiffness, a degree of stiffness of the varying degrees of stiffness at the proximal portion of the shaft being greater than a degree of stiffness of the varying degrees of stiffness at the distal portion of the shaft.

6. The system of claim 1, further comprising an orienting element formed at a distal end of the catheter, wherein at least a portion of the orienting element protrudes outside a distal end of the outer sheath.

7. The system of claim 1, wherein a shaft of the catheter comprises a helical coil or a plait-matrix assembly.

8. The system of claim 7, wherein the plait-matrix assembly comprises a braided-wire assembly, said braided-wire assembly being formed by braiding a plurality of flat wires, circular wires, or combinations thereof.

9. The system of claim 8, wherein the braided-wire assembly has a proximal portion and a distal portion, and wherein the braided wire assembly has a first stiffness at the proximal portion and a second stiffness at the distal portion, and wherein the first stiffness differs from the second stiffness.

10. The system of claim 1, wherein the treatment device is constrained in a compressed state.

11. The system of claim 10, wherein the treatment device is made of a super-elastic material.

12. The system of claim 10, wherein the treatment device is made of a material selected from a group including Nitinol and cobalt-chrome alloy.

13. The system of claim 10, wherein the treatment device can be actuated by a push-pull wire, tube or coil to move from a low-profile undeployed state to an expanded deployed state.

14. The system of claim 10, wherein the treatment device is a clot treatment device for treating embolism, and configured for restoring blood flow through a clot and for removing at least a portion of the clot.

15. The system of claim 14, wherein the clot treatment device comprises braided material.

16. The system of claim 14, wherein the clot treatment device is cylindrical in shape.

17. The system of claim 14, wherein the clot treatment device comprises capture portions to capture and retain the portion of the clot, and flow restoration portions to form a flow passage through the clot treatment device.

18. A system for advancing a treatment device through a lumen of a patient's vasculature, said system comprising:
at least an outer sheath;
at least a catheter located inside the outer sheath, said catheter comprising a proximal portion and a distal portion, said catheter configured to be pushed and/or torqued to advance and maneuver the system through a patient's vasculature;
the treatment device, said treatment device positioned at the distal portion of the catheter and the treatment device is constrained in a compressed state;
at least an anchor comprising a mechanical connector, said anchor configured to engage at least the catheter with at least the outer sheath;
wherein the anchor is configured to apply a pull force on the outer sheath when the anchor engages the outer sheath with the catheter, and the catheter is pushed and/or torqued forward;
wherein a handle at a proximal end of the catheter is used to engage or disengage the catheter and the outer sheath using the mechanical connector; and
wherein the catheter is steerable.

19. A system for advancing a treatment device through a lumen of a patient's vasculature, said system comprising: at least an outer sheath; at least a catheter located inside the outer sheath, said catheter comprising a proximal portion and a distal portion and the treatment device, said catheter configured to be pushed and/or torqued to advance and maneuver the system through the patient's vasculature; the treatment device positioned at the distal portion of the catheter and the treatment device constrained in a compressed state, an orienting balloon positioned on the catheter distal the treatment device, the treatment device being a clot treatment device for treating embolism, and configured for restoring blood flow through a clot and for removing at least a portion of the clot; at least an anchor selected from a group consisting of an inflatable balloon, a mechanical connector, and any combination thereof, positioned on the catheter, said anchor configured; to be fully inflated or expanded to engage an inner wall of the outer sheath while the orienting balloon is configured to be fully inflated to engage the inner wall of the outer sheath such that the anchor and the orienting balloon are configured to apply a pull force on the outer sheath when the anchor and the orienting balloon engage the outer sheath with the catheter, and the catheter is pushed and/or torqued forward.

* * * * *

UNITED STATES PATENT AND TRADEMARK OFFICE
CERTIFICATE OF CORRECTION

PATENT NO. : 11,878,132 B2
APPLICATION NO. : 18/022264
DATED : January 23, 2024
INVENTOR(S) : Rajendra Gurudas Sardesai, Samir Bipin Pancholy and Tejas Madhusudan Patel It is certified that error appears in the above-identified patent and that said Letters Patent is hereby corrected as shown below:

In the Claims

Column 32, Line 51-Column 33, Line 6, should read:
The invention claimed is:
1. A system for advancing a treatment device through a lumen of a patient's vasculature, said system comprising: at least an outer sheath; at least a catheter located inside the outer sheath, said catheter comprising a proximal portion and a distal portion and the treatment device, said catheter configured to be pushed and/or torqued to advance and maneuver the system through the patient's vasculature; the treatment device positioned at the distal portion of the catheter; an orienting balloon positioned on the catheter distal the treatment device and at least an anchor selected from a group consisting of an inflatable balloon, a mechanical connector, and any combination thereof, positioned on the catheter, said anchor configured to be fully inflated or expanded to engage an inner wall of the outer sheath while the orienting balloon is configured to be fully inflated to engage the inner wall of the outer sheath such that the anchor and the orienting balloon are configured to apply a pull force on the outer sheath when the anchor and orienting balloon engage the inner wall of the outer sheath with the catheter, and the catheter is pushed and/or torqued forward to advance the catheter to a desired location in the patient's vasculature.
Column 33, Lines 21-24 should read:
6. The system of claim 1, wherein at least a portion of the orienting balloon protrudes outside a distal end of the outer sheath when the orienting balloon is inflated.

Signed and Sealed this
Tenth Day of December, 2024

Katherine Kelly Vidal
*Director of the United States Patent and Trademark Office*